(12) United States Patent
Josel et al.

(10) Patent No.: US 11,021,472 B2
(45) Date of Patent: *Jun. 1, 2021

(54) USE OF COMPOUNDS COMPRISING TWO OR MORE HYDROPHOBIC DOMAINS AND A HYDROPHILIC DOMAIN COMPRISING PEG MOIETIES FOR STABILIZATION OF A CELL

(71) Applicant: Roche Diagnostics Operations, Inc., Indianapolis, IN (US)

(72) Inventors: Hans-Peter Josel, Weilheim (DE); Dieter Heindl, Munich (DE); Thomas Froehlich, Penzberg (DE); Stefanie Froehner, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/186,580

(22) Filed: Jun. 20, 2016

(65) Prior Publication Data

US 2018/0141935 A1 May 24, 2018

Related U.S. Application Data

(63) Continuation of application No. PCT/EP2014/078749, filed on Dec. 19, 2014.

(30) Foreign Application Priority Data

Dec. 20, 2013 (EP) .................... 13006039

(51) Int. Cl.
 *C07D 409/04* (2006.01)
 *C12M 1/42* (2006.01)
 *C07J 51/00* (2006.01)
 *G01N 33/543* (2006.01)
 *G01N 33/50* (2006.01)
 *C12N 5/00* (2006.01)

(52) U.S. Cl.
 CPC .......... *C07D 409/04* (2013.01); *C07J 51/00* (2013.01); *C12M 35/04* (2013.01); *C12N 5/0068* (2013.01); *G01N 33/5005* (2013.01); *G01N 33/54353* (2013.01); *C12N 2533/20* (2013.01); *C12N 2533/30* (2013.01)

(58) Field of Classification Search
 CPC .............................. C07D 409/04; C12M 36/04
 See application file for complete search history.

(56) References Cited

U.S. PATENT DOCUMENTS

| 2005/0208644 | A1 | 9/2005 | Takiguchi et al. |
| 2017/0146533 | A1 | 5/2017 | Josel et al. |
| 2017/0363624 | A1 | 12/2017 | Josel et al. |

FOREIGN PATENT DOCUMENTS

| EP | 1489167 A1 | 12/2004 |
| JP | 2005-312377 A | 11/2005 |
| JP | 2008-81486 A | 4/2008 |
| JP | 2011-185874 A | 9/2011 |
| WO | 1996/010399 A1 | 4/1996 |
| WO | 2000/051572 A1 | 9/2000 |
| WO | 2001/007011 A1 | 2/2001 |
| WO | 2002/076428 A1 | 10/2002 |
| WO | 2003/074691 A1 | 9/2003 |
| WO | 2008/073458 A2 | 6/2008 |
| WO | 2008/147438 A2 | 12/2008 |
| WO | 2009/103753 A1 | 8/2009 |
| WO | 2010/047793 A2 | 4/2010 |
| WO | 2010/141069 A2 | 12/2010 |
| WO | WO2010/141069 | * 12/2010 |
| WO | 2011/011055 A1 | 1/2011 |
| WO | 2012/065751 A1 | 5/2012 |
| WO | 2012/094642 A2 | 7/2012 |
| WO | 2013/148579 A1 | 10/2013 |
| WO | 2013/188763 A1 | 12/2013 |

OTHER PUBLICATIONS

Xiao et al. in Journal of Controlled Release 155, 272-281 (2011) (Year: 2011).*
Endocytotoc vesicle at www.rsc.org/publishing/journals/prospect/ontology.asp?id=GO:0030139&MSID=c1sm06846f (retrieved from the internet May 20, 2019) (Year: 2019).*
Kato et al. in Biotechnology Progress 20, 897-904 (2004) (Year: 2004).*
Baha, Takeshi et al., Induction of cell membrane protrusions by biotinylated PEG-cholesterol, Japan Society for Cell Biology, 2001, p. 59, vol. 54.
Thomas, Colin R. and Zhang, Zhibing, The Effect of Hydrodynamics on Biological Materials, Advances in Bioprocess Engineering II, 1998, 137-170.
Wikipedia, Unified atomic mass unit (Dalton), downloaded from https://en.wikipedia.org/wiki/Unified_atomic_mass_unit, Feb. 10, 2017, 5 pages.
International Search Report dated Feb. 5, 2015 in Application No. PCT/EP2014/078749, 4 pages.
Jensen, Tor W. et al., Lipopeptides Incorporated into Supported Phospholipid Monolayers Have High Specific Activity at Low Incorporation Levels, Journal of the American Chemical Society, 2004, pp. 15223-15230, vol. 126.
Kato, Koichi et al., Immobilized culture of nonadherent cells on an oleyl poly(ethylene glycol) ether-modified surface, BioTechniques, 2003, pp. 1014-1021, vol. 35, No. 5.
Kato, Koichi et al., Rapid Protein Anchoring into the Membranes of Mammalian Cells Using Oleyl Chain and Poly (ethylene glycol) Derivatives, Biotechnology Progress, 2004, pp. 897-904, vol. 20.
Kuhn, Phillip et al., A facile protocol for the immobilisation of vesicles, virus particles, bacteria, and yeast cells, Integrative Biology, 2012, pp. 1550-1555, vol. 4, No. 12.

(Continued)

*Primary Examiner* — Dennis Heyer
(74) *Attorney, Agent, or Firm* — Stinson LLP

(57) ABSTRACT

The present invention relates to the use compounds comprising two or more hydrophobic domains and a hydrophilic domain comprising a polyethylene glycol (PEG) moiety for stabilization of a cell, and methods related thereto.

9 Claims, 41 Drawing Sheets

(56) References Cited

OTHER PUBLICATIONS

Michaels, James D. et al., Protection Mechanisms of Freely Suspended Animal Cells (CRL 8018) from Fluid-Mechanical Injury. Viscometric and Bioreactor Studies Using Serum, Pluronic F68 and Polyethylene Glycol, Biotechnology and Bioengineering, 1991, pp. 169-180, vol. 38.
Miura, Suguru et al., Encapsulation of islets with ultra-thin polyion complex membrane through poly(elthylene glycol)-phospholipids anchored to cell membrane, Biomaterials, 2006, pp. 5828-5835, vol. 27.
Palomares, Laura A. et al., Evidence of Pluronic F-68 direct interaction with insect cells: impact on shear protection, recombinant protein, and baculovirus production, Enzyme and Microbial Technology, 2000, pp. 324-331, vol. 26.
Ramirez, Octavio T. and Mutharasan, R., The Role of the Plasma Membrane Fluidity on the Shear Sensitivity of Hybridomas Grown under Hydrodynamic Stress, Biotechnology and Bioengineering, 1990, pp. 911-920, vol. 36.
Sowana, D. D. et al., Studies of the shear protective effects of Pluronic F-68 on wild carrot cell cultures, Biochemical Engineering Journal, 2002, pp. 165-173, vol. 12.
Tomeczkowski, J. et al., Effect of cholesterol addition on growth kinetics and shear stress sensitivity of adherent mammalian cells, Enzyme & Microbial Technology, 1993, pp. 849-853, vol. 15.
Zhao, Bo et al., Nanotoxicity comparison of four amphiphilic polymeric micelles with similar hydrophilic or hydrophobic structure, Particle and Fibre Toxicology, 2013, 16 pps., vol. 10, No. 47.
Teramura et al., Control of cell attachment through polyDNA hybridization; Biomaterials, 2010, vol. 31, pp. 2229-2235.

* cited by examiner

Fig. 3

| 30min | target: 300.000 WBC | | MW | STD | Mean % | STD % |
|---|---|---|---|---|---|---|
| well | | | | | | |
| a1 | well treated | 61470 | | | | |
| a2 | well treated | 67259 | | | 21,64 | 2,71 |
| a3 | well treated | 74951 | | | | |
| a4 | well treated | 55956 | 64909 | 8131,2 | | |
| b1 | untreated | 55575 | | | | |
| b2 | untreated | 32017 | | | 9,89 | 6,56 |
| b3 | untreated | 17166 | | | | |
| b4 | untreated | 11481 | 29059,75 | 19683,1 | | |
| c1 | WBC treated | 213072 | | | | |
| c2 | WBC treated | 237475 | | | 77,28 | 4,39 |
| c3 | WBC treated | 243445 | | | | |
| c4 | WBC treated | 233327 | 231829,75 | 13176,7 | | |

| 90min | target: 300.000 WBC | | MW | STD | Mean % | Mean % |
|---|---|---|---|---|---|---|
| well | | | | | | |
| a1 | well treated | 124492 | | | | |
| a2 | well treated | 143548 | | | 47,62 | 4,33 |
| a3 | well treated | 154212 | | | | |
| a4 | well treated | 149208 | 142865 | 13000,28 | | |
| b1 | untreated | 46601 | | | | |
| b2 | untreated | 29206 | | | 9,32 | 4,58 |
| b3 | untreated | 21199 | | | | |
| b4 | untreated | 14882 | 27972 | 13732,98 | | |
| c1 | WBC treated | 237185 | | | | |
| c2 | WBC treated | 252844 | | | 83,12 | 2,72 |
| c3 | WBC treated | 254697 | | | | |
| c4 | WBC treated | 252559 | 249346,25 | 8160,72 | | |

| 120min | target: 300.000 WBC | | MW | STD | Mean % | Mean % |
|---|---|---|---|---|---|---|
| well | | | | | | |
| a1 | well treated | 167671 | | | | |
| a2 | well treated | 177678 | | | 57,02 | 6,37 |
| a3 | well treated | 192194 | | | | |
| a4 | well treated | 146708 | 171062,75 | 19104,5 | | |
| b1 | untreated | 46402 | | | | |
| b2 | untreated | 35669 | | | 9,74 | 4,88 |
| b3 | untreated | 20989 | | | | |
| b4 | untreated | 13798 | 28214,5 | 14633,3 | | |
| c1 | WBC treated | 256949 | | | | |
| c2 | WBC treated | 268552 | | | 86,23 | 2,43 |
| c3 | WBC treated | 258291 | | | | |
| c4 | WBC treated | 250979 | 258692,75 | 7300,9 | | |

Fig. 6C
crude product:
5'- -myristic acid- -myristic acid- -PEG 2000- -Fluorescein- -Biotin-TEG- -3'
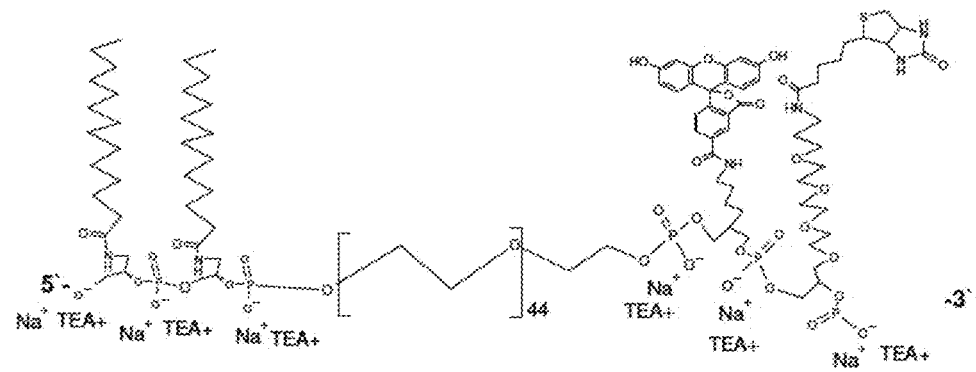
side product 1:
5'- -myristic acid- -PEG 2000- -Fluorescein- -Biotin-TEG- -3'
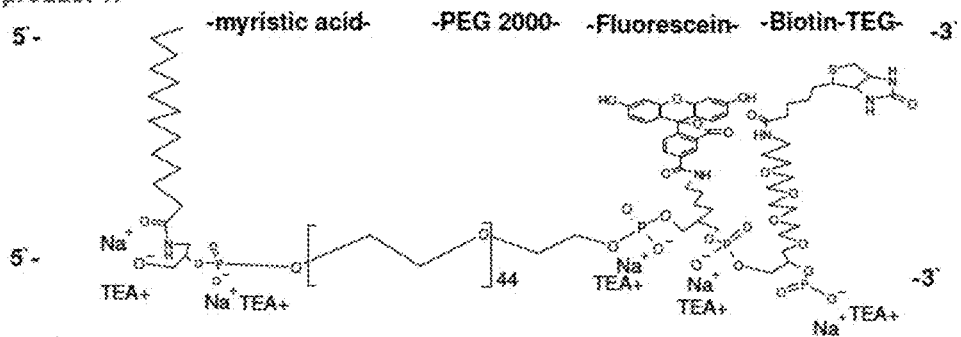
side product 2:
5'- -PEG 2000- -Fluorescein- -Biotin-TEG- -3'
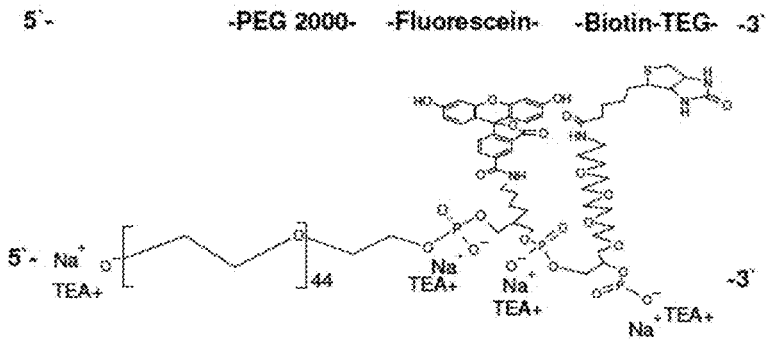
side product 3:
5'- -Fluorescein- -Biotin-TEG- -3'
side product 4:
5'- -Biotin-TEG- -3'
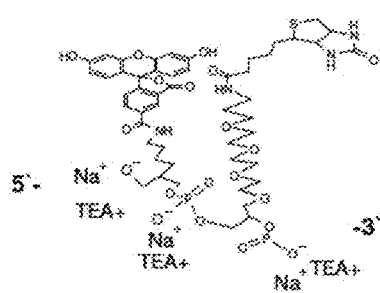
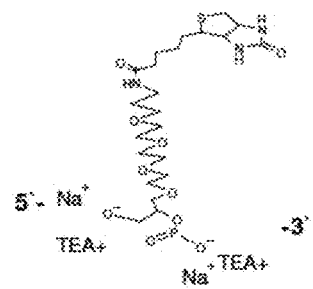

Figure 6C (continued)
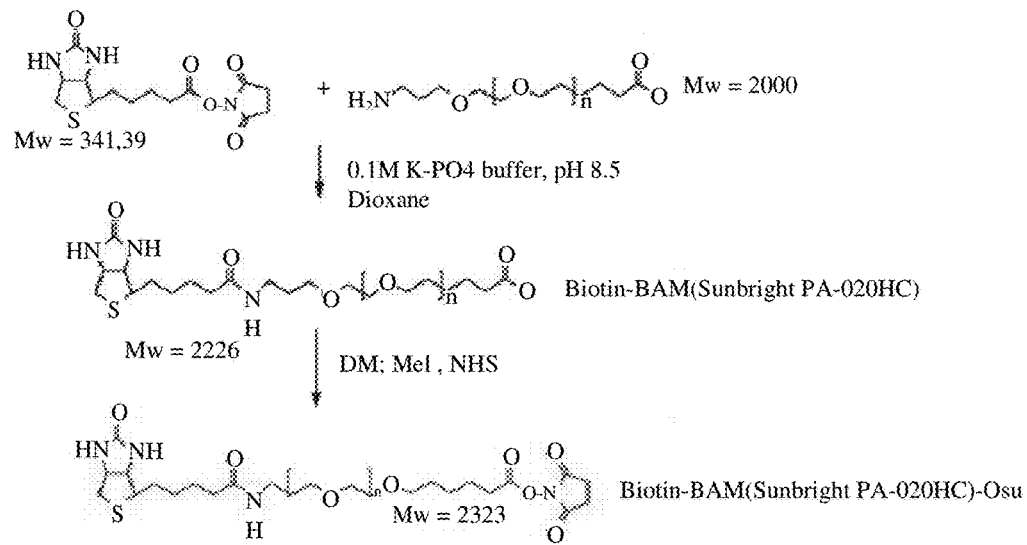
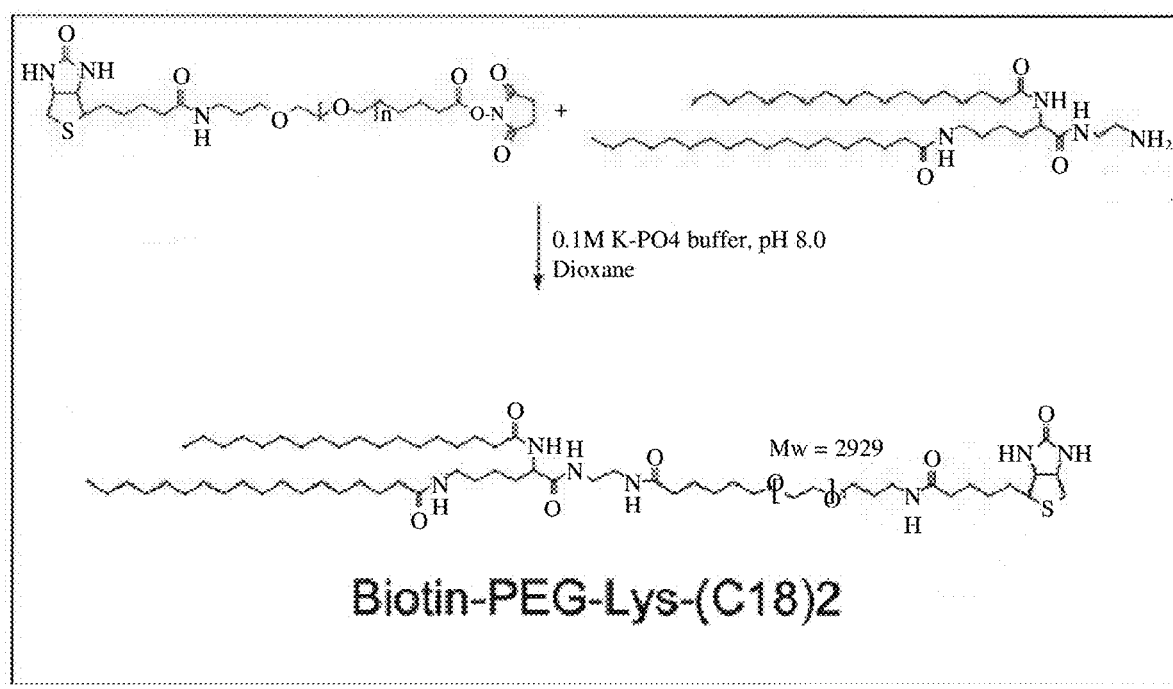

Fig. 12
29891272    Chol-TEG-Chol-TEG-Doubler-Biotin-dT
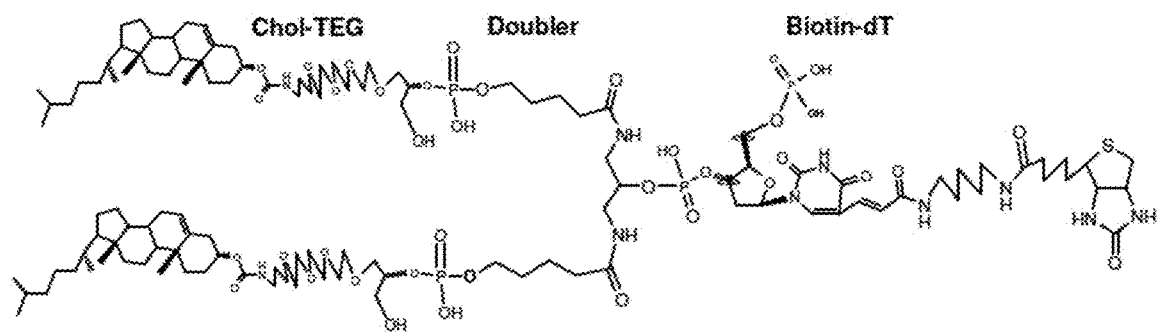
29891227    Myr-Chol-TEG-(Spacer-C18)₇-Fluos-Biotin-TEG
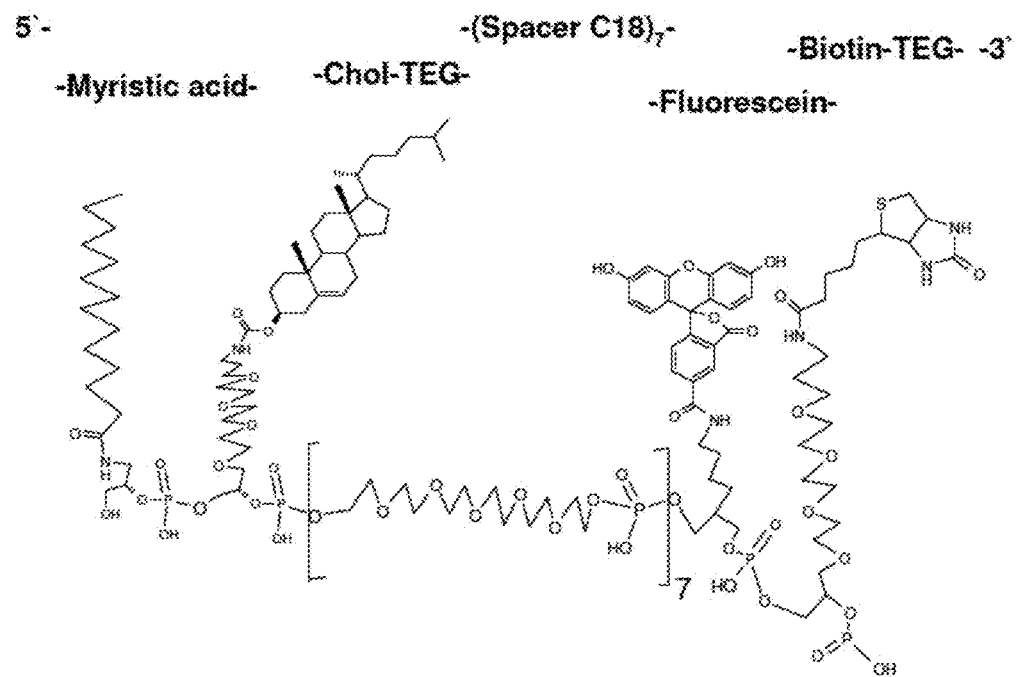

Fig. 12 (continued)
29891228  Chol-TEG- Myr-(Spacer-C18)₇-Fluos-Biotin-TEG
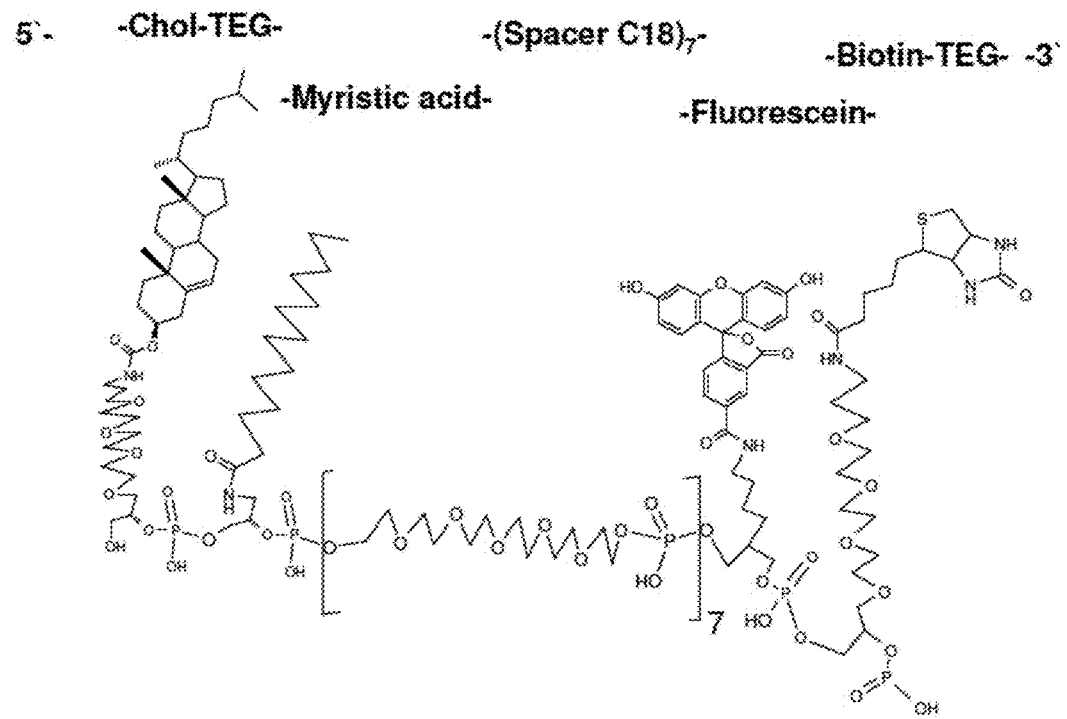
29891180  Chol-TEG-Chol-TEG-PEG2000-Fluos-Biotin-TEG
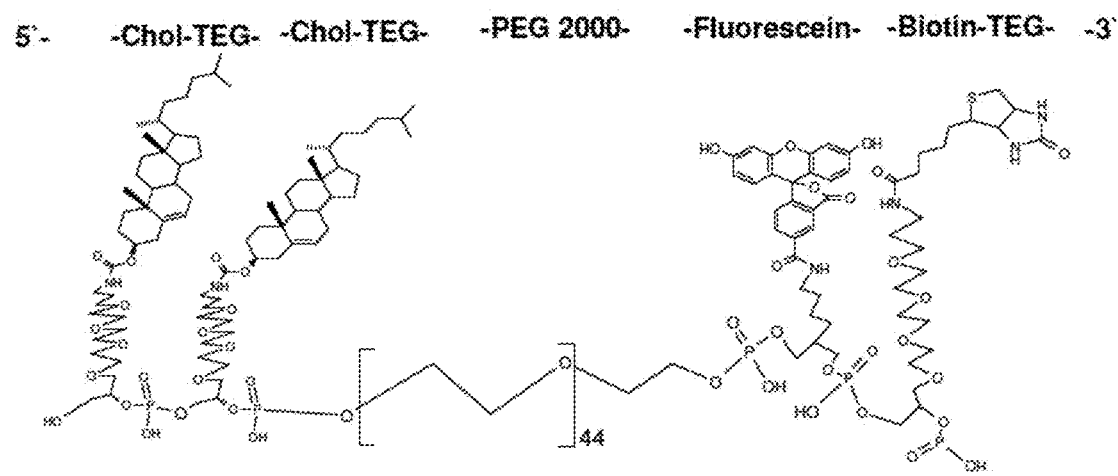

Fig. 12 (continued)
Phosphoramidites used for synthesis:
1 a)
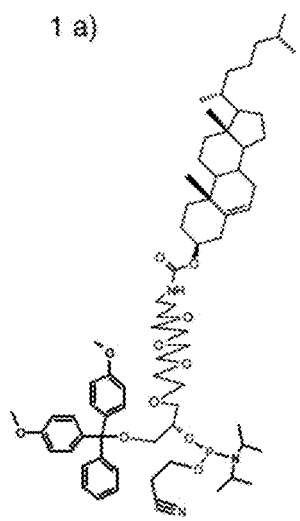
Cholesteryl-TEG-CE-phosphoramidite
a) cholesteryl-TEG-CE-PA (GlenResearch 10-1975),
1 b)
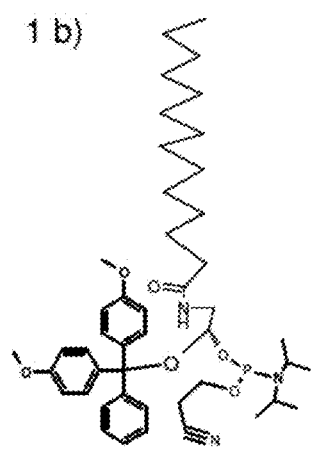
myristic acid-CE-phosphoramidite
b) myristic acid-CE-PA (inhouse production), Fig. 12 (continued)
1 c)
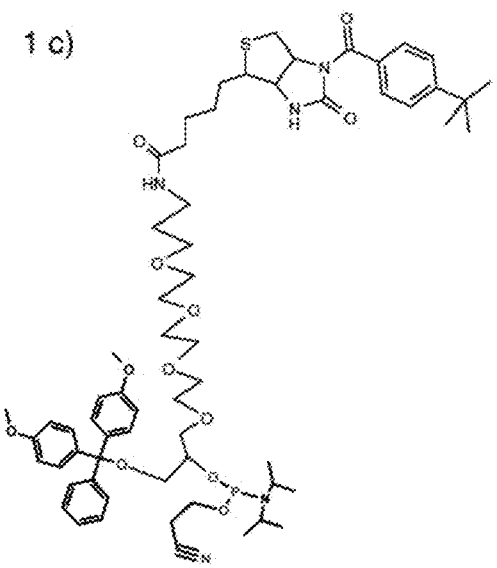
Biotin-TEG-CE-phosphoramidite
c) biotin-TEG-CE-PA (GlenResearch 10-1955),
1 d)
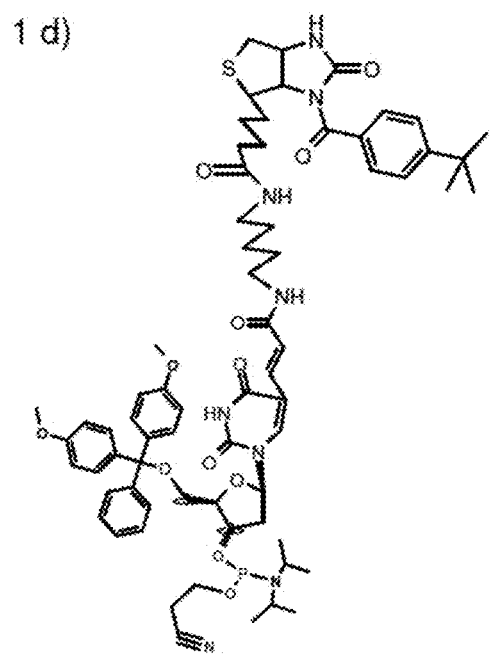
Biotin-dT-CE-phosphoramidite
d) biotin-dT-CE-PA (GlenResearch 10-1038), Fig. 12 (continued)
1 e)
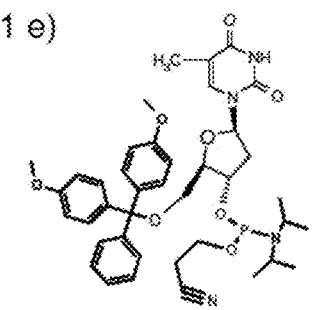
dT-CE-
phosphoramidite
1 f)
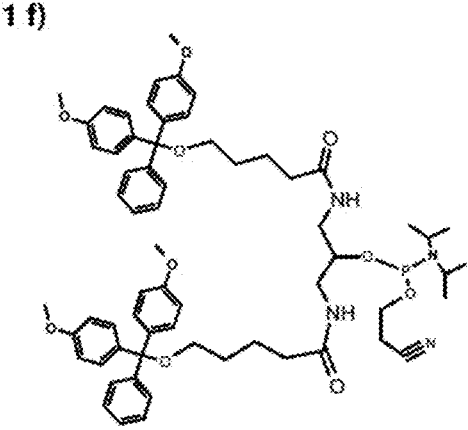
symmetric doubler-CE-
phosphoramidite
f) symmetric doubler-CE-PA (GlenResearch 10-1920),

Fig. 12 (continued)
1g
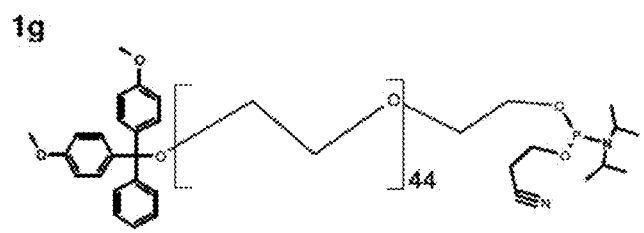
PEG-2000-CE-
phosphoramidite
g) PEG-200-CED-PA (ChemGenes CLP-2119),
1 h)
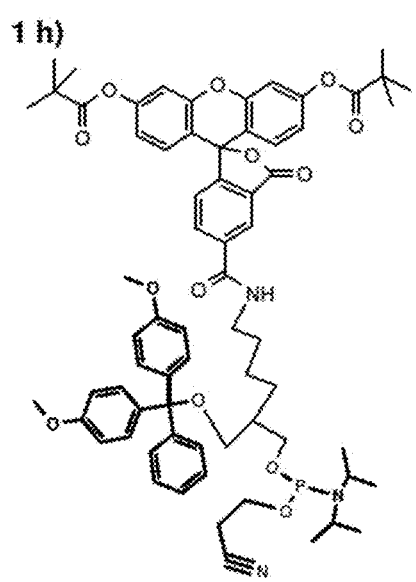
6-Fluorescein-CE-
phosphoramidite
h) 6-Fluorescein-CE-PA (GlenResearch 10-1964)

USE OF COMPOUNDS COMPRISING TWO OR MORE HYDROPHOBIC DOMAINS AND A HYDROPHILIC DOMAIN COMPRISING PEG MOIETIES FOR STABILIZATION OF A CELL

BRIEF SUMMARY OF THE DISCLOSURE

The present invention relates to the use compounds comprising two or more hydrophobic domains and a hydrophilic domain comprising a polyethylene glycol (PEG) moiety for stabilization of a cell, and methods related thereto.

BACKGROUND OF THE DISCLOSURE

Octavio T. et al. (Biotechnology and Bioengineering 1990 36:911-920) describe the influence of a shear protective agent, Pluronic F-68 (Poloxamer 188) a non-ionic surfactant, on hybridoma grown under hydrodynamic stress. It is disclosed in the paper that shear sensitivity of mammalian cells can be a problem impeding development of large scale animal cell cultivation. Octavio et al. investigated the relationship between plasma membrane fluidity, shear sensitivity and the influence of shear protection reagents added to the culture medium. They have shown that plasma membrane fluidity is decreased by adding cholesterol to the medium and they showed that cell survival of cells subjected to selected shear rates is higher when adding cholesterol to the medium compared to the control group. The same effect has been shown for Pluronic F-68.

Tomeczekowski J. et al. 1993; Enzyme and microbial technology 15: 849-853 describes cholesterol as suitable, physiological agent to protect cells from shear stress by decreasing the plasma membrane fluidity.

Laura A. et al. (Enzyme and Microbial Technology 2000 26:324-331) describes Pluronic F-68 as shear protective agent for animal cells from hydrodynamic stress and they investigate the mechanism of action of Pluronic F-68. Laura et al. review on different other publications showing that Pluronic F-68 show two protection mechanisms, a physical and a biological/cellular mechanism. Pluronic F-68 reduces the level of frequency of forces experienced by the cells, e.g. it stabilizes the foam layer and decreases the rising velocity of bubbles, thus reducing shear forces. On a cellular level Pluronic F-68 reduces plasma membrane fluidity.

Similar disclosures are found in Thomas C. et al. (Advances in Bioprocess Engineering 1998: 137-171); Ramirez O. et al. (Biotechnological and Bioengineering 1990; 36:911-920); Michaels J. et al. (Biotechnological and Bioengineering 1991; 38:169-180) and Sowana D. et al. (Biochemical Engineering Journal 2002; 12:165-173).

However, cholesterol is a hydrophobic molecule and therefore it has to be dissolved in solvents like DMSO or alcohol which show cell toxicity at concentrations higher than 1% resulting in a limited cholesterol concentration which can be used to stabilize the cells.

In addition it has been shown that monovalent molecules like cholesterol or Pluronic F-68 have lower shear protective properties compared to bivalent molecules. Therefore the concentration of the monovalent protective agents, as already published, has to be higher compared to bivalent molecules.

Finally, monovalent molecules can be internalized into the cell interior and therefore can change the cell physiology.

There is therefore a need for new uses and methods employing compounds and compositions which are able to bind to cells without affecting viability and/or which stabilize cells. For example, such uses and methods should stabilize cells exposed to stress like shear stress.

BRIEF DESCRIPTION OF THE FIGURES

FIG. 3: shows the results of Example 6 after 30, 90 or 120 minutes incubation.

FIG. 12: shows structures of further compounds for use according to the invention and reference compounds, as well as intermediates.

DETAILED DESCRIPTION OF THE INVENTION

Figure 1:
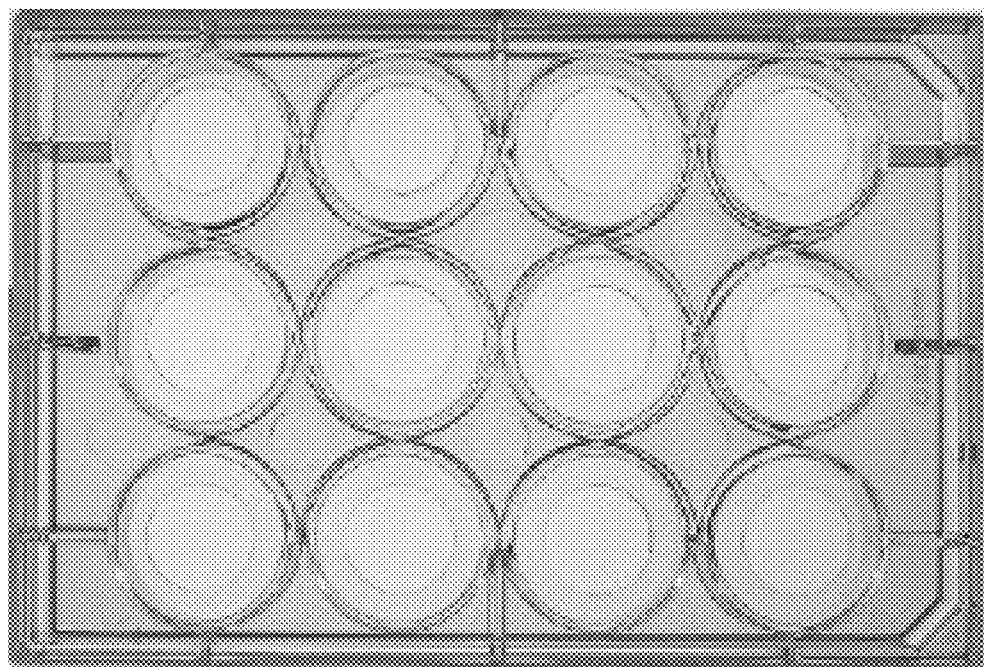
FIG. 1: Plate used in experiment of Example 6: Streptavidin treated MTP (Microcoat), 12 Well, NUNC, MC ID: 604 176, Lot Nr: 1665 C2

The uses and methods of the invention solve this problem and overcome the disadvantages of the prior art. The uses and methods of the invention are in particular able to effectively stabilize cells, in particular against shear stress.

In one embodiment, the present invention relates to the use of a compound comprising, preferably consisting of, two or more hydrophobic domains attached to a hydrophilic domain, wherein the two or more hydrophobic domains are covalently bound to said hydrophilic domain, and wherein the two or more hydrophobic domains each comprise a linear lipid, a steroid or a hydrophobic vitamin, and wherein the hydrophilic domain comprises a polyethylene glycol (PEG) moiety, for the stabilization of a cell.

A polyethylene glycol (PEG) moiety is understood as linear or branched, preferably linear moiety comprising at least one —O—$CH_2$—$CH_2$— moiety, preferably 1 to 50, more preferably 4 to 30 —O—$CH_2$—$CH_2$— moieties.

The basic principle of stabilization is postulated to be that a terminal hydrophobic part of the compound anchors into the lipid bi-layer of the cell membrane. This hydrophobic molecule immobilization decreases the plasma membrane fluidity and therefore stabilizes the cell.

The stabilizing, in particular shear-protective effect is in particular proven for cholesterol, myristic acid and stearic acid as hydrophobic moieties in the compounds which can be used in a method of the invention (see Example 5).

"Stabilization of a cell" according to the present invention is understood as higher viability of a cell compared to the viability of a control cell without application of the method of the invention or the compounds to be used according to the invention under defined conditions, which are preferably shear stress conditions, like centrifugation, e.g. centrifugation of cells at 500 g for 20 min. Stabilization is typically determined on a population of cells, e.g. 2, 10, 100 or more cells, and the respective mean viability of the cell populations are compared. A higher mean viability of the treated cell population compared to the mean viability of the control cell population indicates a stabilizing effect. Viability may be determined by determining cell morphology, cell viability and/or cell recovery. Methods for determining cell morphology, cell viability and cell recovery are known in the art. In particular, the methods as described in Example 5 may be used. For determining cell morphology, visual inspection by microscopy may be performed. For determining cell viability, a cell viability test using WST-1 proliferation kit (RAS) may be performed. In particular, a viability which is at least 5%, more preferably 10%, even more preferably 20% higher than the viability of the control cell or control cell population indicates a stabilizing effect and thus stabilization of a cell or cell population.

In a preferred embodiment of the present invention, stabilizing is stabilizing during exposure of the cell to shear forces.

In a further preferred embodiment, stabilizing is stabilizing during exposure of the cell to shear forces by centrifugation, large scale cell cultivation, flow cytometry, fluorescence-activated cell sorting and/or bead-based cell separation.

In a further preferred embodiment, stabilizing is stabilizing during exposure of the cell to centrifugation, large scale cell cultivation, flow cytometry, fluorescence-activated cell sorting and/or bead-based cell separation.

"Shear stress" or "shear forces" is understood as is defined as the component of stress coplanar with a material cross section. Shear stress arises from the force vector component parallel to the cross section. Such stress is imposed to cells during centrifugation, large scale cell cultivation, flow cytometry, fluorescence-activated cell sorting and/or bead-based cell separation.

Centrifugation is a process that involves the use of the centrifugal force for the sedimentation of mixtures with a centrifuge, used in industry and in laboratory settings. Cells may be centrifugated for example with 100 g, 200 g, 500 g, 1000 g or more, for 5 or more minutes, for example for 1 hour or 5 hours.

Flow cytometry is a laser-based, biophysical technology employed in cell counting, cell sorting, biomarker detection and protein engineering, by suspending cells in a stream of fluid and passing them by an electronic detection apparatus. It allows simultaneous multiparametric analysis of the physical and chemical characteristics of up to thousands of particles per second.

Fluorescence-activated cell sorting (FACS) is a specialized type of flow cytometry. It provides a method for sorting a heterogeneous mixture of biological cells into two or more containers, one cell at a time, based upon the specific light scattering and fluorescent characteristics of each cell.

In bead-based cell separation methods, beads, like magnetic beads are used, which typically coated with a member of a bioaffine binding pair, like an antibody. Using such beads, cells of interest carrying a marker recognized by such binding pair member may be bound and subsequently separated, for example using the magnetic properties. The separation step imposes shear forces to cells bound to beads.

Large scale cell cultivation is understood as cultivation of cells in a volume of than 10 ml, 50 ml, 100 ml or 1 l of liquid media or more, in particular as batch cultivation comprising stirring. Such stirring also means shear stress for the cells to be cultivated.

The compounds for use according to the invention comprise, preferably consist of, two or more hydrophobic domains and a hydrophilic domain.

Preferably, 2, 3, 4, 5, 6, 7, 8, 9 or 10 hydrophobic domains are covalently bound to said hydrophilic domain.

For stabilizing effects, it was found advantageous that the compounds for use according to the invention preferably comprise 2 or 3 or more, more preferably 2 or 3 hydrophobic domains.

With particular advantage, in a specific embodiment at least one lipid hydrophobic domain comprises a steroid, even more preferably cholesterol.

In one preferred embodiment of the invention, 2 or 3 hydrophobic moieties hydrophobic domains are covalently bound to said hydrophilic domain.

For the general understanding herein, a "hydrophobic moiety" is comprised in and forms the major portion of a "hydrophobic domain", thus determining the hydrophobic character thereof.

The hydrophobic moieties for the compounds comprising 2 or more hydrophobic moieties may be the same or may be different. For example, a compound comprising two hydrophobic domains may comprise 2 myristic acid moieties, or a myristic acid moiety and a cholesteryl moiety.

A cholesterol moiety is a particularly preferred hydrophobic moiety of compounds for use according to the invention.

In a preferred embodiment of the use, the said compound comprises, preferably consists of, two or more hydrophobic domains and a hydrophilic domain, wherein the two or more hydrophobic domains are covalently bound to said hydrophilic domain, and wherein the two or more hydrophobic domains each comprise a linear lipid, a steroid or a hydrophobic vitamin, and wherein the hydrophilic domain comprises a compound of Formula (I):

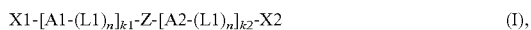

$$X1-[A1-(L1)_n]_{k1}-Z-[A2-(L1)_n]_{k2}-X2 \qquad (I),$$

wherein

Z is linear polyethylene glycol (PEG) moiety containing 1 to 100, preferably 1 to 50, more preferably 4-30 —O—CH$_2$—CH$_2$— moieties, wherein the polyethylene glycol moiety optionally comprises 1 or more spacer moieties SP connecting two —O—CH$_2$—CH$_2$— moieties, and wherein the linear PEG moiety optionally comprises a linker moiety L3 at one or both ends, each L1 is a linker moiety selected independently from each other, each n is either 0 or 1, selected independently from each other, A1 and A2 are bifunctional or trifunctional moieties selected independently from each other, with the proviso that at least one A1 or A2 is trifunctional, k1 and k2 are integers between 0 and 10, selected independently from each other, with the proviso that at least one of k1 and k2 is not 0, X1 and X2 are independently selected from hydrogen or a protecting group, L3 is independently selected from a linear alkyl or alkenyl chain with 1 to 10 C atoms, which is optionally (i) interrupted by 1 to 3 N, O or S atoms, and/or (ii) substituted by 1 to 4 hydroxyl, carbonyl, amino or thiol groups, and wherein the two or more hydrophobic domains are covalently bound to said hydrophilic domain via the trifunctional domains, or a salt thereof.

In a preferred embodiment, k1+k2≥2.

A lipid is a hydrophobic small molecule selected from fats, waxes, sterols, fat-soluble, hydrophobic vitamins, such as vitamins A, D, E, and K, fatty acids monoglycerides, diglycerides, triglycerides and phospholipids.

The hydrophobic domains each comprise, preferably consist of, a linear lipid, a steroid or a hydrophobic vitamin.

The linear lipid(s), steroid(s) or hydrophobic vitamin(s) may be bound directly to a trifunctional moiety or via a linker L2. An example for compounds wherein linear lipids are bound directly to a trifunctional moiety is compound myristic acid-myristic acid-(SpacerC18)7-Fluos-Biotin-TEG. An example for compounds wherein steroids is bound via a linker L2 to a trifunctional moiety is compound Cholesteryl-TEG-Cholesteryl-TEG-(SpacerC18)7-Fluos-Biotin-TEG. In this latter example, TEG (tetraethylenglycol) is the linker L2.

In one preferred embodiment, the hydrophobic domains each consist of a linear lipid, a steroid or a hydrophobic vitamin. In this event, it is apparent that the hydrophobic domain is hydrophobic, more preferably lipophilic as a linear lipid, a steroid or a hydrophobic vitamin is hydrophobic, more preferably lipophilic.

A hydrophobic moiety is understood as moiety that is repelled from a mass of water. Preferably, the moiety is lipophilic; i.e. it tends to dissolve in other non-polar lipophilic substances like fats or fatty acids.

In another preferred embodiment, the hydrophobic domains each comprise a linear lipid, a steroid or a hydrophobic vitamin and one or more further moieties. In this embodiment, the hydrophobic moiety as a whole is hydrophobic, more preferably lipophilic.

In an even more preferred embodiment, the hydrophobic domains of the invention comprising a linear lipid, a steroid or a hydrophobic vitamin are able to insert into a cell membrane. This can be determined by methods known in the art.

In one preferred embodiment, the 2 or 3 or more hydrophobic moieties of a compound for use according to the invention are different hydrophobic domains, or in case of 3 or more hydrophobic moieties, two or more are different or all are different from each other.

In a preferred embodiment of the invention, a first hydrophobic domain comprises, preferably consists of, a saturated fatty acid, especially myristic acid, stearic acid or behenic acid, particularly myristic acid, and/or a second hydrophobic domain comprises, preferably consists of, cholesterol. In case of a third hydrophobic domain, this domain preferably comprises, preferably consists of, cholesterol or a saturated fatty acid, especially myristic acid, stearic acid or behenic acid, particularly myristic acid and/or is the same as the first or second hydrophobic domain. In case of more than 4 hydrophobic domains, the same preferred embodiments as for the third hydrophobic domain applies.

In particular, compounds comprising at least one cholesterol moiety, in particular 1, 2, or 3 cholesterol moieties are especially preferred.

For stabilizing effects, the compounds for use according to the invention comprise 2 or 3 or more, more preferably 2 or 3 hydrophobic moieties.

This conformation was shown to have a higher binding affinity to the cells compared to monovalent molecules; i.e. molecules comprising one hydrophobic moiety of the invention. Therefore lower concentrations of the compounds for use according to the invention are needed to reach a shear protective effect compared to monovalent molecules.

The hydrophilic part of the molecule inhibits the internalization of the compound for use according to the invention and the shear protective effect is induced by incorporating of the hydrophobic part into the exterior plasma membrane. Experiments with labeled compounds for use according to the invention have confirmed that the compound just incorporates in the exterior plasma membrane without influencing the cell interior.

Moreover, the compounds for use according to the invention surprisingly exhibit advantageous binding or immobilizing effects on cells, as shown in detail in the Examples. Compounds further exhibiting an immobilizing effect further comprise a linking group. Compounds may also further comprise a label moiety. Such compounds may in addition be used for targeting and/or detecting cells.

Regarding the further application of cell labelling and immobilization, it was found in the Examples that compounds with hydrophobic moieties and further comprising a linking group and/or label moiety show a targeting and tight retaining of all cell types (see in particular Example 2). In particular cholesterol, myristic acid, stearic acid, and behenic acid moieties are found to be in particular useful for this purpose. With exemplary advantage and allowing to achieve quantitative cell targeting, compound 5'-CholesterylTEG-CholesterylTEG-PEG2000-Fluos-3 (internal Ref: BMO 29.891133) represents a preferred compound for use of the present invention.

Also, it was found that compounds containing two or three hydrophobic moieties further comprising a linking group were proven in experiments to be useful for quantitative cell immobilization.

According to the present invention, a "cholesterol-dual linker molecule" is understood as compound for use according to the invention containing two hydrophobic moieties, which are both cholesterol. Accordingly, a "myristic acid-triple linker molecule" is understood as compound for use according to the invention containing three hydrophobic moieties, which are all myristic acid.

The use of a compound containing two hydrophobic moieties, which are both cholesterol is especially preferred.

Further, the use of a compound containing two hydrophobic moieties, which are both myristic acid is especially preferred.

Such compounds were efficient in stabilizing cells according to Example 5.

According to the invention "asymmetric dual linker molecule" is understood as compound for use according to the invention containing two hydrophobic moieties, wherein the two hydrophobic moieties are different from each other.

The compounds for use according to the invention are described in the examples mostly in this modular, schematic way.

Figure 6A:
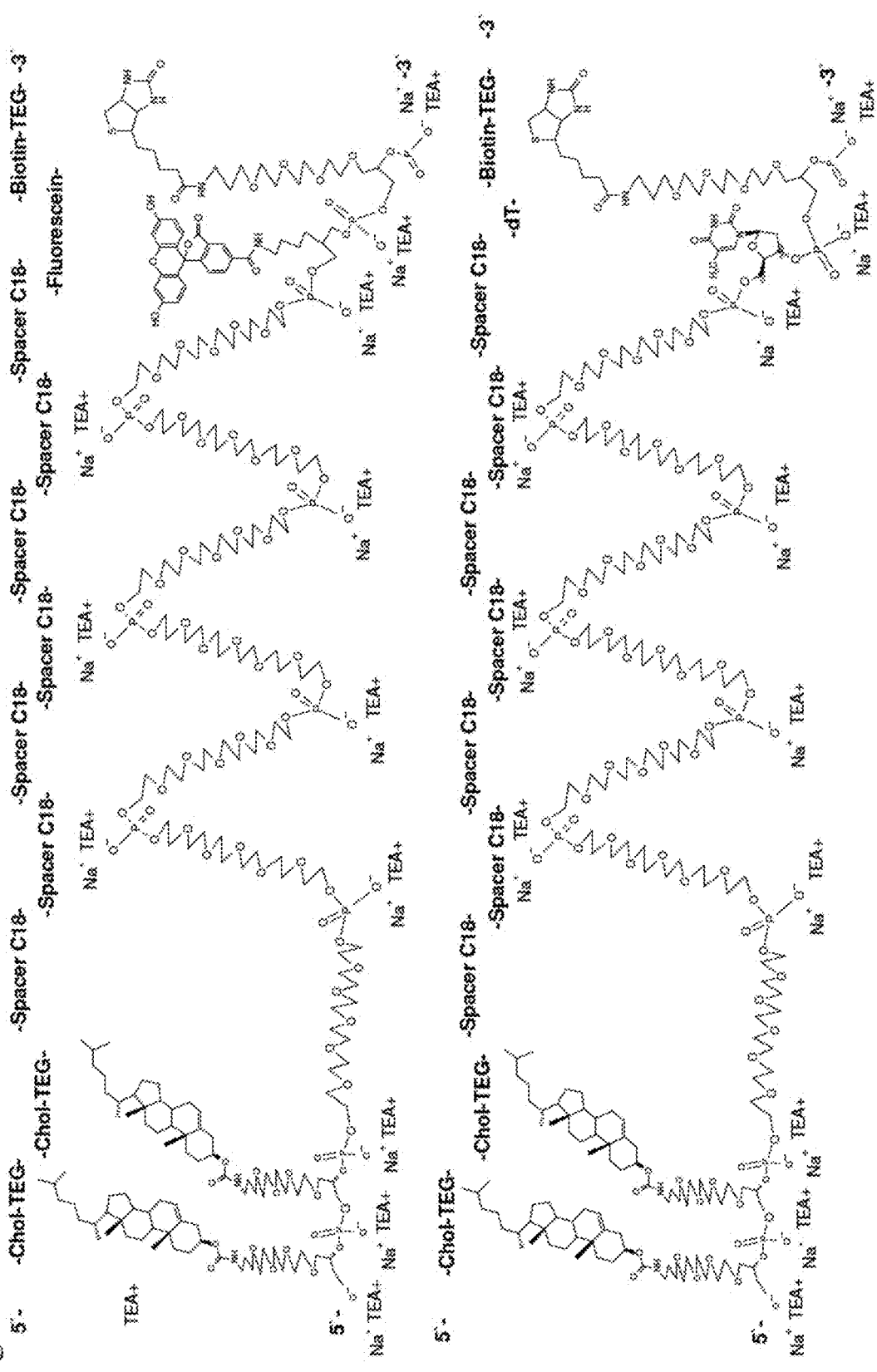
FIG. 6A: The chemical structures of exemplary compounds for use according to the invention.

According to the present invention, the compound "Cholesteryl-TEG-Cholesteryl-TEG-(SpacerC18)7-Fluos-Biotin-TEG" as shown in FIG. 6A) is understood as a compound wherein two cholesterol moieties as hydrophobic moieties are bound to a trifunctional moiety via TEG (tetraethylenglycol).

In accordance with FIG. 6, which shows the modular description of the compounds for use according to the invention in parallel to the chemical formula, "(SpacerC18)" is understood as PEG moiety of a length of 18 atoms followed by a phosphate moiety as spacer moiety. -(SpacerC18)7- is accordingly understood as a moiety consisting of 7 "(SpacerC18)" moieties.

According to the present invention "Fluos" is understood as fluorescein moiety bound directly to a trifunctional moiety A2.

According to the present invention "Biotin-TEG" is understood as biotin moiety bound via a linker TEG to a trifunctional moiety A2.

In case of the compounds for use according to the invention disclosed in this schematic way, the trifunctional moiety A1 typically is glycerol for TEG bound-hydrophobic moieties (see FIG. 6A). In addition, embodiments with serinol or 6-[(2-hydroxyethyl)amino]-1-Hexanol replacing glycerol as trifunctional moiety are equally disclosed. Other alternatives for such trifunctional moieties are available to the skilled artisan.

The trifunctional moiety A1 is serinol for the compound of FIG. 6A, wherein the hydrophobic moieties are bound directly to a trifunctional moiety A1.

In an even more schematic way, "Cholesteryl-TEG-Cholesteryl-TEG-(SpacerC18)7-Fluos-Biotin-TEG" can be described to be of the structure "5'-XXYYYYYYYFZ-3'", wherein Y=is a PEG+spacer moiety, X is a hydrophobic moiety bound to the hydrophilic moiety via a trifunctional linker, F is a fluorescent label fluorescein, and Z is a linking group (biotin). 5' and 3' indicate the direction of synthesis by an automated synthesis as shown in the Examples in analogy to nucleotides.

Analogously, -PEG2000- is understood as a PEG2000 moiety; i.e. a polyethylenglycole (PEG) chain consisting of 45 $C_2H_6O_2$ subunits.

In the compounds for use according to the invention described in the experimental part, L1 is present (n=1) and is phosphate if not explicitly indicated otherwise.

"Spacer" in the context of specifically disclosed compounds for use according to the invention in the Examples is understood as PEG-moiety including a phosphate moiety. The length of the PEG moiety is determined by e.g. C9 or C12, which indicates that the PEG moiety has a length of 9 or 12 atoms, respectively.

Figure 6B:
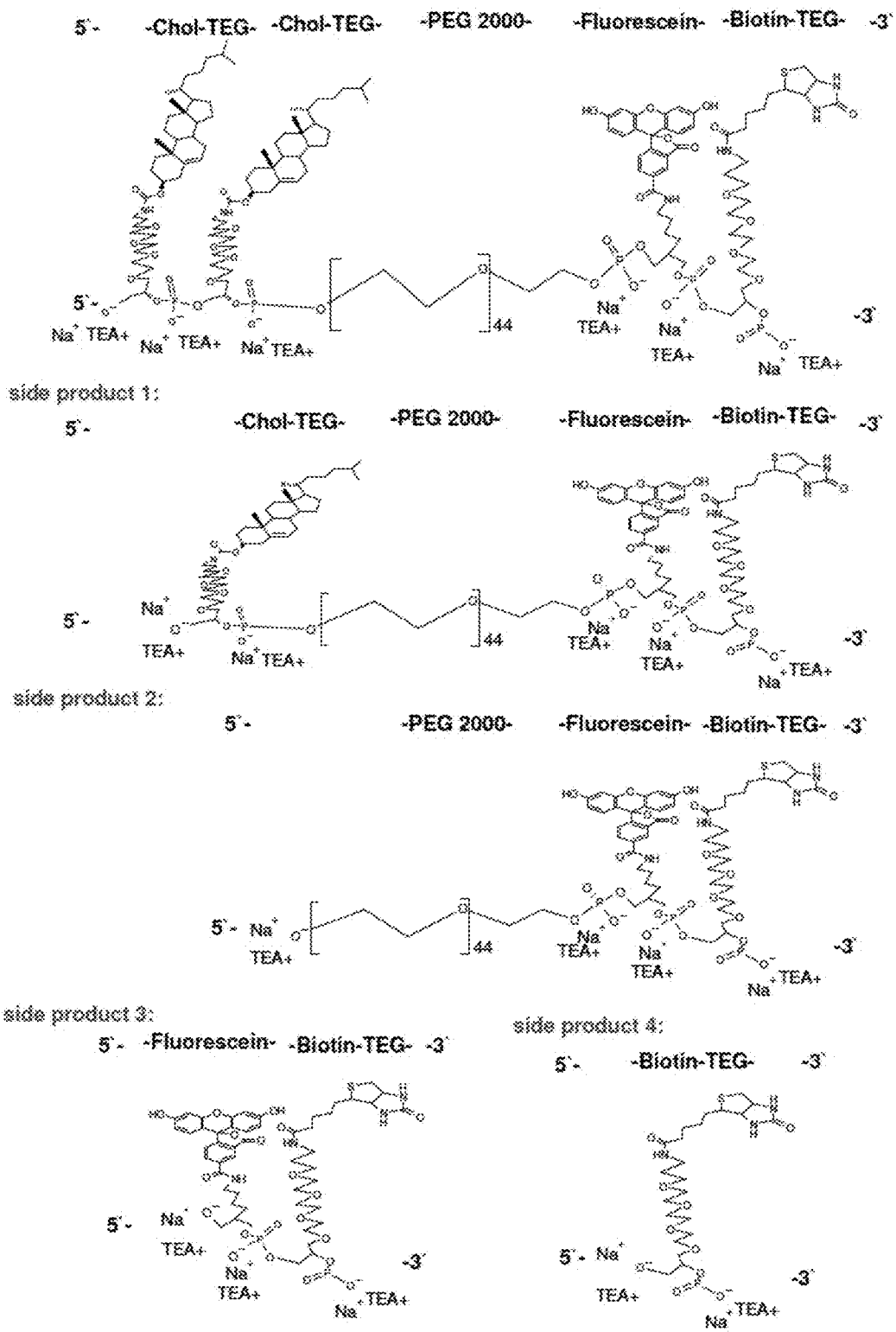
FIG. 6B: The chemical structures of side products of the synthesis from FIG. 6A.

"dT" is understood as thymidine, as exemplified in FIG. 6B). This moiety dT can be used for determining the concentration of the compounds by absorption and is a bifunctional moiety according to the present invention.

Moreover, compounds for use according to the invention containing 2 or 3 hydrophobic molecules covalently bound to the hydrophilic domain exhibit a tight binding of cells, potentially utilizing a cooperative binding effect. The binding of such molecules to cells is 100-1000 fold stronger compared to binding using a compound containing only one hydrophobic molecule.

Furthermore, it is preferred in one embodiment, that the 2, 3 or more, in particular 2 or 3 hydrophobic moieties are separated spatially by using linker moieties L1.

In such preferred embodiment, n=1, and L1 is therefore present.

The hydrophilic domain of compounds for use according to the invention comprises a PEG moiety and is therefore flexible.

The terminal hydrophobic part(s) of the compounds for use according to the invention is followed by a long flexible hydrophilic domain.

This hydrophilic domain allows a flexible folding around the cells of interest required for safe embedding of cells, thereby generating a cell-friendly, hydrogel-like environment which is important for keeping the cell morphology and functions alive, thereby stabilizing cells.

It is possible to use different linear PEG moieties, which differ in length and/or in comprising Spacer moieties like phosphate between PEG moieties in order to achieve a flexible hydrophilic domain. For example a polyethylenglycole (PEG) chain consisting of 45 $C_2H_6O_2$ subunits (PEG2000) (see Example 6 B)) or PEG-moieties with phosphate spacers like -(SpacerC18)7- as described above may be used.

Suitable protecting groups are known in the art. Suitable protecting groups for phosphoramidite chemistry are for example (4,4'-dimethoxytrityl (DMT), and fluorenomethoxycarbonyl (Fmoc). A particularly preferred protecting group is DMT (4,4'-dimethoxytrityl).

Various salts of compounds for use according to the invention can be used like Na$^+$ and/or TEA$^+$ salts of compounds for use according to the invention, as shown in FIG. 1.

Also other salts are possible and are known to a skilled person. Preferably, salts are used which do not affect or not substantially affect cell viability or function.

In a preferred embodiment of the present invention, the moiety Z has the following structure:

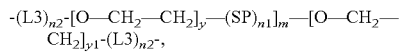

wherein

SP is a spacer moiety, each spacer moiety SP is selected independently from each other, each n1 is either 0 or 1, selected independently for each m moieties, each n2 is either 0 or 1, selected independently of each other, m is an integer from 1 to 100, preferably 1 to 50, more preferably 4 to 30, y is an integer from 1 to 100, preferably 1 to 50, more preferably 4 to 30, y1 is an integer from 0 to 30, preferably 0 to 10, more preferably 0 to 4, with the proviso that y*m+y1≤100 and wherein L3 is as defined above.

In a further preferred embodiment of the present invention, n1 is identical for the m moieties —[O—CH$_2$—CH$_2$]$_y$—(SP)$_{n1}$]—.

As can be seen from the examples, n1 is typically either always 0 in compounds for use according to the invention, or always 1 in compounds for use according to of the invention.

An exemplary compound wherein n1=1 is Cholesteryl-TEG-SpacerC12-Cholesteryl-TEG-(SpacerC18)7-Fluos-Biotin-TEG.

An exemplary compound wherein n1=0 is Cholesteryl-TEG-Cholesteryl-TEG-PEG2000-Fluos-Biotin-TEG.

In a further preferred embodiment of the present invention, y1 is 0.

An exemplary compound where y1=0 is Cholesteryl-TEG-SpacerC12-Cholesteryl-TEG-(SpacerC18)7-Fluos-Biotin-TEG.

In a further embodiment of the present invention, y1 is 1.

An exemplary compound where y1=1 is 5'-CholesterylTEG-CholesterylTEG-(SpacerC18)7-SpacerC3-dT-BiotinTEG-3'.

In a further preferred embodiment of the present invention, y is 3, 4, 5, or 6, and n1 is 1. Even more preferably m is 3, 4, 5, 6, 7, 8, 9 or 10.

In a further preferred embodiment of the present invention, the spacer moieties SP are independently from each other selected from the group consisting of a phosphate, and a bifunctional moiety.

It is preferred that all spacer moieties SP are the same. Even more preferably, all moieties SP are phosphate.

A bifunctional moiety according to the present invention is understood as moiety containing two functional groups prior to the synthesis of a compound for use according to of the invention. Such bifunctional moiety is therefore suitable for synthesis of linear compounds. Suitable bifunctional groups are preferably selected from the group consisting of a phosphate group, carbamate group, amide group, a moiety comprising a nucleobase, even more preferably dT, and a linear alkyl group having 1 to 10 C atoms, in particular 1, 2, 3, 4, 5, 6, 7, 8, 9 or 10 atoms, and which alkyl chain contains functional groups at the terminal C-atoms, in particular independently selected from amine, carbonyl, hydroxyl, thiol, carbonic acid groups. Examples of suitable linear alkyl groups with terminal functional groups are diaminoalkyl moieties such as H$_2$N—(CH$_2$)$_5$—NH$_2$ or hydroxyl-carbonyl moieties such as —C(O)—(CH2)$_4$—O—.

A trifunctional moiety according to the present invention is understood as moiety containing three functional groups prior to the synthesis of a compound for use according to the invention. Such trifunctional moiety is therefore suitable for synthesis of a branched compound. Suitable trifunctional moieties are preferably selected from a trifunctional moiety having 1 to 10 C atoms, in particular 1, 2, 3, 4, 5, 6, 7, 8, 9 or 10 C atoms and comprising at least one —OH, —SH and/or at least one —NH2 group, more preferably selected from an amino acid, such as lysine or serine, serinol, —O—CH2—CH((CH$_2$)$_4$—NH$_2$)—CH2—, glycerol, and a 1,3 diaminoglycerol moiety.

In a further preferred embodiment of the present invention, X1 and/or X2, preferably X1 or X2 is replaced by a hydrophobic domain. In such embodiment, k1+k2 may be 1. An exemplary compound wherein X1 is replaced by a hydrophobic domain is Biotin-PEG-Lys-(C18)2 as shown in the Examples.

In a further preferred embodiment of the present invention, n2 is both 0. In such embodiment, the central linear PEG moiety is directly bound to the moieties X1-[A1-(L1)n]k1 and [A2-(L1)n]k2-X2.

In a further preferred embodiment of the present invention, one or both n2=1, and L3 is an alkyl group with 1 to 10 C atoms which optionally contains an amide group, carbonyl group, carbamate, and/or NH group In a further preferred embodiment of the present invention, L3 is an alkyl group with 1 to 10 C atoms which optionally contains an amide group, carbonyl group, carbamate, and/or NH group. For example one L3 may be —NH—CH$_2$—CH$_2$NHCO—CH$_2$—CH$_2$— as in the compound Biotin-PEG2000-Lys-(C18)$_2$ of the invention.

In a further preferred embodiment of the present invention, the linear lipid is
(a) a saturated or unsaturated fatty acid, and/or
(b) a fatty acid having from 8 to 26 C atoms, preferably from 12 to 22 C atoms, more preferably from 14 to 18 C atoms.

A fatty acid is a carboxylic acid with a long aliphatic tail (chain), which is either saturated or unsaturated. Most naturally occurring fatty acids have a chain of an even number of carbon atoms, from 4 to 28.

Examples of saturated fatty acids are caprylic acid, capric acid, lauric acid, myristic acid, palmitic acid, Stearic acid, arachidic acid, Behenic acid, lignoceric acid, and Cerotic acid.

Examples of suitable unsaturated fatty acids are:

| Common name | Δx | Chain length:Double bond |
|---|---|---|
| Myristoleic acid | cis-Δ9 | 14:1 |
| Palmitoleic acid | cis-Δ9 | 16:1 |
| Sapienic acid | cis-Δ6 | 16:1 |
| Oleic acid | cis-Δ9 | 18:1 |
| Elaidic acid | trans-Δ9 | 18:1 |
| Vaccenic acid | trans-Δ11 | 18:1 |
| Linoleic acid | cis,cis-Δ9,Δ12 | 18:2 |
| Linoelaidic acid | trans,trans-Δ9,Δ12 | 18:2 |

| Common name | Δx | Chain length:Double bond |
|---|---|---|
| α-Linolenic acid | cis,cis,cis-Δ9,Δ12,Δ15 | 18:3 |
| Arachidonic acid | cis,cis,cis-Δ5,Δ8,Δ11,Δ14 | 20:4 |
| Eicosapentaenoic acid | cis,cis,cis,cis,cis-Δ5,Δ8,Δ11,Δ14,Δ17 | 20:5 |
| Erucic acid | cis-Δ13 | 22:1 |
| Docosahexaenoic acid | cis,cis,cis,cis,cis-Δ4,Δ7,Δ10,Δ13,Δ16,Δ19 | |

In an even more preferred embodiment, the linear lipid is selected from the group consisting of oleic acid, myristic acid, stearic acid and behenic acid, more preferably selected from myristic acid and oleic acid.

A hydrophobic vitamin is a small molecule selected from the group consisting of vitamins A, D, E, and K. In a more preferred embodiment, the hydrophilic vitamin is α-tocopherol. An exemplary compound for use according to the invention comprising α-tocopherol is 5'-α-TocopherolTEG-PEG2000-Fluos-3'.

In a further preferred embodiment a steroid can be used as hydrophobic moiety.

A steroid is a type of organic compound that contains a characteristic arrangement of four cycloalkane rings that are joined to each other. The core of steroids is composed of seventeen carbon atoms bonded together that take the form of four fused rings: three cyclohexane rings (designated as rings A, B and C) and one cyclopentane ring (the D ring). The steroids vary by the functional groups attached to this four-ring core and by the oxidation state of the rings. Sterols are special forms of steroids, with a hydroxyl group at position-3 and a skeleton derived from cholestane.

In a further preferred embodiment of the present invention,
(a) the steroid is a sterol, or
(b) the steroid is selected from the group consisting of cholesterol; a steroid hormone, preferably a gonadal steroid, more preferably an androgen, such as an anabolic steroid, androstenedione, dehydroepiandrosterone, dihydrotestosterone, or testosterone, an estrogen, such as estradiol, estriol, or estrone; a progestagen, such as progesterone or a progestine, a corticosteroid, particularly a glucocorticoid or a mineralcorticoid; an ecdysteroid such as ecdysterone; a phytosterol; a brassinosteroid; a hopanoid; and an ergosterol,
more preferably the steroid is cholesterol, or
(c) the hydrophobic vitamin is α-tocopherol.

In a further preferred embodiment of the present invention, two, three or four, preferably two or three hydrophobic domains are covalently bound to the hydrophilic domain.

In a further preferred embodiment of the present invention, the two or more hydrophobic domains covalently bound to the hydrophilic domain are different or identical.

In a further preferred embodiment of the present invention, the hydrophobic domains consist of a linear lipid, a steroid or a hydrophobic vitamin.

In a further preferred embodiment of the present invention, the hydrophobic domains comprise, preferably consist of a linear lipid, a steroid or a hydrophobic vitamin covalently bound to a trifunctional moiety A1 via a linker moiety L2.

Such bifunctional and trifunctional moieties were successfully employed in the compounds for use according to the invention for binding the hydrophobic moieties either directly or via a linker L2.

The linker L2 is independently any linker moiety suitable for covalently binding the hydrophobic moiety to the hydrophilic moiety, and which linker has a length of 50, 30 or 20 atoms or less between the hydrophobic moiety and A1 or A2, respectively.

In one preferred embodiment, linker L2 comprises, preferably consists of, a phosphate group, a moiety —[O—CH$_2$—CH$_2$]$_{y2}$—(SP)$_n$]$_{m1}$—, wherein SP and n are as defined above, preferably n=0, y2 is an integer from 1 to 30, preferably 3 to 10, and m1 is an integer from 1 to 10, preferably 1 to 3, a glycerol moiety, a carbamate group, an amide group, a linear alkyl group having 1 to 10 C atoms, in particular 1, 2, 3, 4, 5, 6, 7, 8, 9 or 10 atoms, and which alkyl chain contains functional groups at the terminal C-atoms, in particular independently selected from amine, carbonyl, hydroxyl, thiol, carbonic acid groups which is optionally substituted by 1, 2, 3, 4 or 5 moieties R1, wherein R1 is independently a C1-C4 alkyl, a C1-C4 hydroxyalkyl, C1-C4 aminoalkyl, a C1-C4 cyanoalkyl, a hydroxyl, a thiol, an amino or a carbonyl moiety. Examples of suitable linear alkyl groups with terminal functional groups are diaminoalkyl moieties such as H$_2$N—(CH$_2$)$_5$—NH$_2$ or hydroxylcarbonyl moieties such as —C(O)—(CH2)4—O—. Preferably, the linear alkyl group is unsubstituted. Even more preferably, the linear lipid, steroid or hydrophobic vitamin is bound to a trifunctional moiety A1 via a linker moiety —(O—CH2—CH2)j-, wherein j is selected from 1, 2, 3, 4, 5, 6, 7, 8, 9 or 10, preferably j is 3, in particular tetraethylenglycol (TEG), a phosphate moiety or a moiety comprising a TEG, glycerol, and a phosphate moiety, or a moiety comprising or consisting of -TEG-glyceryl-phosphate-O—(CH$_2$)$_4$—C(O)—.

In a more preferred embodiment, the compounds for use according to the invention comprise a linear lipid, a steroid or a hydrophobic vitamin covalently bound to a trifunctional moiety A1 via a linker moiety L2, preferably wherein L2 is selected from the group consisting of a phosphate, amide, carbamate, an ester group and a moiety —[O—CH$_2$—CH$_2$]$_{y2}$—(SP)$_n$]$_{m1}$—, wherein
SP and n are as defined above, preferably n=0,
y2 is an integer from 1 to 30, preferably 3 to 10, and
m1 is an integer from 1 to 10, preferably 1 to 3,
more preferably wherein the linear lipid, steroid or hydrophobic vitamin is bound to a trifunctional moiety A1 via the linker moiety tetraethylenglycol (TEG) or phosphate.

In a further preferred embodiment of the present invention, k1 is 1, 2 3, 4 or 5 preferably 1, 2 or 3.

In a particularly preferred embodiment of the present invention, the hydrophobic domains are covalently bound to said hydrophilic domain only via the trifunctional moietys A1 or via the domain X1-[A1-(L1)$_n$]$_{k1}$ described above. For such embodiments, the further preferred embodiments of the compounds for use according to the invention also apply. In such compounds, the hydrophobic domains are exclusively localized on one terminal part of the molecule, whereas further groups like linking groups or label moieties, if present, are localized on the other terminal part, spatially separated therefrom.

In a further preferred embodiment of the present invention, k2 is 1, 2 3, 4, 5, or 6 preferably 1, 2 or 3.

In case the compound for use according to the invention comprises a dT moiety as bifunctional moiety A2, k2 is preferably 3, 4, 5, or 6.

In another preferred embodiment of the invention, k1 is 0, and X1 is replaced by a hydrophobic domain, which preferably comprises a steroid, more preferably cholesterol. In a particularly preferred embodiment, Z is a moiety -(L3)$_{n2}$-TEG (L3)$_{n2}$-, wherein n2 is independently 0 or 1. In an even more preferred embodiment of the present invention, k2 is 1, 2 3, 4, 5, or 6 preferably 3, 4, 5 or 6. One or more, in particular one, further hydrophobic moiety(ies) are bound to moiety -[A2-(L1)n]k2-X2, wherein the further hydrophobic moiety(ies) comprises a steroid, more preferably cholesterol. Even more preferably, L2 is a linker moiety tetraethylenglycol (TEG), phosphate or a moiety comprising a TEG, glycerol, and phosphate moiety or a moiety comprising or consisting of -TEG-glyceryl-phosphate-O—(CH2)4—C(O)—. An exemplary compound for use according to the invention is Chol-TEG-Chol-TEG-Doubler-Biotin-dT shown in FIG. 12.

In case a compound for use according to the invention comprises a dT moiety as bifunctional moiety A2, k2 is preferably 3, 4, 5, or 6.

In a further preferred embodiment of the present invention, the compound for use according to invention further comprises a label moiety and/or a linking group.

In a yet even further preferred embodiment of the present invention, the compound further comprises a label moiety.

Such compounds are in addition useful for cell labelling purposes. An exemplary compound for use according to the invention is 5'-CholesterylTEG-CholesterylTEG-PEG2000-Fluos-3'.

In one such preferred embodiment, the compound does not further contain a linking group.

In another even further preferred embodiment of the present invention, the compound further comprises a linking group. An exemplary compound is 5'-CholesterylTEG-CholesterylTEG-PEG2000-BiotinTEG-3.

In a preferred embodiment, the compound does not further contain a label moiety.

In another more preferred embodiment of the present invention, the compound further comprises a label moiety and a linking group.

Such compounds are in particular suitable for applications where in addition to stabilization both immobilization and detection of cells is to be achieved, e.g. for localization of immobilized cells or for quantification of cells. An example of such compound is 5'-(Cholesteryl-TEG)2-PEG2000-Fluos-Biotin_TEG-3', which was successfully used to immobilize cells to a streptavidin-coated plate and to detect these cells.

Suitable label moieties are moieties suitable for in vitro detection and are known to a skilled person. The detection may be direct, as in the case of luminescence, in particular fluorescence, or indirect in case of an enzyme or substrate thereof. Thus, both label moieties suitable for indirect or indirect detection may be employed.

"Label" or "label moiety" as used herein refers to any substance that is capable of producing a signal for direct or indirect detection. The label moiety thus may be detected directly or indirectly. For direct detection, a label moiety suitable for use in the present invention can be selected from any known detectable marker groups, like chromogens, chemiluminescent groups (e.g. acridinium esters or dioxetanes), electrochemiluminescent compounds, dyes, or fluorescent dyes (e.g. fluorescein, coumarin, rhodamine, oxazine, resorufin, cyanine and derivatives thereof), luminescent metal complexes, such as ruthenium or europium complexes and radioisotopes.

In indirect detection systems, a first partner of a bioaffine binding pair is a label moiety of the compounds for use according to the invention; i.e. a first partner is covalently bound to and part of the compound for use according to the invention. Examples of suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g. steroid hormone receptor/steroid hormone. Preferred first binding pair members comprise hapten, antigen and hormone. Also preferred are haptens like a tag, digoxin and biotin and analogues thereof. The second partner of such binding pair, e.g. an antibody, streptavidin, etc., usually is labeled to allow for direct detection, e.g. by the label moieties as mentioned above.

Therefore, in a preferred embodiment, the label moiety is a label moiety for direct labeling, or for indirect labeling.

In one preferred embodiment, the label moiety is selected from (a) a direct labeling moiety selected from the group consisting of a chromogen, chemiluminescent group (e.g. acridinium ester or dioxetane), an electrochemiluminescent compound, a dye, a fluorescent dye (e.g. fluorescein, coumarin, rhodamine, oxazine, resorufin, cyanine and derivatives thereof), a luminescent metal complex, such as a ruthenium or europium complex, and a radioisotope; (b) or one of the partners of an indirect detection system, preferably wherein the label moiety is one of the members of the binding pairs selected from the group consisting of (i) hapten or antigen/antibody, (ii) biotin or biotin analogues such as aminobiotin, iminobiotin or desthiobiotin/avidin or streptavidin, (iii) sugar/lectin, (iv) nucleic acid or nucleic acid analogue/complementary nucleic acid, and (v) receptor or receptor fragment/ligand, e.g. steroid hormone receptor/steroid hormone.

Preferred first binding pair members as label moieties suitable for indirect detection comprise hapten, antigen and hormone. Also preferred are haptens like digoxin and biotin and analogues thereof. The second partner of such binding pair, e.g. an antibody, streptavidin, etc., is typically labeled to allow for direct detection, e.g. by the direct label moieties as mentioned above; however, it is also possible to employ an antibody in a compound for use according to the invention and to use a labeled antigen or hapten for detection.

In the above description of binding pair members, the term antibody is understood to encompass both antibody and antigen-binding fragments thereof.

In a preferred embodiment, the label moiety is a label moiety for direct labeling, even more preferably the label moiety is a fluorescent moiety or dye.

Suitable fluorescent moieties (or dyes) are known in the art and encompass fluorescein, Cy3, Cy5, Cy5.5, Cy2, Cy3.5, Cy3b, Cy7, an Alexa Fluor dye, a xanthene derivative such as rhodamine, Oregon green, eosin, or Texas red, a cyanine derivative such as cyanine, indocarbocyanine, oxacarbocyanine, thiacarbocyanine, and merocyanine, a naphthalene derivative such as dansyl and prodan derivatives, a coumarin derivative, an oxadiazole derivative, such as pyridyloxazole, nitrobenzoxadiazole and benzoxadiazole, a pyrene derivatives such as cascade blue, an oxazine derivative, such as Nile red, Nile blue, cresyl violet, oxazine 170, an acridine derivatives, such as proflavin, acridine orange, acridine yellow, an arylmethine derivative, such as auramine, crystal violet, malachite green, a tetrapyrrole derivative such as porphin, phthalocyanine and bilirubin.

In the examples, fluorescein was used as representative label. This allows sensitive detection of a label, allowing both localization of a label, and/or quantification. A fluorescent label is a particularly preferred label moiety of the invention.

Suitable radioactive isotopes or radioisotopes for labeling and methods for labeling a compound for use according to the invention with such radiolabel are known to a skilled person. For example, one of the following isotopes may be used: $^{14}C$, $^{3}H$, $^{32}P$, $^{33}P$, $^{123}I$, $^{125}I$, and $^{131}I$.

In case an antibody or antigen-binding fragments are used as members of the indirect system antibody/antigen or hapten, either an antibody or antigen-binding fragment specific for the epitope or hapten may be part of the compound for use according to the invention, or the epitope or hapten may be part of the compound for use according to the invention. Accordingly, the respective other member may be labeled directly, e.g. with a fluorescent label for subsequent detection. Suitable antibodies or antigen-binding fragments are described below in more detail.

In a preferred embodiment of the invention, a linking group and/or label is bound to the moiety $[A2-(L1)_n]_{k2}$-X2.

In a particularly preferred embodiment of the present invention, the hydrophobic domains are covalently bound to said hydrophilic domain only via the trifunctional moiety(s) A1 (or via the domain X1-$[A1-(L1)_n]_{k1}$ described above), and a linking group and/or label moiety is bound to the moiety $[A2-(L1)_n]_{k2}$-X2. This ensures spatial separation of the hydrophobic domains for insertion into a cell membrane, and the moieties for immobilization and/or labelling, if present.

Such compounds are in addition to stabilization also suitable for immobilization in case a linking group is present.

Such compounds are in addition to stabilization also suitable for labelling and detection in case a label moiety is present.

In a further particularly preferred embodiment of the present invention, the hydrophobic domains are covalently bound to said hydrophilic domain only via the trifunctional moiety(s) A1 (or via the domain X1-$[A1-(L1)_n]_{k1}$ described above), and a linking group and a label moiety is bound to the moiety $[A2-(L1)_n]_{k2}$-X2.

Such compounds in addition to stabilization further allow both immobilization and labelling, detection and quantification.

In a yet further particularly preferred embodiment of the present invention, the hydrophobic domains are covalently bound to said hydrophilic domain only via the trifunctional moiety(s) A1 (or via the domain X1-$[A1-(L1)_n]_{k1}$ described above), and a linking group, but not a label moiety is bound to the moiety $[A2-(L1)_n]_{k2}$-X2.

Such compounds can be used if only immobilization or only and labelling, detection and/or quantification of cells bound is intended in addition to stabilization.

A linking group is a moiety which is suitable for reversibly or irreversibly, and/or covalently or non-covalently immobilizing a compound to a support, in particular solid support. In a preferred embodiment, the linking group is an antibody or antigen-binding antibody fragment, a receptor or a binding site thereof, a ligand to a receptor, enzyme or a binding site thereof, a substrate to an enzyme, a tag-binding site, a tag, or a functional chemical group.

A functional chemical group may be for example a thiol group which can be bound to a gold-coated substrate surface by formation of a covalent, irreversible —S—S— bond.

The binding of biotin to streptavidin or antibody or antigen-binding antibody fragment is non-covalent and reversible. Such linking groups employing non-covalent binding to a solid support are preferred in case it is intended—in addition to stabilization—to again detach cells for further use, e.g. for administration in a an animal model.

In a preferred embodiment, the linking group may be e.g. a biotin-moiety which allows the non-covalent attachment to a streptavidin-coated surface, or a thiol-group which can be bound to a gold-coated substrate surface as solid support.

In an even more preferred embodiment of the present invention, a compound for use in the invention comprises a label moiety and/or a linking group, wherein the label moiety is a fluorescent label and/or the linking group is biotin.

In an even more preferred embodiment, a compound for use according to the invention comprises a label moiety and a linking group, wherein the label moiety is a fluorescent label and the linking group is biotin.

In an even more preferred embodiment, a compound for use according to the invention comprises a linking group, which is biotin.

The term "solid support" refers to a material in the solid-phase that interacts with reagents in the liquid phase by heterogeneous reactions. The use of solid supports is well known in the fields of chemistry, biochemistry, pharmacy and molecular biology. Many types of solid supports have been developed depending on the technical problem to be solved. Any of these may be used in the context of the present invention. For example, the solid support may include components of silica, cellulose acetate, nitrocellulose, nylon, polyester, polyethersulfone, polyolefin, or polyvinylidene fluoride, or combinations thereof. Further suitable solid supports include, but are not limited to, controlled pore glass, a glass plate or slide, polystyrene, and activated dextran. In other aspects, synthetic organic polymers such as polyacrylamide, polymethacrylate, and polystyrene are also illustrative support surfaces. In addition, polysaccharides such as cellulose and dextran, are further illustrative examples of support surfaces. Other support surfaces such as fibers are also operable.

The solid support may be contained in a vessel, wherein the vessel is a tube, such as a centrifuge tube or spin tube, syringes, cartridge, chamber, multiple-well plate, or test tube, or combinations thereof. The solid support may be pre-treated or functionalized in order to allow immobilization of cells. For example, a well-plate may be pre-treated with streptavidin as shown in the examples. In one embodiment, the solid support may be fibrous or particulate usually allowing for appropriate contacting. The size of the solid support suitable for use may vary. The cells may be bound to one solid support only (e.g. one vessel or multi-well plate) or may be bound to a multitude of solid supports (e.g. beads). The shape of the solid support suitable for use may be, for example, a sheet, a precut disk, cylinder, single fiber, or a solid support composed of particulates. In one preferred embodiment, the solid support is flat, or substantially flat with cavities. In one embodiment, the solid support may be fibrous or particulate. The size of the solid support may vary and may be chosen depending from the method or application to be carried out.

In some embodiments, the solid phase is a test strip, a chip, in particular a microarray or nanoarray chip, a microtiter-plate or a microparticle.

In a more preferred embodiment, a label moiety and/or a linking group, where present is/are covalently bound via the trifunctional moiety A2, as described above.

In another embodiment, one or more moiety(s) A2 are a bifunctional or trifunctional label moiety or a linking group, more preferably a moiety A2 is a moiety comprising a nucleobase, even more preferably a moiety A2 is dT (thymidine). Such compounds comprising dT were used for determination concentration of the compound.

In a further preferred embodiment of the present invention, the linkers L1 are independently selected from the group consisting of a phosphate, amide, carbamate, and an ester group.

In a further preferred embodiment of the present invention, the moieties A1 and A2 are independently selected from a bifunctional group selected from the group consisting of a phosphate group, carbamate group, amide group, a moiety comprising a nucleobase, even more preferably dT, and a linear alkyl group having 1 to 10 C atoms and which alkyl chain contains functional groups at the terminal C-atoms, in particular independently selected from amine, carbonyl, hydroxyl, thiol, carbonic acid groups, and a trifunctional moiety having 1 to 10 C atoms and comprising at least one —OH, —SH and/or at least one —NH$_2$ group, preferably selected from lysine, serine, serinol, —O—CH$_2$—CH ((CH$_2$)$_4$—NH$_2$)—CH$_2$—, a glycerol, and a 1,3 diaminoglycerol moiety.

In a further more preferred embodiment of the present invention, the linkers L2 are independently selected from the group consisting of a phosphate, amide, carbamate, an ester group and a moiety

—[O—CH$_2$—CH$_2$]$_{y2}$—(SP)$_n$]$_{m1}$—, wherein
SP and n are as defined above, preferably n=0,
y2 is an integer from 1 to 30, preferably 3 to 10, and
m1 is an integer from 1 to 10, preferably 1 to 3.

PEG-based linkers, namely TEG-linkers were shown to be useful in the exemplary compounds for use according to the invention. An exemplary compound is 5'-CholesterylTEG-CholesterylTEG-(SpacerC18)7-Fluos-Biotin-TEG-3'.

Figure 6C:
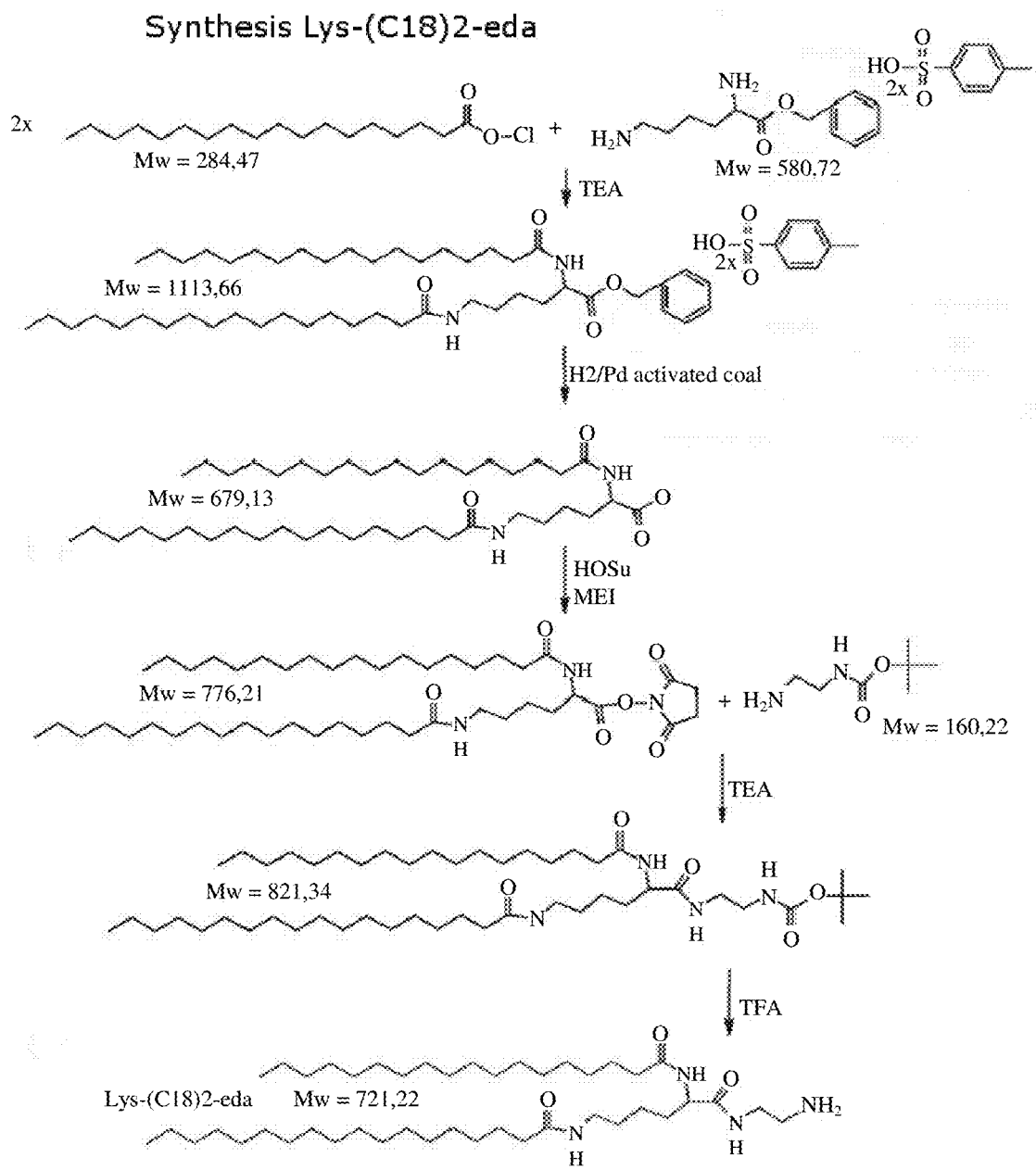
FIG. 6C: The synthesis of Biotin PEG Lys (C18) as well as side products of the synthesis.
Figure 7A:
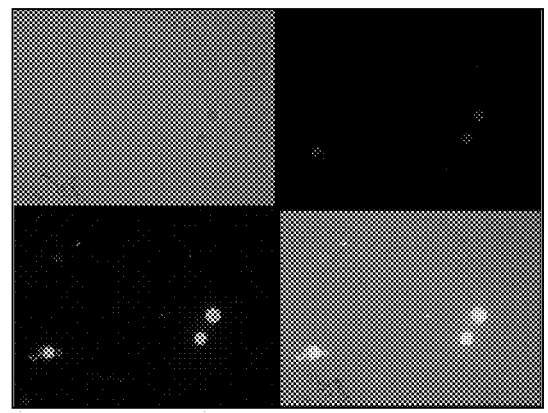
FIG. 7A: shows staining of cell with cholesteryl-containing compound with internal reference 29.891180. Representative pictures according to Example 3 throughout FIG. 7.
Figure 7B:
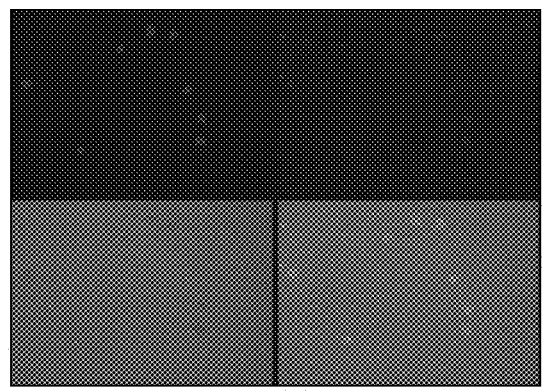
FIG. 7B: shows staining of cell with myristic acid containing compound with internal reference 29.891194.
Figure 7C:
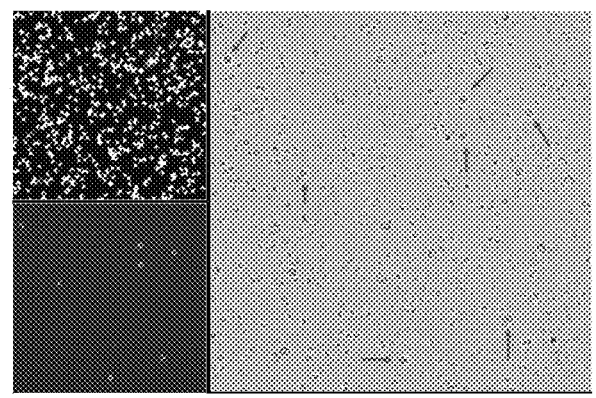
FIG. 7C: shows staining of cells with MDA-MB468.
Figure 7D:
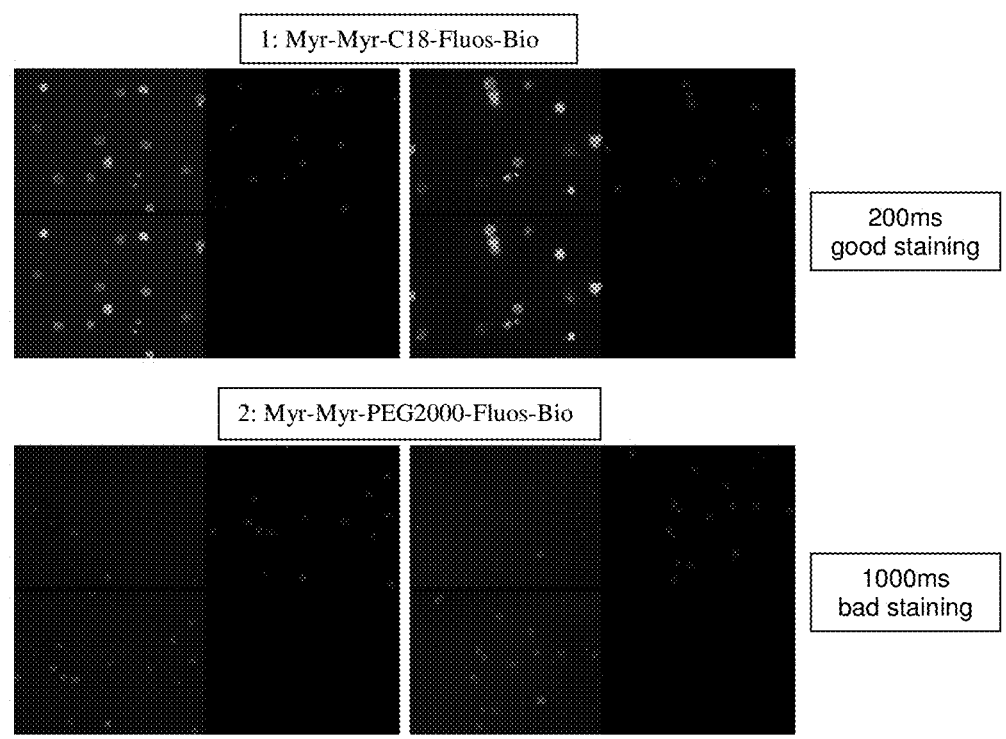
FIG. 7D: shows staining of cells staining of cells for different exposure times with different compounds indicated schematically.
Figure 7E:
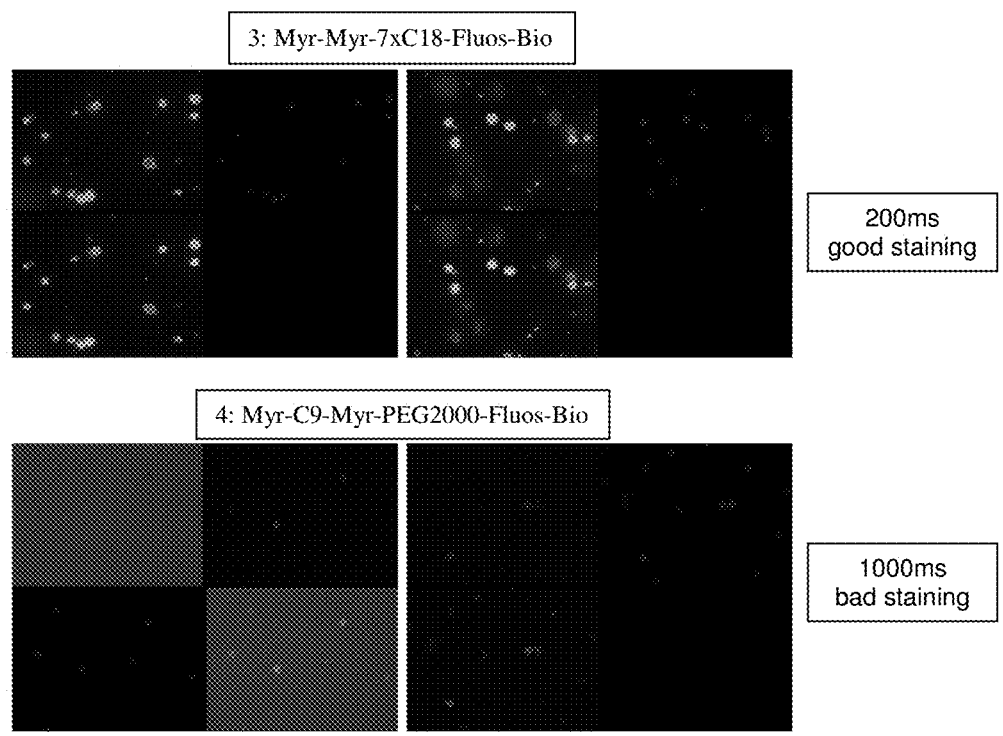
FIG. 7E: shows staining of cells staining of cells for different exposure times with different compounds indicated schematically.
Figure 8A:
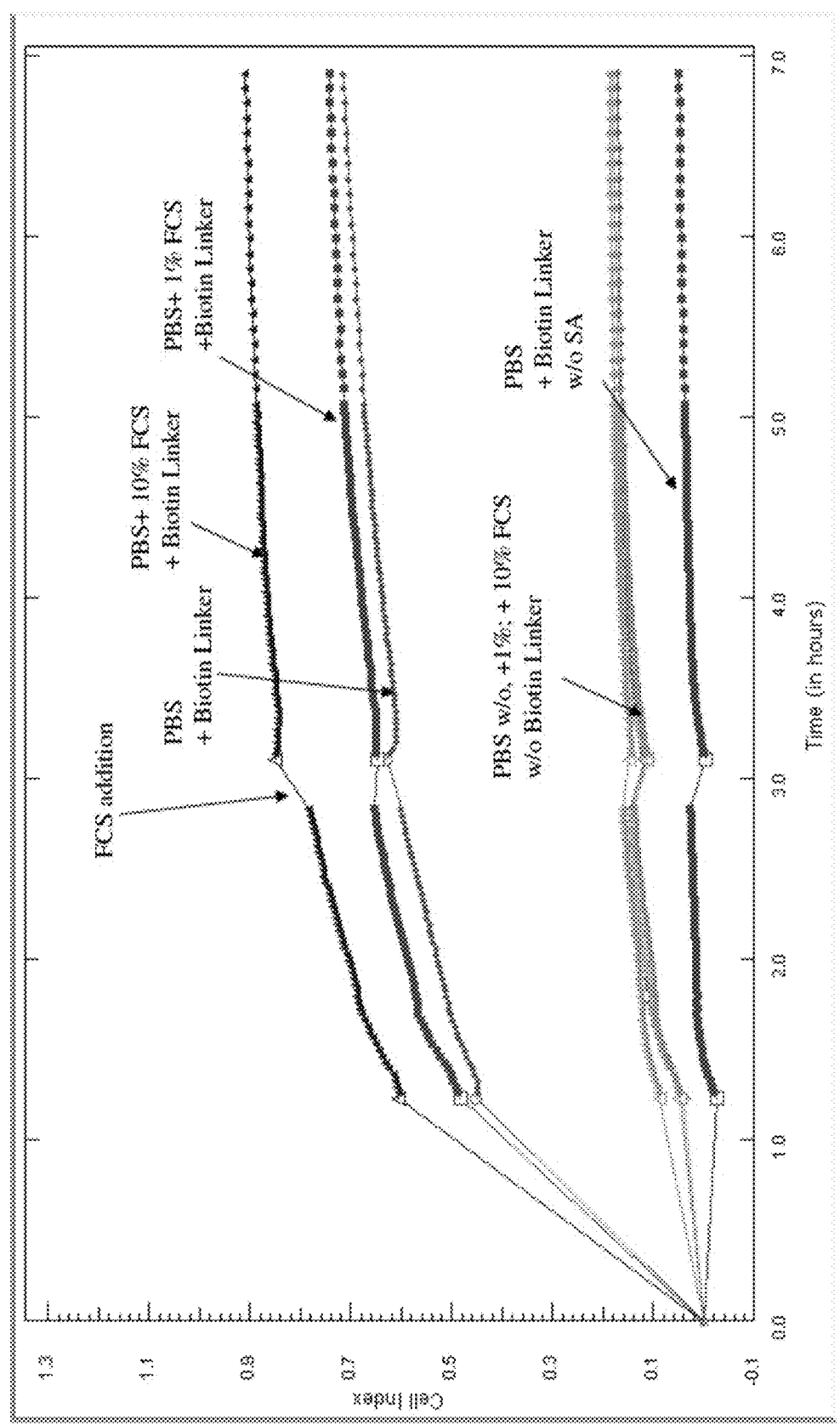
FIG. 8A: shows the results of the xCelligence experiments with Jurkat cells according to Example 3.
Figure 8B:
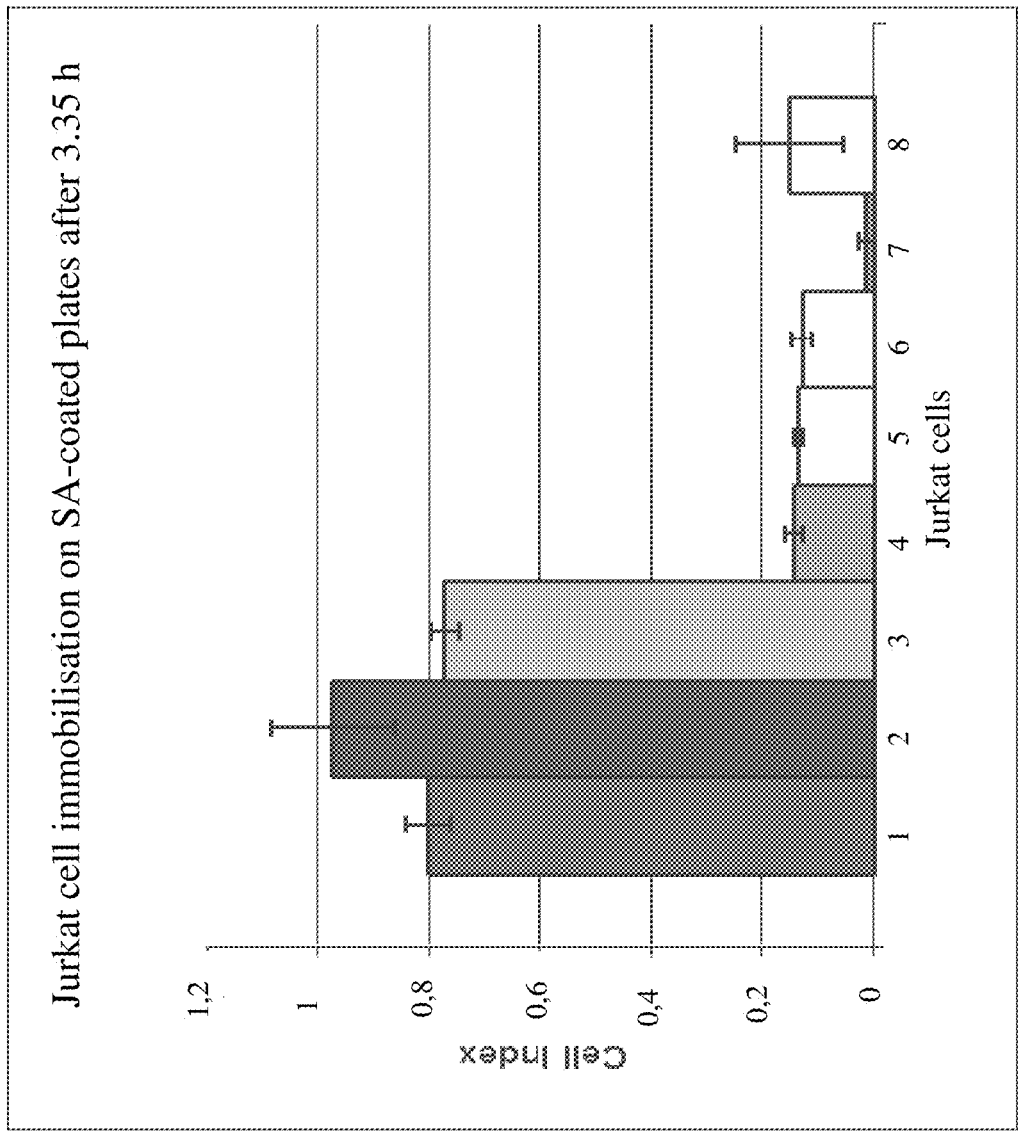
FIG. 8B: shows the results of the xCelligence experiments with Jurkat cells according to Example 3, specifically showing Jurkat cell immobilization on SA-coated plates after 3.35 hours. Column 1: PBS$_+$ Biotin Linker; Column 2: PBS$_+$10% FCS+Biotin linker; Column 3: PBS$_+$1% FCS$_+$ Biotin linker; Column 4: PBS w/o Biotin linker; Column 5: PBS$_+$10% FCS w/o Biotin linker; Column 6: PBS$_+$1% FCS w/o Biotin linker; Column 7: PBS$_+$ Biotin linker w/o SA; Column 8: PBS w/o Biotin linker w/o SA.
Figure 9A:
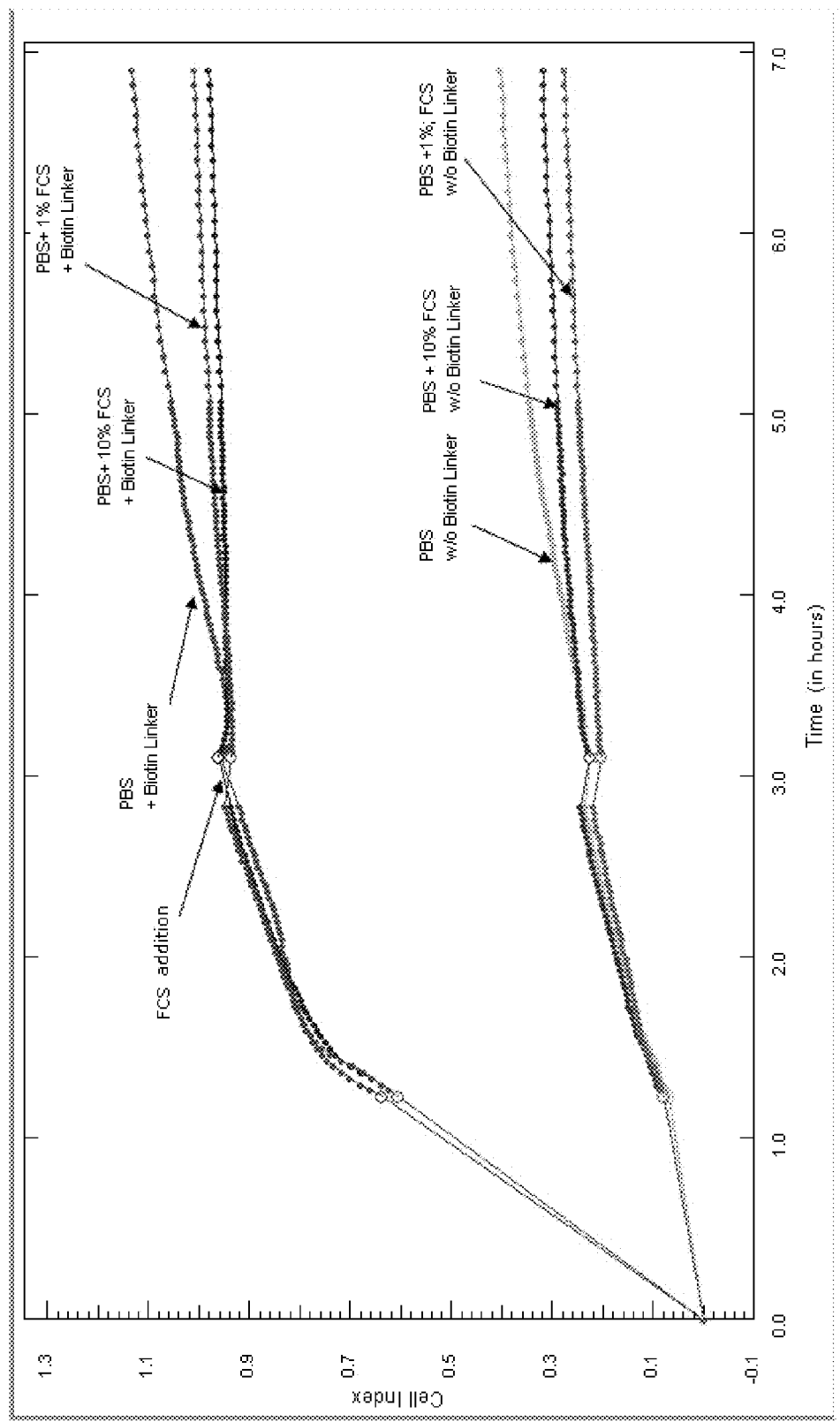
FIG. 9A: shows the results of the xCelligence experiments with WBC cells according to Example 3.
Figure 9B:
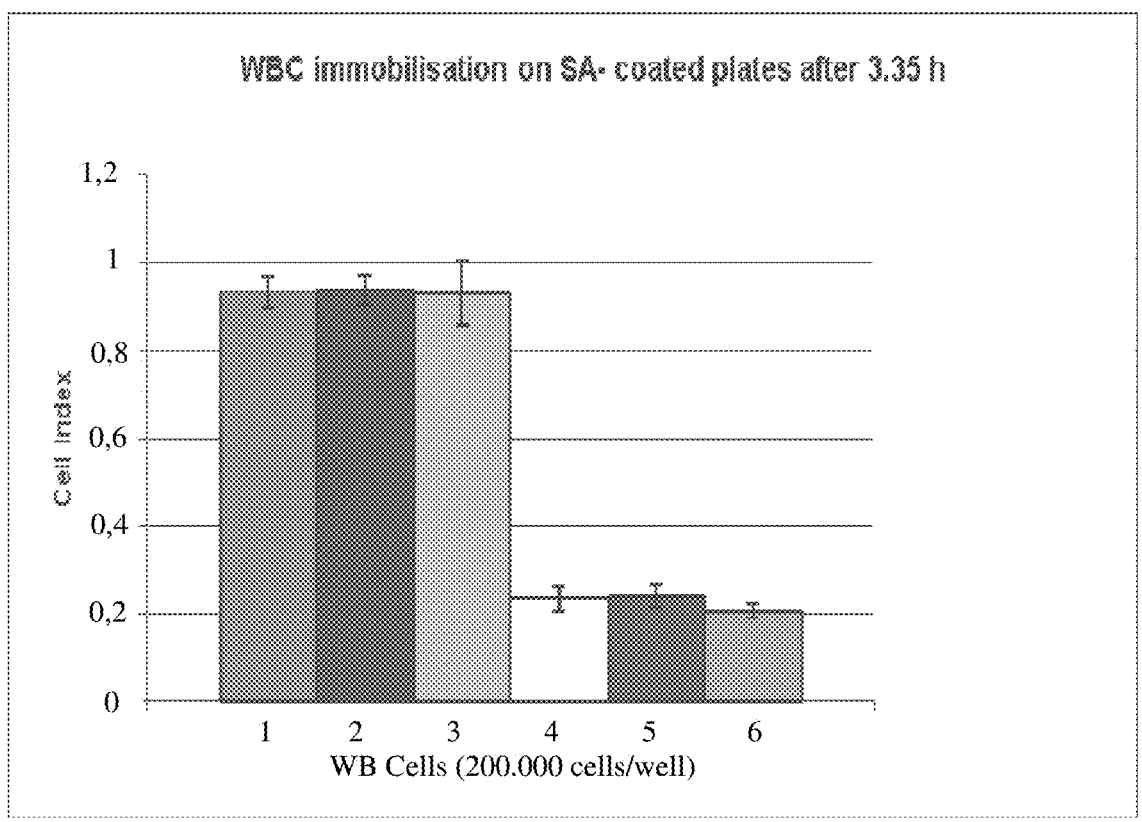
FIG. 9B: shows the results of the xCelligence experiments with WBC cells according to Example 3, specifically showing WBC immobilization on SA-coated plates after 3.35 hours. Column 1: PBS$_+$ Biotin Linker; Column 2: PBS+10% FCS$_+$ Biotin linker; Column 3: PBS$_+$1% FCS$_+$ Biotin linker; Column 4: PBS w/o Biotin linker; Column 5: PBS$_+$10% FCS w/o Biotin linker; Column 6: PBS$_+$1% FCS w/o Biotin linker.
Figure 10:
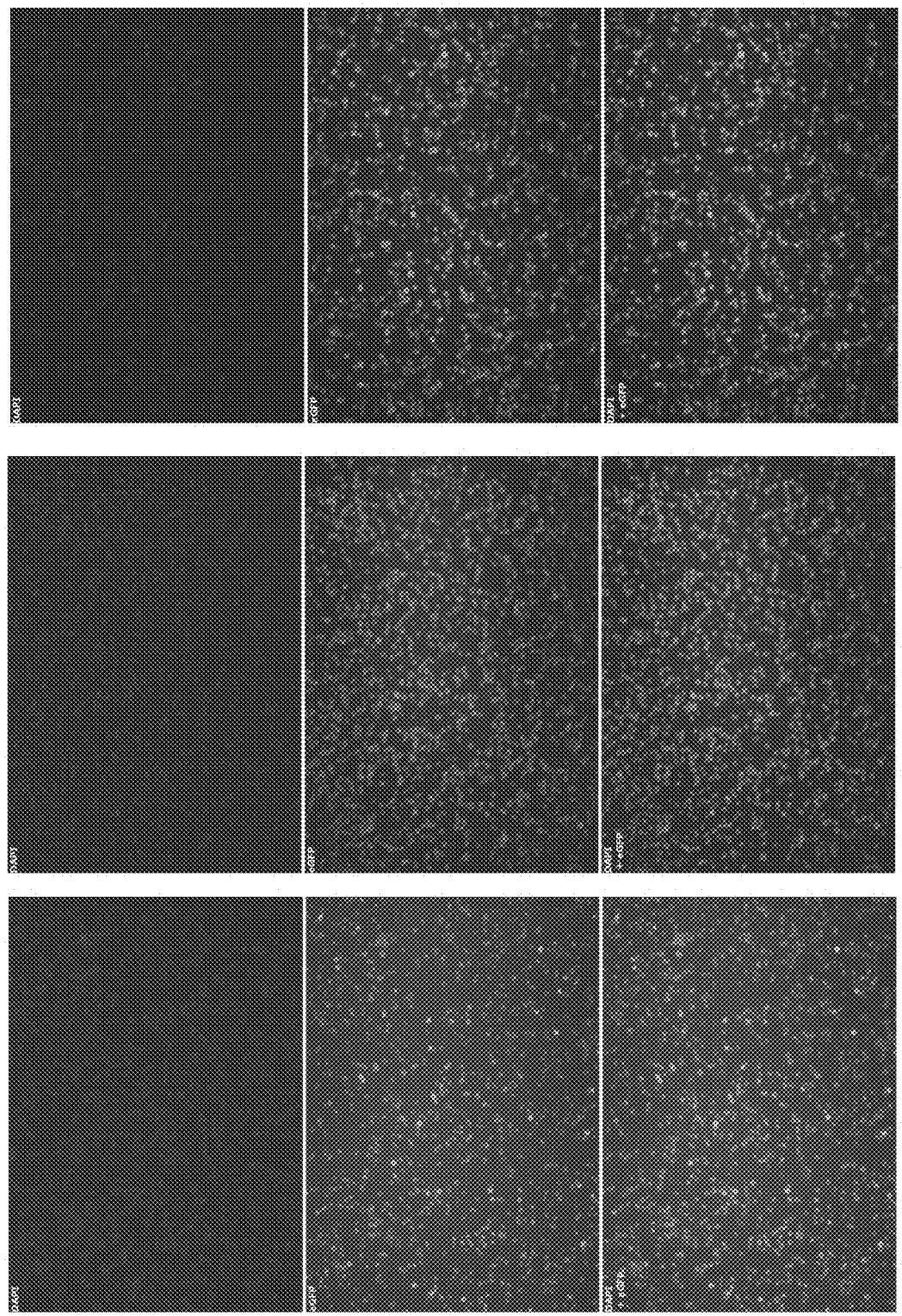
FIG. 10: shows the staining of immobilized cells, in accordance with Example 3. Left column: DA-MB468-antibody: K5/8. Middle column: MDA-MB468-antibody: EpCAM Miltenyi FITC. Right column: MDA-MB468-antibody: EGFR.
Figure 11:
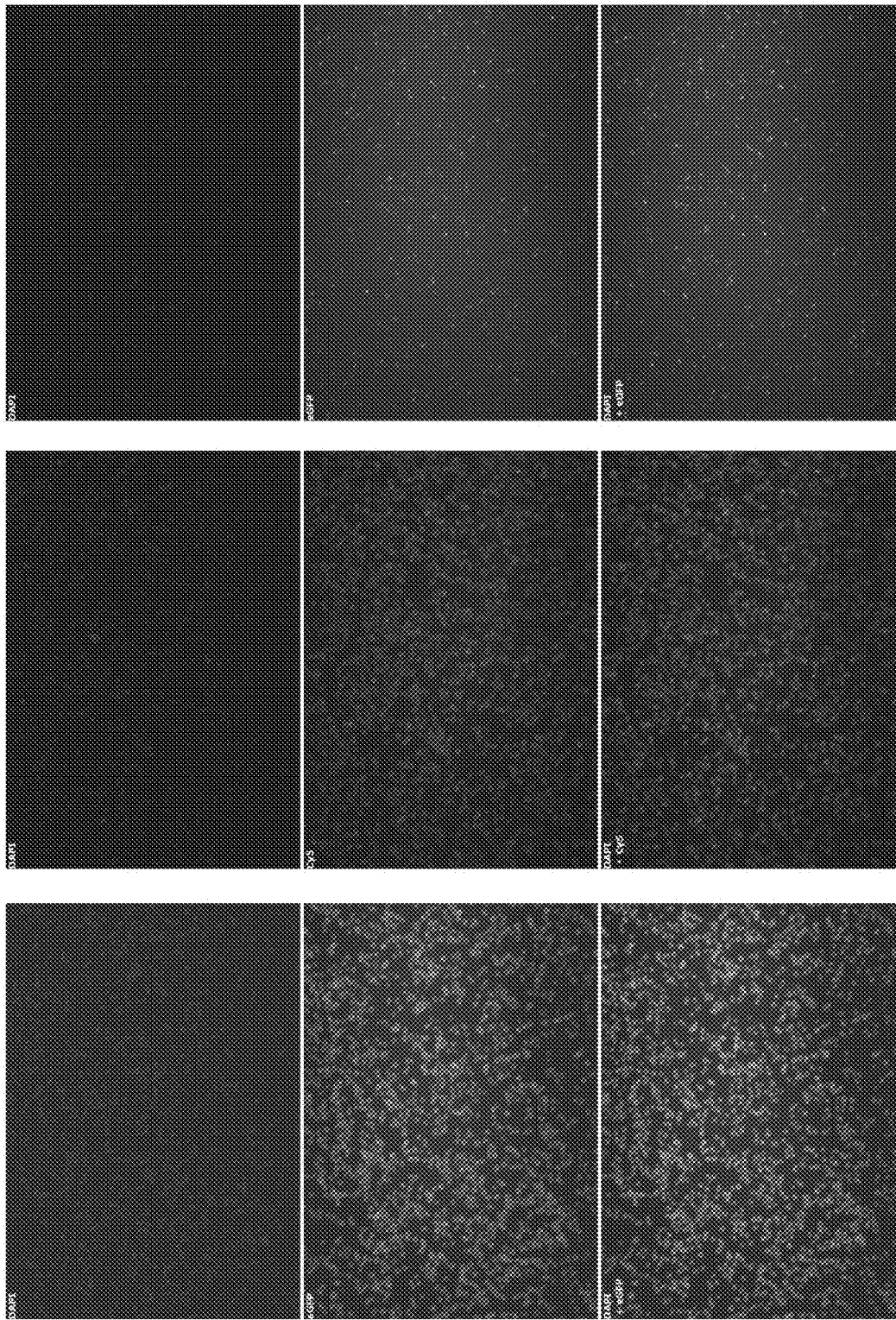
FIG. 11: shows the staining of immobilized cells, in accordance with Example 3. Left column: MDA-MB468-antibody: EpCAM Biolegend. Middle column: MDA-MB468-antibody: EpCAM Miltenys APC. Right column: WBCs-antibody: CD45 Biolegend.
Figure 13:
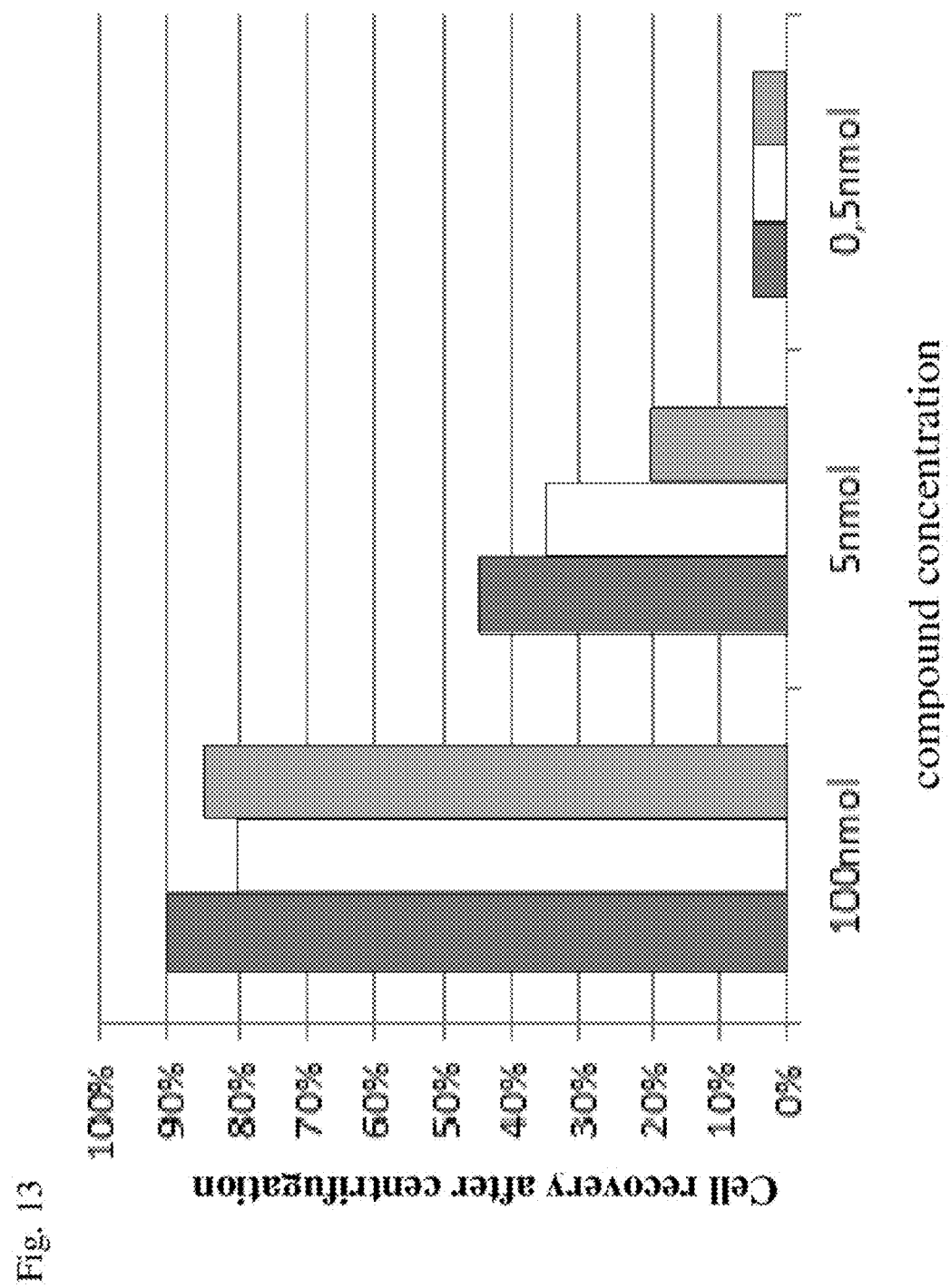
FIG. 13: shows WBC recovery rate after centrifugation and cell immobilization using different molecules. Molecule probes HH1749*, HH1750* and HH1755* (* Biotin-PEG-Lysin-(C18)2) show different performance concerning recovery rate after centrifugation: The higher the concentration of the molecule, the higher the cell recovery rate after centrifugation. Centrifugation characteristics: 10 min, 300×g.

The compounds for use according to the invention as well as the intermediates thereof can be prepared by methods known to a skilled person. An exemplary synthesis of a compound for use according to the invention is shown in FIG. 6C. Also, intermediates used in the synthesis of compounds for use according to the invention are shown in FIG. 12. Further, the general concept of the syntheses is shortly described in Example 1 for the compounds. The compounds can be prepared on solid phase analogous to the phosphoramidite-based synthesis of nucleotides. The compounds may be synthesized by synthesis on a solid support like CPG as described in the Examples. In particular, the compounds may be synthesized by subsequent coupling steps under conditions known to a skilled person, and cleavage from the solid support (in the examples: CPG (controlled pore glass)). Also other solid supports such as macroporous polystyrene may be used for synthesis. The synthesis may be performed by retaining a protecting group or by cleaving of the protecting group. In particular, the compounds may be synthesized in either DMT on or DMT off modus, leaving the DMT molecule on the end of the molecule designated as 3' end, or by cleaving off the DMT group. The compounds are optionally further purified e.g. by dialysis.

The synthesis of Biotin-PEG-Lys-(C18)2 is described in detail in FIG. 6C).

The other compounds for use according to the invention can be prepared in an analogous manner according to methods known in the art.

In a yet further embodiment the present invention relates to a composition comprising at least one compound as described above bound to at least one cell, preferably a viable cell. Such composition provides for a stabilized cell. Depending on the further presence of a label moiety and/or linking group, the composition is further useful for detection and/or immobilization of the cell, respectively.

In one preferred embodiment, such composition further comprises a solid support, to which at least one compound for use according to the invention is bound via a linking group. In such embodiment, at least one stabilized cell is immobilized to a solid support via a compound for use according to the invention. In case the compound further contains a label moiety, localization, detection and quantification of the cell(s) is possible.

In another preferred embodiment, a composition comprising at least one compound for use according to the invention bound to at least one cell comprises an aqueous, buffered solution, wherein at least one cell to which at least one compound for use according to the invention is bound, is suspended. Such compositions are suitable for adequately stabilizing the cells therein, e.g. during FACS or centrifugation.

The compounds are suitable for binding to any cells which contain a lipid bilayer. Preferably, the cells are eukaryotic cells, more preferably animal, even more preferably vertebrate cells, most preferably human cells.

In a further preferred embodiment, the cell is a white blood cell, a rare cell, a tumor cell or a mutated cell, more preferably a vertebrate or human white blood cell, rare cell, tumor cell or mutated cell.

In a further embodiment the present invention relates to the use of a composition comprising one or more compounds as described above for stabilizing a cell.

Therefore, in another embodiment, the present invention relates to the use of a composition comprising at least three different compounds which can be used according to the invention, wherein the different compounds differ at least in their hydrophobic domains for stabilizing a cell.

By using a variety of compounds for use according to the inventions of which at least two differ at least in their hydrophobic domains, a composition can be obtained which binds and stabilizes all cell types efficiently.

In an even more preferred embodiment, the composition thus comprises at least four, five, six, seven, eight, nine or ten different compounds for use according to the invention. In an even more preferred embodiment, two, three, four, five, six, seven, eight, nine, ten or all compounds of such composition differ at least in their hydrophobic domains.

Preferred hydrophobic domains which are suitable are those as defined above. For example, a composition comprising 5'-CholesterylTEG-CholesterylTEG-PEG2000-Fluos-3' can be used.

In a more preferred embodiment, one or all hydrophobic domains of at least one compound comprises, preferably consists of, a saturated fatty acid, especially myristic acid, stearic acid or behenic acid, particularly myristic acid, and/or one or all hydrophobic domains of at least one compound comprises, preferably consists of, a steroid, in particular cholesterol, or a hydrophobic vitamin, in particular α-tocopherol.

In preferred embodiment, the present invention relates to the use of an aqueous solution comprising one or more compounds for stabilizing a cell.

The aqueous solution is preferably buffered. For example a solution of the invention may be a phosphate buffered saline solution (PBS), Tris, and/or Hepes-buffered solution.

The pH of the solution of the invention is preferably about 5.5 to 8.5, more preferably 6.5 to 7.5.

In a further embodiment, the present invention relates to a method of stabilizing a cell, the method comprising:
a) providing a compound as defined above; and
b) contacting a cell with the compound under conditions allowing the interaction of the compound with the membrane of the cell, thereby stabilizing the cell, and
c) optionally applying shear forces to the cell.

In a preferred embodiment of the present invention, stabilizing is stabilizing during exposure of the cell to shear forces.

In a further preferred embodiment, stabilizing is stabilizing during exposure of the cell to shear forces by centrifugation, large scale cell cultivation, flow cytometry, fluorescence-activated cell sorting and/or bead-based cell separation.

In a further preferred embodiment, stabilizing is stabilizing during exposure of the cell to centrifugation, large scale cell cultivation, flow cytometry, fluorescence-activated cell sorting and/or bead-based cell separation.

For the compound which can be employed in such method, the same embodiments apply as for the uses described above. The provision of compounds to be used in the method of the invention is described above.

Also a composition comprising two or more compounds as described above may be used in the method of the invention. Such compositions and their use according to the invention are described above.

The compound may be contacted with the cell in step b) as aqueous solution comprising one or more compounds for use according to the invention. Such solution is suitable for pipetting or otherwise adding to the cells. The aqueous solution is preferably buffered. For example a solution of the invention may be a phosphate buffered saline solution (PBS), Tris, and/or Hepes-buffered solution or a solution containing media. The pH of the solution is preferably about 5.5 to 8.5, more preferably 6.5 to 7.5.

As stabilizing of cells is done with viable or potentially viable cells, the cells are typically present in an aqueous solution, which is preferably buffered and/or contains nutrients, e.g. the cells are suspended in PBS or media. The compound for use according to the invention may be added to the cells, e.g. in form of a solution, e.g. as aqueous solution by methods known in the art, as pipetting.

The pH of the suspension of the cells is preferably about 5.5 to 8.5, more preferably 6.5 to 7.5.

Mixing may be performed gently in order to maintain viability of the cells.

The compound is contacted with a cell in step b) of the method of the invention. Typically, more than one cell will be present and brought into contact with the compound of the invention. Therefore, the compound is preferably added to a composition comprising a plurality of cells, e.g. 2 or more, 10 more, 50 or more, 100 or more, or 1000 or more cells. Preferably such population of cells are suspension cells. Thus, a solution comprising a compound as disclosed herein may be added to a suspension of cells to be stabilized.

The population of cells may be cells of the same or different cell type. For example, a population of white blood cells encompassing different cell types may be used, as in the Examples (see Example 5).

Typically, the contacting typically takes place at a temperature of about 1° C. to 45° C., preferably, 10° C. to 30° C., more preferably 22° to 38° C.

Also, the contacting typically takes place at a pressure of about 900 to 1100 mbar in order to maintain cell viability.

Also, the cells are preferably incubated with the compounds for a sufficient time to allow for binding to the cell.

Typically, the cells are preferably incubated with the compounds for 1 minute to 3 days, preferably 5 minutes to 24 h, even more preferably for 10 minutes to 8 hours.

Moreover, the aqueous solution is typically chosen not to affect the integrity and/or viability of a cell. Therefore, the solution preferably does not contain cytotoxic compounds.

Such conditions allow the interaction of the compound with the membrane of the cell, thereby stabilizing the cell.

The stabilizing effect already occurs upon interaction, without further imposing shear stress. Thus, in one embodiment, no shear forces are applied to the cell after step b) of the method of the invention.

However, in a preferred embodiment, shear forces or shear stress are applied to the cell subsequent to step b) of the method of the invention.

In a preferred embodiment of the cell, applying shear forces to the cell is by centrifugation, large scale cell cultivation, flow cytometry, fluorescence-activated cell sorting and/or bead-based cell separation, as described above. Therefore, in a preferred embodiment, the cell is centrifuged, cultivated in large scale, undergoing flow cytometry, undergoing fluorescence-activated cell sorting and/or is separated using beads after step b) of the method of the invention.

In a yet further preferred embodiment of the present invention, the cell is a cell in suspension and/or the cell is an animal or human cell, particularly a vertebrate cell, especially a mammalian cell. Such cells are in particular sensitive regarding shear forces and are therefore difficult to handle and manipulate without affecting viability. Even more preferably, the cell is an animal or human cell in suspension, particularly a vertebrate cell in suspension, especially a mammalian cell in suspension.

In an even more preferred embodiment, the cell or cell population is a white blood cell or white blood cells, respectively, which are even more preferably human white blood cells. The methods of the invention effectively stabilize such cells (Example 5).

The method of the invention can be performed for cell stabilization during centrifugation processes.

Such centrifugation steps are employed for example for separation of cells from surrounding liquids like media. Cells have to be centrifuged and therefore are exposed to shear stress. Very sensitive and fragile cell populations can be damaged by such processes. The methods and uses of the invention improve the handling of such cell populations. In a preferred embodiment, the cells are centrifugated after step b) of the method of the invention. Preferably, they are centrifugated for example with 100 g, 200 g, 500 g, 1000 g or more, for 5 or more minutes, for example for 1 hour or 5 hours.

The methods of the invention can also be performed for cell stabilization in biotechnology, for example in large scale animal cell cultivation: it has been published that shear sensitivity of mammalian cells can be a relevant problem which can complicate the development of large scale animal cell cultivation. The methods and uses of the invention reduce these problems.

Therefore, the present invention also relates to the method of the invention for stabilizing cells in large scale animal cell cultivation. In a preferred embodiment, the cells cultivated in large scale after step b) of the method of the invention, for example by batch cultivation and/or in a volume of more than 10 ml, 50 ml, 100 ml or 1 l of liquid media.

The methods of the invention can also be performed for cell stabilization in flow cytometry and/or fluorescence activated cell sorting:

Flow cytometry is a very commonly used method to separate specific cell population. Within this process, cells are exposed to high shear stresses dependent on the flow speed. The method of the invention reduces this shear stress.

Therefore, the present invention also relates to the methods of the invention for stabilizing cells in flow cytometry and/or fluorescence activated cell sorting or wherein the cells are exposed to flow cytometry and/or fluorescence activated cell sorting after step b) of the method of the invention.

The methods of the invention can also be performed for cell stabilization in bead-based cell separation processes:

Cell populations with a distinct phenotype can be separated by specific antibodies coupled to magnetic beads. Within this process cells are exposed to high shear stresses dependent on the bead size. The method of the invention reduces this shear stress.

Therefore, the methods of the invention can also be performed for stabilizing cells in bead-based cell separation processes. In a preferred embodiment, the cells are coupled to beads, in particular magnetic beads after step b) of the method of the invention and are separated, in particular magnetically separated.

In yet further embodiment, the present invention relates to the use of a kit comprising at least one compound or composition as described above for stabilizing a cell.

The kit may further comprise two or more compounds for use according to the invention stored separately, e.g. in a vessel or syringe. They may be stored in dry form, e.g. freeze-dried or dried, or as solution, or in frozen form, e.g. as frozen solution.

In case compounds further comprise a label moiety and/or linking group, the stabilized cell with compound bound thereto can in addition be used for detection and/or characterization of rare cells, preferably for one rare cell characterization.

In such use, nucleated cells isolated from whole blood can be immobilized on a defined surface using the compounds for use according to the invention on an array, in particular microarray or nanoarray. Rare cells within this population of nucleated cells, for example within a population of white blood cells (WBCs) e.g. circulating tumor cells, endothelial cells, or epithelial cells, can be quantitatively bound to this surface and identified via an antibody or specific binding molecule against an antigen or biochemical property specific for the rare cell population. This enables the exact localization and re-localization for further characterization steps if required.

The compounds which further comprise a linking group may further be used for immobilization of suspension cells, preferably for screening, even more preferably for screening with antibodies or antigen-binding antibody fragments or binding molecules of other formats. Screening of antibodies or antigen-binding fragments thereof on culture cell lines is a general application in antibody development. One application comprises the binding of the antibody to a specific receptor molecule on the cell surface. Using a secondary antibody (sandwich effect) binding characteristics of the first antibody can be investigated. Using suspension cells it is difficult to perform such experiments. The developed compounds useful for cell immobilization allow the careful immobilization of suspension cells without loosing any physiological cell properties and can be therefore used to perform such screening assays. Also, suspension cells can be immobilized for functional cell assays using the compounds for use according to the invention. Assays studying cellular function in vitro or in vivo are of importance: Functional cellular assays are generally used in pharmaceutical, agrochemical and biotechnological research and development to investigate small molecule compounds or biologicals or to identify classes of small molecules in high throughput screening. Some functional assays are based on surface-dependent assays and are therefore generally performed with adherent cells.

In one preferred embodiment, the uses and methods of the invention are in vitro uses and methods.

Compounds further comprising a linking group are further useful for the binding of living cells to a solid surface, followed by detachment off the surface and implantation into mouse models. These kinds of functional assays are of major importance, e.g. for studying the tumor-inducing potential of circulating abnormal cells.

Also, the compounds are further useful for a lab on a chip: To investigate cell morphology or cell function of few cells like 2 to 50 cells, or single cells, a surface can be selectively and systematically spotted with a compound for use according invention further comprising a linking group. This spotting allows a targeted immobilization of few cells or single cells on such spot. This allows molecular analysis directly on the surface (chip). The chip may be an array, in particular microarray or nanoarray.

A compound for use according to the invention further comprising a linking group may be bound to a solid substrate. Such solid substrate may be a particle like a nanoparticle, in particular magnetic nanoparticle, a column, or a flat substrate, an array or a well plate, in particular oligo- or multi-well plate.

Disclosed is a method of labeling a cell, the method comprising:
a) providing a compound for use according to the invention, wherein the compound further comprises a label moiety; and
b) contacting a cell with the compound under conditions allowing the interaction of the compound with the membrane of the cell, thereby immobilizing the label on the cell; and
c) optionally detecting the label.

As shown in the examples, a compound for use according to the invention, wherein the compound comprises a label moiety, is contacted with a cell. As labelling is preferably done with viable or potentially viable cells, the cells are typically present in an aqueous solution, which is preferably buffered and/or contains nutrients, e.g. the cells are suspended in PBS. The labeled compound for use according to the invention may be added to the cells, e.g. in form of a solution, e.g. as aqueous solution by methods known in the art, as pipetting.

Typically, the contacting takes place at a temperature of about 1° C. to 45° C., preferably, 10° C. to 30° C., more preferably 22° to 38° C.

Also, the contacting takes place at a pressure of about 900 to 1100 mbar in order to maintain cell viability.

Also, the cells are preferably incubated with the compounds for a sufficient time to allow for binding. Typically, the cells are preferably incubated with the compounds for 1 minute to 3 days, preferably 5 minutes to 24 h, even more preferably for 10 minutes to 8 hours.

Moreover, the aqueous solution is typically chosen not to affect the integrity and/or viability of a cell.

Such conditions allow the interaction of the compound with the membrane of the cell. Thereby the label moiety is immobilized on the cell.

The label moiety, and thereby the cell, can be detected as described above, depending on the label moiety chosen. In case of a direct label, the detection can take place directly, e.g. by detecting the fluorescence of fluorescein or absorption of dT, as shown in the examples.

In case of indirect detection systems, the second member of a binding pair may be detected. For example, a biotin labeled compound for use according to the invention may be used. For detection, streptavidin, which in turn is labeled with a directly detectable label, may be used. Therefore, biotin may represent a linking group or a label moiety of the invention, depending on the further steps.

For cell-independent labeling, certain compositions of the inventions described above may be used.

Disclosed is a method of labeling a cell, the method comprising
a) providing composition comprising at least three different compounds for use according to the invention, wherein the different compounds differ at least in their hydrophobic domains and wherein the different compounds comprise a label moiety,
b) contacting a cell with the composition under conditions allowing the interaction of the compound with the membrane of the cell, thereby labeling the cell, and
c) optionally detecting the label.

The composition is therefore preferably solution, more preferably aqueous solution comprising the compounds for use according to the invention.

Disclosed is a method of immobilizing a linking group on the surface of a cell, the method comprising
a) providing a compound for use according to the invention, wherein the compound comprises a linking group; and
b) contacting a cell with the compound under conditions allowing the interaction of the compound with the membrane of the cell, thereby immobilizing the linking group.

Regarding the antibodies and antigen-binding antibody fragments, skilled person is aware of such molecules: Naturally occurring antibodies are globular plasma proteins (~150 kDa (http://en.wikipedia.org/wiki/Dalton_unit)) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM. In the present invention, examples of suitable formats include the format of naturally occurring antibodies including antibody isotypes known as IgA, IgD, IgE, IgG and IgM.

In addition to naturally occurring antibodies, artificial antibody formats including antibody fragments have been developed. Some of them are described in the following.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

Accordingly, the term "antibody", as used herein, means any polypeptide which has structural similarity to a naturally occurring antibody and is capable of specific binding to the respective target, wherein the binding specificity is determined by the CDRs. Hence, "antibody" is intended to relate to an immunoglobulin-derived structure with binding to the respective target including, but not limited to, a full length or whole antibody, an antigen binding fragment (a fragment derived, physically or conceptually, from an antibody structure), a derivative of any of the foregoing, a chimeric molecule, a fusion of any of the foregoing with another polypeptide, or any alternative structure/composition which selectively binds to the respective target. The antibody or functionally active parts thereof may be any polypeptide which comprises at least one antigen binding fragment. Antigen binding fragments consist of at least the variable domain of the heavy chain and the variable domain of the light chain, arranged in a manner that both domains together are able to bind to the specific antigen.

"Full length" or "complete" antibodies refer to proteins that comprise two heavy (H) and two light (L) chains inter-connected by disulfide bonds which comprise: (1) in terms of the heavy chains, a variable region and a heavy chain constant region which comprises three domains, CH1, CH2 and CH3; and (2) in terms of the light chains, a light chain variable region and a light chain constant region which comprises one domain, CL.

"Antigen-binding antibody fragments" or "Antigen-binding fragments thereof" also contain at least one antigen binding fragment as defined above, and exhibit essentially the same function and binding specificity as the complete antibody of which the functionally active part (or fragment) is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Variable domains (Fvs) are the smallest fragments with an intact antigen-binding domain consisting of one VL and one VH. Such fragments, with only the binding domains, can be generated by enzymatic approaches or expression of the relevant gene fragments, e.g. in bacterial and eukaryotic cells. Different approaches can be used, e.g. either the Fv fragment alone or 'Fab'-fragments comprising one of the upper arms of the "Y" that includes the Fv plus the first constant domains. These fragments are usually stabilized by introducing a polypeptide link between the two chains which results in the production of a single chain Fv (scFv). Alternatively, disulfide-linked Fv (dsFv) fragments may be used. The binding domains of fragments can be combined with any constant domain in order to produce full length antibodies or can be fused with other proteins and polypeptides.

A recombinant antibody fragment is the single-chain Fv (scFv) fragment. Dissociation of scFvs results in monomeric scFvs, which can be complexed into dimers (diabodies), trimers (triabodies) or larger aggregates such as TandAbs and Flexibodies.

Antibodies with two binding domains can be created either through the binding of two scFv with a simple polypeptide link (scFv)2 or through the dimerization of two monomers (diabodies). The simplest designs are diabodies that have two functional antigen-binding domains that can be either the same, similar (bivalent diabodies) or have specificity for distinct antigens (bispecific diabodies).

Also, antibody formats comprising four variable domains of heavy chains and four variable domains of light chains have been developed. Examples of these include tetravalent bispecific antibodies (TandAbs and Flexibodies, Affirmed Therapeutics AG, Heidelberg. Germany). Flexibodies are a combination of scFv with a diabody multimer motif resulting in a multivalent molecule with a high degree of flexibility for joining two molecules which are quite distant from each other on the cell surface. If more than two functional antigen-binding domains are present and if they have specificity for distinct antigens, the antibody is multi-specific.

In summary, specific immunoglobulin types which represent antibodies or antigen-binding fragments thereof include but are not limited to the following antibody: a Fab (monovalent fragment with variable light (VL), variable heavy (VH), constant light (CL) and constant heavy 1 (CHI) domains), a F(ab')2 (bivalent fragment comprising two Fab fragments linked by a disulfide bridge or alternative at the hinge region), a Fv (VL and VH domains), a scFv (a single chain Fv where VL and VH are joined by a linker, e.g., a peptide linker), a bispecific antibody molecule (an antibody molecule with specificity as described herein linked to a second functional moiety having a different binding specificity than the antibody, including, without limitation, another peptide or protein such as an antibody, or receptor ligand), a bispecific single chain Fv dimer, a diabody, a triabody, a tetrabody, a minibody (a scFv joined to a CH3).

The antibody may be a monoclonal antibody, a chimeric antibody or a humanised antibody.

A tag is a peptide motif used for recognition in biotechnology. A well-known tag is the His-tag (6×Histidine) which can be bound to a $Ni^{2+}$-column.

In case a nucleic acid or nucleic acid analogue/complementary nucleic acid is used as binding pair, any nucleic acid sequence and its complementary sequence may be used.

The lectins are carbohydrate-binding proteins that are highly specific for sugar moieties. As a suitable lectin, Concanavalin A may be used which binds to α-D-mannosyl and α-D-glucosyl residues, branched α-mannosidic structures (high α-mannose type, or hybrid type and biantennary complex type N-Glycans.

As receptor/ligand binding pair, e.g. steroid hormone receptor/steroid hormone may be used. For example, estrogen may be used as steroid, and a receptor thereof as respective binding partner.

Example 1

Synthesis of Compounds Useful in Methods of the Invention

The following compounds useful in methods of the invention were synthesized:

| Internal No. | Scale | chemical structure (modular) | Yield |
|---|---|---|---|
| BMO 29.891131 | 10 μMol Scale | 5'-alphaTocopherolTEG-PEG2000-Fluos-3' | 58 pMol/μL-234 nMol |
| DMTrON-Synthesis/all 20 min. Coupling/Standard-CPG-Cleavage/DMTrOFF/Dialysis/no Purification/Crude product/Fluos-Conc. | | | |
| BMO 29.891132 | 10 μMol Scale | 5'-Cholesteryl-TEG-PEG2000-Fluos-3' | 61 pMol/μL-216 nMol |
| DMTrON-Synthesis/all 20 min. Coupling/Standard-CPG-Cleavage/DMTrOFF/Dialysis/no Purification/Crude product/Fluos-Conc. | | | |
| BMO 29.891133 | 10 μMol Scale | 5'-CholesterylTEG-CholesterylTEG-PEG2000-Fluos-3' | 43 pMol/μL-153 nMol |
| DMTrON-Synthesis/all 20 min. Coupling/Standard-CPG-Cleavage/DMTrOFF/Dialysis/no Purification/Crude product/Fluos-Conc. | | | |
| BMO 29.891137 | 10 μMol Scale | 5'-CholesterylTEG-CholesterylTEG-PEG2000-BiotinTEG-3' | 111 pMol/μL-200 nMol |
| DMTrOFF-Synthesis/all 20 min. Coupling/Standard-CPG-Cleavage/Dialysis/no Purification/Crude product/Conc. estimated | | | |
| BMO 29.891180 | 10 μMol Scale | 5'-CholesterylTEG-CholesterylTEG-PEG2000-Fluos-BiotinTEG-3' | 3577 pMol/μL-6440 nMol |
| DMTrOFF-Synthesis/all 20 min. Coupling/Standard-CPG-Cleavage/Dialysis/no Purification/Crude product/Fluos-Conc. | | | |
| BMO 29.891194_Ch01 | 1 μMol Scale | 5'-Myristic acid-Myristic acid-PEG2000-Fluos-BiotinTEG-3' | 10 pMol/μL-12 nMol |
| DMTrON-Synthesis/Coupling: 1 + 2 = 10 min-3 = 2 × 8 min-4 + 5 = 10 min/Standard-CPG-Cleavage/C18-Purification/DMTrOFF/Dialysis/F30-39-TEA+/Fluos-Conc. | | | |
| BMO 29.891194_Ch02 | 1 μMol Scale | 5'-Myristic acid-Myristic acid-PEG2000-Fluos-BiotinTEG-3' | 22 pMol/μL-24 nMol |
| DMTrON-Synthesis/Coupling: 1 + 2 = 10 min-3 = 2 × 8 min-4 + 5 = 15 min/Standard-CPG-Cleavage/C18-Purification/F89-98-TEA+/evaporate/DMTrOFF/Fluos-Conc. | | | |
| BMO 29.891194_Ch03 | 1 μMol Scale | 5'-Myristic acid-Myristic acid-PEG2000-Fluos-BiotinTEG-3' | 11 pMol/μL-11 nMol |
| DMTrON-Synthesis/all 20 min. Coupling/Standard-CPG-Cleavage/C18-Purification/F69-79-TEA+/evaporate/DMTrOFF/Fluos-Conc. | | | |
| BMO 29.891197 | 1 μMol Scale | 5'-Myristic acid-SpacerC9-Myristic acid-PEG2000-Fluos-BiotinTEG-3' | 0.5 pMol/μL-0.7 nMol |
| DMTrON-Synthesis/all 20 min. Coupling/Standard-CPG-Cleavage/C18-Purification/F67-72-TEA+/evaporate/DMTrOFF/Fluos-Conc. | | | |
| BMO 29.89121 3_Ch01 | 10 μMol Scale | 5'-Myristic acid-Myristic acid-SpacerC18-Fluos-BiotinTEG-3' | 538 pMol/μL-808 nMol |
| DMTrON-Synthesis/all 20 min. Coupling/Standad-CPG-Cleavage/T1-C18-Purification/T1 = F40-44-TEA+/evaporate/Fluos-Conc. | | | |
| BMO 29.891213_Ch02 | | 5'-Myristic acid-Myristic acid-SpacerC18-Fluos-BiotinTEG-3' | 613 pMol/μL-919 nMol |
| T2-C18-Purification/T2 = F73-99-TEA+/evaporate/DMTrOFF/Fluos-Conc. | | | |
| BMO 29.891214 | 1 μMol Scale | 5'-Myristic acid-Myristic acid-(SpacerC18)7-Fluos-BiotinTEG-3' | 100 pMol/μL-100 nMol |
| DMTrON-Synthesis/all 10 min. Coupling/Standard-CPG-Cleavage/C18-Purification/F49-53-TEA+/evaporate/DMTrOFF/Fluos-Conc. | | | |
| BMO 29.891218 | 1 μMol Scale | 5'-Myristic acid-SpacerC9-Myristic acid-(SpacerC18)7-Fluos-BiotinTEG-3' | 40 pMol/μL-44 nMol |
| DMTrON-Synthesis/Coupling: 1 + 2 = 20 min-3-9 = 5 min-10-12 = 20 min/Standard-CPG-Cleavage/C18-Purification/F30-35-TEA+/evaporate/DMTrOFF/Fluos-Conc. | | | |

-continued

| Internal No. | Scale | chemical structure (modular) | Yield |
| --- | --- | --- | --- |
| BMO 29.891219 | 1 μMol Scale | 5'-Myristic acid-SpacerC12-Myristic acid-(SpacerC18)7-Fluos-BiotinTEG-3' | 15 pMol/μL-22 nMol |

DMTrON-Synthesis/Coupling: 1 + 2 = 20 min-3-9 = 5 min-10-12 = 20 min/Standard-CPG-Cleavage/C18-Purification/F28-32-TEA+/evaporate/DMTrOFF/Fluos-Conc.

| BMO 29.891220 | 1 μMol Scale | 5'-Myristic acid-SpacerC18-Myristic acid-(SpacerC18)7-Fluos-BiotinTEG-3' | 56 pMol/μL-79 nMol |

DMTrON-Synthesis/Coupling: 1 + 2 = 20 min-3-9 = 5 min-10-12 = 20 min/Standard-CPG-Cleavage/C18-Purification/F34-38-TEA+/evaporate/DMTrOFF/Fluos-Conc.

| BMO 29.891221 | 1 μMol Scale | 5'-Myristic acid-Myristic acid-Myristic acid-(SpacerC18)7-Fluos-BiotinTEG-3' | 38 pMol/μL-42 nMol |

DMTrON-Synthesis/Coupling: 1 + 2 = 20 min-3-9 = 5 min-10-12 = 20 min/Standard-CPG-Cleavage/C18-Purification/F32-41-TEA+/evaporate/DMTrOFF/Fluos-Conc.

| BMO 29.891222_Ch03 | 1 μMol Scale | 5'-CholesterylTEG-CholesterylTEG-(SpacerC18)7-Fluos-BiotinTEG-3' | 12 pMol/μL-14 nMol |

DMTrON-Synthesis/Coupling: 1 + 2 = 2 × 10 min-3-9 = 5 min-10-12 = 2 × 10 min/Standard-CPG-Cleavage/C8-Purification/F69-73-TEA+/evaporate/DMTrOFF/Fluos-Conc.

| BMO 29.891222_Ch04 | 1 μMol Scale | 5'-CholesterylTEG-CholesterylTEG-(SpacerC18)7-Fluos-BiotinTEG-3' | 6 pMol/μL-7 nMol |

DMTrON-Synthesis/Coupling: 1 + 2 = 2 × 15 min-3-9 = 5 min-10-12 = 2 × 15 min/Standard-CPG-Cleavage/C4-Purification/F10-13-TEA+/evaporate/DMTrOFF/Fluos-Conc.

| BMO 29.891222_Ch05 | 1 μMol Scale | 5'-CholesterylTEG-CholesterylTEG-(SpacerC18)7-Fluos-BiotinTEG-3' | 13 pMol/μL-17 nMol |

DMTrOFF-Synthesis/Coupling: 1 + 2 = 2 × 15 min-3-9 = 5 min-10-12 = 2 × 15 min/Standard-CPG-Cleavage/C4-Purification/F60-64-TEA+/evaporate/Fluos-Conc.

| BMO 29.891224 | 1 μMol Scale | 5'-CholesterylTEG-SpacerC12-CholesterylTEG-(SpacerC18)7-Fluos-BiotinTEG-3' | 74 pMol/μL-81 nMol |

DMTrON-Synthesis/Coupling: 1 + 2 = 20 min-3-9 = 5 min-10-12 = 20 min/Standard-CPG-Cleavage/C18-Purification/F26-33-TEA+/evaporate/DMTrOFF/Fluos-Conc.

| BMO 29.891225 | 1 μMol Scale | 5'-CholesterylTEG-SpacerC18-CholesterylTEG-(SpacerC18)7-Fluos-BiotinTEG-3' | 5 pMol/μL-6 nMol |

DMTrON-Synthesis/Coupling: 1 + 2 = 20 min-3-9 = 5 min-10-12 = 20 min/Standard-CPG-Cleavage/C18-Purification/F14-19-TEA+/evaporate/DMTrOFF/Fluos-Conc.

| BMO 29.891227 | 1 μMol Scale | 5'-Myristic acid-CholesterylTEG-(SpacerC18)7-Fluos-BiotinTEG-3' | 20 pMol/μL-21 nMol |

DMTrON-Synthesis/Coupling: 1 + 2 = 20 min-3-9 = 5 min-10-12 = 20 min/Standard-CPG-Cleavage/C18-Purification/F34-40-TEA+/evaporate/DMTrOFF/Fluos-Conc.

| BMO 29.891228_Ch02 | 1 μMol Scale | 5'-CholesterylTEG-Myristic acid-(SpacerC18)7-Fluos-BiotinTEG-3' | 9 pMol/μL-11 nMol |

DMTrON-Synthesis/Coupling: 1 + 2 = 20 min-3-9 = 5 min-10-12 = 20 min/Standard-CPG-Cleavage/C18-Purification/F28-31-TEA+/evaporate/DMTrOFF/Fluos-Conc.

| BMO 29.891234_Ch03 | 10 μMol Scale | 5'-CholesterylTEG-CholesterylTEG-(SpacerC18)7-dT(Determ. of concentration)-BiotinTEG-3' | 239 pMol/μL-358 nMol |

DMTrOFF-Synthesis-1000A-Universal-CPG/Coupling: 1 = 20 min-3-8 = 5 min-9-11 = 20 min/CPG-Cleavage = NH3-Isoprop/C8-Purification/F65-70-TEA+/evaporate/260 nm Conc.

| BMO 29.891234_Ch04 | 10 μMol Scale | 5'-CholesterylTEG-CholesterylTEG-(SpacerC18)7-dT(Determ. of concentration)-BiotinTEG-3' | 204 pMol/μL-307 nMol |

DMTrOFF-Synthesis-Universal-PS/Coupling: 1 = 20 min-3-8 = 5 min-9-11 = 20 min/CPG-Cleavage = NH3-Isoprop/C8-Purification/F83-88-TEA+/evaporate/260 nm Conc.

| BMO 29.891234_Ch07 | 10 μMol Scale | 5'-CholesterylTEG-CholesterylTEG-(SpacerC18)9bis10-dT(Determ. of concentration)-BiotinTEG-3' | 277 pMol/μL-415 nMol |

DMTrOFF-Synthesis-Universal-PS + Hyazinthactivator/SpacerC18 = 0.2M/Coupling: 1 + 2 = 3 min-3 = 2 × 5 min-4-11 = 3 min/CPG-Cleavage = NH3-Isoprop/C8-Purification/F55-59-Na+/Vivaspin 2'000/260 nm Conc.

| BMO 29.891234_Ch08 | 10 μMol Scale | 5'-CholesterylTEG-CholesterylTEG-(SpacerC18)9bis10-dT(Determ. of concentration)-BiotinTEG-3' | 306 pMol/μL-460 nMol |

DMTrOFF-Synthesis-Universal-PS + Hyazinthactivator/SpacerC18 = 0.2M/Coupling: 1 + 2 = 3 min-3 = 2 × 5 min-4-11 = 3 min/CPG-Cleavage = NH3-Isoprop/C8-Purification/F37-41-Na+/Vivaspin 2'000/260 nm Conc.

| BMO 29.891234_Ch09 | 10 μMol Scale | 5'-CholesterylTEG-CholesterylTEG-(SpacerC18)7-SpacerC3-dT(Determ. of concentration)-BiotinTEG-3' | see below |

DMTrOFF-Synthesis-1000A-Universal-CPG + Hyazinthactivator/SpacerC18 = 0.2M/Coupling: 1 + 2 = 3 min-3 + 4 = 2 × 10 min-5-10 = 10 min-11 + 12 = 3 min/CPG-Cleavage = NH3-Isoprop/crude und C8-Purification/F = see below/Vivaspin 2'000/260 nm Conc.

| | T1_crude | | 1'356 pMol/μL-2'033 nMol |
| | T2_crude_Na | | 1'165 pMol/μL-1'747 nMol |
| | T3_F38-40 | | 53 pMol/μL-80 nMol |
| | T4_F38-40_Na | | 51 pMol/μL-77 nMol |

| BMO 29.891236_Ch10 | 10 μMol Scale | 5'-CholesterylTEG-CholesterylTEG-(SpacerC18)7-SpacerC3-dT(Determ. of concentration)-BiotinTEG-3' | see below |

DMTrOFF-Synthesis-10000A-Universal-CPG + Hyazinthactivator/SpacerC18 = 0.2M/Coupling: 1 + 2 = 3 min-3 + 4 = 2 × 10 min-5-10 = 10 min-11 + 12 = 3 min/CPG-Cleavage = NH3-Isoprop/CRUDE und C8-Purification/F = see below/Vivaspin 2'000/260 nm Conc.

| | T1_crude | | 2'430 pMol/μL-3'645 nMol |
| | T2_F37-39_Na | | 227 pMol/μL-341 nMol |

| BMO 29.891237_Ch11 | 10 μMol Scale | 5'-CholesterylTEG-CholesterylTEG-(SpacerC18)7-dT(Determ. of concentration)-BiotinTEG-p-3' | see below |

DMTrOFF-Synthesis-2000A-dT-CPG/SpacerC18 = 0.2M/Coupling: 1 + 2 = 20 min-3 + 4 = 2 × 10 min-5-10 = 10 min-11 + 12 = 20 min/CPG-Cleavage = NH3-Isoprop/CRUDE und C8-Purification/F = see below/Vivaspin 2'000/260 nm Conc.

| | F42-45_Na | | 166 pMol/μL-248 nMol |
| | F47-49_Na | | 100 pMol/μL-150 nMol |

-continued

| Internal No. | Scale | chemical structure (modular) | Yield |
|---|---|---|---|
| BMO 29.891237_Ch12 | 10 μMol Scale | 5'-CholesterylTEG-CholesterylTEG-(SpacerC18)7-dT(Determ. of concentration)-BiotinTEG-p-3' | see below |

DMTrOFF-Synthesis-2000A-dT-CPG/SpacerC18 = 0.2M/Coupling: 1 + 2 = 20 min-3 + 4 = 2 × 10 min-5-10 = 10 min-11 + 12 = 20 min/CPG-Cleavage = NH3-Isoprop/CRUDE und C8-Purification/F = see below/Vivaspin 2'000/260 nm Conc.

| | | | |
|---|---|---|---|
| | F51-53_Na | | 216 pMol/μL-324 nMol |
| | F56-59_Na | | 160 pMol/μL-250 nMol |

Exemplary Syntheses performed and results thereof:

A)

| | | | | | | | | |
|---|---|---|---|---|---|---|---|---|
| DK1194Ch02 | 1 μMol Scale | 5'-Myristic acid | Myristic acid | PEG-2000 | | 6CarboxyFluos | Biotin-TEG-3' | 11 pMol/μL | synthesized and determined |
| DK1197 | 1 μMol Scale | 5'-Myristic acid SpacerC9 | Myristic acid | PEG-2000 | | 6CarboxyFluos | Biotin-TEG-3' | 0.5 pMol/μL | synthesized and determined |
| DK1213 | 10 μMol Scale | 5'-Myristic acid | Myristic acid | SpacerC18 | | 6CarboxyFluos | Biotin-TEG-3' | 538 pMol/μL | 2 charges synthesized and determined |
| DK1214 | 1 μMol Scale | 5'-Myristic acid | Myristic acid | (SpacerC18)x7 | | 6CarboxyFluos | Biotin-TEG-3' | 100 pMol/μL | synthesized and determined |

B)

| | | | | | | | | |
|---|---|---|---|---|---|---|---|---|
| DK1213 | 10 μMol Scale | 5'-Myristic acid | Myristic acid | SpacerC18 | 6CarboxyFluos | Biotin-TEG-3' | 538 pMol/μL | 2 Charges synthesized and determined |
| DK1214 | 1 μMol Scale | 5'-Myristic acid | Myristic acid | (SpacerC18)x7 | 6CarboxyFluos | Biotin-TEG-3' | 100 pMol/μL | synthesized and determined |
| DK1218 | 1 μMol Scale | 5'-Myristic acid SpacerC9 | Myristic acid | (SpacerC18)x7 | 6CarboxyFluos | Biotin-TEG-3' | 40 pMol/μL | |
| DK1219 | 1 μMol Scale | 5'-Myristic acid SpacerC12 | Myristic acid | (SpacerC18)x7 | 6CarboxyFluos | Biotin-TEG-3' | 15 pMol/μL | |
| DK1220 | 1 μMol Scale | 5'-Myristic acid SpacerC18 | Myristic acid | (SpacerC18)x7 | 6CarboxyFluos | Biotin-TEG-3' | 56 pMol/μL | |
| DK1221 | 1 μMol Scale | 5'-Myristic acid Myristic acid | Myristic acid | (SpacerC18)x7 | 6CarboxyFluos | Biotin-TEG-3' | 38 pMol/μL | |
| DK1222 | 1 μMol Scale | 5'-Cholesteryl-TEG | Cholesteryl-TEG | (SpacerC18)x7 | 6CarboxyFluos | Biotin-TEG-3' | 12 + 6 + 13 pMol/μL | |
| DK1223 | 1 μMol Scale | 5'-Cholesteryl-TEG SpacerC9 | Cholesteryl-TEG | (SpacerC18)x7 | 6CarboxyFluos | Biotin-TEG-3' | | synthesis difficulties |
| DK1224 | 1 μMol Scale | 5'-Cholesteryl-TEG SpacerC12 | Cholesteryl-TEG | (SpacerC18)x7 | 6CarboxyFluos | Biotin-TEG-3' | 74 pMol/μL | |
| DK1225 | 1 μMol Scale | 5'-Cholesteryl-TEG SpacerC18 | Cholesteryl-TEG | (SpacerC18)x7 | 6CarboxyFluos | Biotin-TEG-3' | 5 pMol/μL | |
| DK1226 | 1 μMol Scale | 5'-Cholesteryl-TEG Cholesteryl-TEG | Cholesteryl-TEG | (SpacerC18)x7 | 6CarboxyFluos | Biotin-TEG-3' | | synthesis difficulties |
| DK1227 | 1 μMol Scale | 5'-Myristic acid | Cholesteryl-TEG | (SpacerC18)x7 | 6CarboxyFluos | Biotin-TEG-3' | 20 pMol/μL | |
| DK1228 | 1 μMol Scale | 5'-Cholesteryl-TEG | Myristic acid | (SpacerC18)x7 | 6CarboxyFluos | Biotin-TEG-3' | 9 pMol/μL | |
| DK1229 | 1 μMol Scale | 5'-Cholesteryl-TEG SpacerC3 Cholesteryl-TEG SpacerC3 | Cholesteryl-TEG | (SpacerC3)x7 | 6CarboxyFluos | Biotin-TEG-3' | | |
| | 1 μMol Scale | 5'-Cholesteryl-TEG SpacerC9 | Myristic acid | (SpacerC18)x7 | 6CarboxyFluos | Biotin-TEG-3' | | |
| | 1 μMol Scale | 5'-Cholesteryl-TEG SpacerC12 | Myristic acid | (SpacerC18)x7 | 6CarboxyFluos | Biotin-TEG-3' | | |
| | 1 μMol Scale Biotin-TEG | 5'-Cholesteryl-TEG SpacerC18 CPG 11 columns | Myristic acid | (SpacerC18)x7 | 6CarboxyFluos | Biotin-TEG-3' | | |
| DK1193 | Myristic acid | PA-1 11 0.1M | 0.5 g | | 4.50 mL ACN | | | |
| 10-1975 | Cholesteryl-TEG | PA-2 13 0.1M | 1 × 0.25 g + 1 × 100 μMol à 11 + 4 Couplings | | 3.10 mL ACN | | | |
| 10-1964 | 6CarboxyFluos | PA-3 11 0.1M | 1 × 0.25 g + 1 × 100 μMol à 11 + 4 Couplings | | 3.20 mL ACN | | | |

| | | | | -continued | |
|---|---|---|---|---|---|
| 10-1909 | SpacerC9 | PA-4 2 0.1M | 1 × 100 μMol | | 1.00 mL ACN |
| 10-1928 | SpacerC12 | PA-5 2 0.1M | 1 × 100 μMol | | 1.00 mL ACN |
| 10-1918 | Spacer-C18 | PA-6 79 0.1M | 5 × 0.25 g<br>à 18 Couplings | | 16.00 mL ACN |

C)

| ID | Scale | 5'- | Mod1 | Mod2 | Mod3 | Mod4 | Mod5 | Mod6 | Mod7 | 3' | Amount | Notes |
|---|---|---|---|---|---|---|---|---|---|---|---|---|
| DK1213 | 10 μMol Scale | 5'- | | | | Myristic acid | Myristic acid | SpacerC18 | 6CarboxyFluos | Biotin-TEG | -3' | 538 pMol/μL | 2 Charges synthesized and determined |
| DK1214 | 1 μMol Scale | 5'- | | | | Myristic acid | Myristic acid | (SpacerC18) × 7 | 6CarboxyFluos | Biotin-TEG | -3' | 100 pMol/μL | synthesized and determined |
| DK1218 | 1 μMol Scale | 5'- | | Myristic acid | | SpacerC9 | Myristic acid | (SpacerC18) × 7 | 6CarboxyFluos | Biotin-TEG | -3' | 40 pMol/μL | |
| DK1219 | 1 μMol Scale | 5'- | | Myristic acid | | SpacerC12 | Myristic acid | (SpacerC18) × 7 | 6CarboxyFluos | Biotin-TEG | -3' | 15 pMol/μL | |
| DK1220 | 1 μMol Scale | 5'- | | Myristic acid | | SpacerC18 | Myristic acid | (SpacerC18) × 7 | 6CarboxyFluos | Biotin-TEG | -3' | 56 pMol/μL | |
| DK1221 | 1 μMol Scale | 5'- | | Myristic acid | | Myristic acid | Myristic acid | (SpacerC18) × 7 | 6CarboxyFluos | Biotin-TEG | -3' | 38 pMol/μL | |
| DK1222 | 1 μMol Scale | 5'- | | | | Cholesteryl-TEG | Cholesteryl-TEG | (SpacerC18) × 7 | 6CarboxyFluos | Biotin-TEG | -3' | 12 + 6 + 13 pMol/μL | |
| DK1223 | 1 μMol Scale | 5'- | Cholesteryl-TEG | | | SpacerC9 | Cholesteryl-TEG | (SpacerC18) × 7 | 6CarboxyFluos | Biotin-TEG | -3' | synthesis difficulties | |
| DK1224 | 1 μMol Scale | 5'- | Cholesteryl-TEG | | | SpacerC12 | Cholesteryl-TEG | (SpacerC18) × 7 | 6CarboxyFluos | Biotin-TEG | -3' | 74 pMol/μL | |
| DK1225 | 1 μMol Scale | 5'- | Cholesteryl-TEG | | | SpacerC18 | Cholesteryl-TEG | (SpacerC18) × 7 | 6CarboxyFluos | Biotin-TEG | -3' | 5 pMol/μL | |
| DK1226 | 1 μMol Scale | 5'- | Cholesteryl-TEG | | | Cholesteryl-TEG | Cholesteryl-TEG | (SpacerC18) × 7 | 6CarboxyFluos | Biotin-TEG | -3' | synthesis difficulties | |
| DK1227 | 1 μMol Scale | 5'- | | | | Myristic acid | Myristic acid | (SpacerC18) × 7 | 6CarboxyFluos | Biotin-TEG | -3' | 20 pMol/μL | |
| DK1228 | 1 μMol Scale | 5'- | | | | Cholesteryl-TEG | Myristic acid | (SpacerC18) × 7 | 6CarboxyFluos | Biotin-TEG | -3' | 9 pMol/μL | |
| DK1229 | 1 μMol Scale | 5'- | Cholesteryl-TEG | | | SpacerC3 | Cholesteryl-TEG | SpacerC3 | Cholesteryl-TEG | (SpacerC3) × 7 | 6CarboxyFluos | Biotin-TEG | -3' |
| | 1 μMol Scale | 5'- | Cholesteryl-TEG | | | SpacerC9 | Myristic acid | (SpacerC18) × 7 | 6CarboxyFluos | Biotin-TEG | -3' | no Synthesis | |
| | 1 μMol Scale | 5'- | Cholesteryl-TEG | | | SpacerC12 | Myristic acid | (SpacerC18) × 7 | 6CarboxyFluos | Biotin-TEG | -3' | no Synthesis | |
| | 1 μMol Scale | 5'- | Cholesteryl-TEG | | | SpacerC18 | Myristic acid | (SpacerC18) × 7 | 6CarboxyFluos | Biotin-TEG | -3' | no Synthesis | |
| DK1234 | 10 μMol Scale | 5'- | | | | Cholesteryl-TEG | Cholesteryl-TEG | (SpacerC18) × 7 | dT (determination of concentration) | Biotin-TEG | -3' | 239 + 307 pMol/μL | |

D) Chemical Structures of the Exemplary Compounds Useful in Methods of the Invention as well as Side Products The chemical structures of the exemplary compounds useful in methods of the invention as well as side products of synthesis are depicted in FIGS. 6A and B.

E) Synthesis of Biotin-PEG-Lys-(C18)2

The synthesis of Biotin-PEG-Lys-(C18)2 of the invention is shown in FIG. 6C.

F) Structures of Further Compounds Useful in Methods of the Invention and Reference Compounds, as well as Intermediates Thereof For synthesis of compounds useful in methods of the invention and reference compounds, following intermediates were used:
cholesteryl-TEG-CE-PA (GlenResearch 10-1975),
myristic acid-CE-PA (inhouse production),
biotin-TEG-CE-PA (GlenResearch 10-1955),
biotin-dT-CE-PA (GlenResearch 10-1038),
dT-CE-PA (GlenResearch 10-1030),
symmetric doubler-CE-PA (GlenResearch 10-1920),
PEG-200-CED-PA (ChemGenes CLP-2119),
6-Fluorescein-CE-PA (GlenResearch 10-1964) and
universal-CPG (Proligo 1000A M401010).

Structures of further compounds useful in methods of the invention and reference compounds, as well as intermediates are shown in FIG. 12.

Example 2

Labelling of Cells Using Compounds Useful in Methods of the Invention

WBC: white blood cells

| | Linol (1,1'-dilinoleyl-3,3,3',3'-tetramethylindocarbocyanine perchlorate, Invitrogen) | Oleyl (NOF-BAM) | PKH26 (Myristic acid, behenic acid; SIGMA) | PKH67 (SIGMA) | PKH2 (SIGMA) | Phosphatidylethanolamine (N-(4,4-difluoro-5,7-dimethyl-4-bora-3a,4a-diaza-s-indacene-3-propionyl)-1,2-dihexadecanoyl-sn-glycero-3-phosphoethanolamine, triethylammonium salt, Invitrogen) | Sphingomyelin (N-(4,4-difluoro-5,7-dimethyl-4-bora-3a,4a-diaza-s-indacene-3-pentanoyl)sphingosyl phosphocholine; Invitrogen) |
|---|---|---|---|---|---|---|---|
| WBCs | is taken up by most cells (more in comparison to other molecules (Exposure time: 20-50 ms) ✓ | is not taken up by all cells (granulocytes potentially negative) ✓ | stains granulocytes and almost all other blood cells (1 Exp.: 3 cells not stained) ✓ | stains almost all cells; apparently no monocytes, combination of linol and PKH67- all cells stained ✓ | does not stain all cells, other PKHs better ✓ | x | (x)- very bad |
| U937 | ✓ | | ✓ | | | | |
| MDA-MB468 | ✓ | ✓ not all | ✓ | | | | |
| Jurkats | ✓ | ✓ | ✓ | | | x | x |
| CHO | ✓ | | ✓ | | | x | x very weak |
| COS 7 | ✓ | | ✓ | | | x | x |
| Hela | ✓ | | ✓* | | | x/✓ very weak | ✓ |
| NIH 3T3 | ✓ | | ✓ | | | x | x |
| Epithelial cells | ✓ | ✓ | ✓ not all | ✓ | | ✓ not all | x | ✓ |

*one cell stained weakly

| | Cholesterol (Invitrogen; cholesteryl 4,4-difluoro-5-(2-pyrrolyl)-4-bora-3a,4a-diaza-s-indacene-3-undecanoate) | BMO 29.891133 ID: 3882 5'-XXYZ-3' X = Cholesteryl-TEG Y = PEG2000 Z = Fluos | BMO: 29.891132 ID: 3880 5'-XYZ-3' X = Cholesteryl-TEG Y = PEG2000 Z = Fluos | BMO: 29.891131 ID: 3879 5'-XYZ-3' X = a-Tocopherol-TEG Y = PEG2000 Z = Fluos | 1,1'-Dioctadecyl-3,3,3',3'-tetramethylindocarbocyanin perchlorate Sigma 42364 -100 mg | BMO: 15.000078 Sulfo-JA133-phenylboronic acid |
|---|---|---|---|---|---|---|
| WBCs | x | taken up by most cells (more in comparison to other molecules (Exposure time: 50-200 ms) ✓ | ✓ not all | ✓ not all | ✓ not all | ✓ not all |
| U937 | | ✓ | ✓ | ✓ | ✓ | ✓ |
| MDA-MB468 | | ✓ | ✓ | ✓ | ✓ | ✓ |
| Jurkats | x | ✓ | | | | ✓ |
| CHO | x | ✓ | | | | ✓ |
| COS 7 | x | ✓ | | | | ✓ |

-continued

|  | Cholesterol (Invitrogen; cholesteryl 4,4-difluoro-5-(2-pyrrolyl)-4-bora-3a,4a-diaza-s-indacene-3-undecanoate) | BMO 29.891133 ID: 3882 5'-XXYZ-3' X = Cholesteryl-TEG Y = PEG2000 Z = Fluos | BMO: 29.891132 ID: 3880 5'-XYZ-3' X = Cholesteryl-TEG Y = PEG2000 Z = Fluos | BMO: 29.891131 ID: 3879 5'-XYZ-3' X = a-Tocopherol-TEG Y = PEG2000 Z = Fluos | 1,1'-Dioctadecyl-3,3,3',3'-tetramethyl-indocarbocyanin perchlorate Sigma 42364 -100 mg | BMO: 15.000078 Sulfo-JA133-phenylboronic acid |
|---|---|---|---|---|---|---|
| Hela | x/✓ | ✓ |  |  | ✓ |  |
| NIH 3T3 | x | ✓ |  |  | ✓* |  |
| Epithelial cells | x very weak | ✓ | ✓ | ✓ | ✓ | ✓ |

*one cell not stained

Example 3

Results of Experiments Relating to the Immobilization of Cells

The following applies for modular description of the compounds below:

X=hydrophobic moiety, Y=PEG2000, Z=Biotin-TEG, F=Fluos=fluorescein

In the following experiment, the recovery rate of cells was determined.

A)

| tested compound | modular structure | Internal Reference number | Recovery Rate | cells | concentration |
|---|---|---|---|---|---|
| Sunbright(OE-0800S)DADOO-Biotin | | 15.260250 | | | |
| BAM-SH | | 15.260254 | 28.0% | WBCs | |
| Cholesteryl-TEG-Cholesteryl-TEG-PEG2000-Biotin-TEG | 5'-XXYZ-3' | 29.891137 | 77.1% | WBCs | |
| Biotin-PEG2000- Boronic acid | | 15.260267 | 16.3% | WBCs | |
| Cholesteryl-TEG-Cholesteryl-TEG-PEG2000-Fluos-Biotin-TEG | 5'-XXYFZ-3' | 29.891180 | 71-90%<br>77.7%<br>62.3%<br>95.8%<br>77.9%<br>88.5%<br>69.7%<br>79.2%<br>72.5% | WBCs<br>WBCs<br>WBCs<br>WBCs<br>WBCs<br>WBCs<br>WBCs<br>WBCs<br>WBCs | 350 pmol/10e6 cells<br>350 pmol/10e6 cells<br>350 pmol/10e6 cells<br>350 pmol/10e6 cells<br>350 pmol/10e6 cells<br>350 pmol/10e6 cells<br>350 pmol/10e6 cells<br>350 pmol/10e6 cells<br>350 pmol/10e6 cells |
| 1,2 Distearoyl-sn-glycero-3-phosphoethanolamine-N-[biotinyl(PEG2000)] | DSPE-PEG(2000) Biotin (Avantilipids) | | 54-83% | WBCs | 350 pmol/10e6 cells |
| Myristic acid-Myristic acid-PEG2000-Fluos-Biotin-TEG | 5'-XXYFZ-3' | 29.891194 | 21-26% | WBCs | |
| Biotin-PEG-lys-(C14)2 | | 15.260268 | 52-86% | WBCs | |
| Myristic acid-Myristic acid-(SpacerC18)7-Fluos-Biotin-TEG | 5'-XXYYYYYYFZ-3' (Y = Spacer) | 29.891214 | 78.9%<br>68.7%<br>90.5%<br>81.1%<br>65.9%<br>84.9%<br>85.1% | WBCs<br>WBCs<br>WBCs<br>WBCs<br>WBCs<br>WBCs<br>WBCs | 350 pmol/10e6 cells<br>350 pmol/10e6 cells<br>350 pmol/10e6 cells<br>350 pmol/10e6 cells<br>350 pmol/10e6 cells<br>350 pmol/10e6 cells<br>350 pmol/10e6 cells |
| Myristic acid-Myristic acid-SpacerC18-Fluos-Biotin-TEG | 5'-XXSYFZ-3' (Y = Spacer) | 29.891213 | 67.4%<br>61.9%<br>80.2%<br>70.4% | WBCs<br>WBCs<br>WBCs<br>WBCs | 350 pmol/10e6 cells<br>350 pmol/10e6 cells<br>350 pmol/10e6 cells<br>350 pmol/10e6 cells |
| Myristic acid-SpacerC9-Myristic acid-PEG2000-Fluos-Biotin-TEG | 5'-XSXYFZ-3' (S = Spacer) | 29.891197 | not enough material; staining not good | WBCs | |
| Myristic acid-SpacerC9-Myristic acid-(SpacerC18)7-Fluos-Biotin-TEG | 5'-XSXYYYYYYYFZ-3' (Y = Spacer) | 29.891218 | 50.3%<br>55.1% | WBCs<br>WBCs | 350 pmol/10e6 cells<br>350 pmol/10e6 cells |

-continued

| tested compound | modular structure | Internal Reference number | Recovery Rate | cells | concentration | |
|---|---|---|---|---|---|---|
| Myristic acid-Cholesteryl-TEG-(SpacerC18)7-Fluos-Biotin-TEG | 5'-XEYYYYYYFZ-3' (Y = Spacer; X = Myr.; E = Chol.)) | 29.891227 | 64.9% | WBCs | 350 pmol/10e6 cells | |
| | | | 69.6% | WBCs | 350 pmol/10e6 cells | |
| | | | 77.8% | WBCs | 350 pmol/10e6 cells | |
| | | | 77.8% | WBCs | 350 pmol/10e6 cells | |
| (Myristic acid)3-(SpacerC18)7-Fluos-Biotin-TEG | 5'-XXXYYYYYYFZ-3' (Y = Spacer) | 29.891221 | 46.0% | WBCs | 350 pmol/10e6 cells | |
| | | | 79.4% | WBCs | 350 pmol/10e6 cells | |
| | | | 68.8% | WBCs | 350 pmol/10e6 cells | |
| | | | 76.5% | WBCs | 350 pmol/10e6 cells | |
| | | | 83.4% | WBCs | 350 pmol/10e6 cells | |
| Myristic acid-SpacerC12-Myristic acid-(SpacerC18)7-Fluos-Biotin-TEG | 5'-XVXYYYYYYFZ-3' (V = Spacer C12, Y = Spacer C18) | 29.891219 | 46.3% | WBCs | 350 pmol/10e6 cells | |
| | | | 39.4% | WBCs | 350 pmol/10e6 cells | |
| | | | 53.7% | WBCs | 350 pmol/10e6 cells | |
| | | | 56.6% | WBCs | 350 pmol/10e6 cells | |
| Myristic acid-SpacerC18-Myrristic acid-(SpacerC18)7-Fluos-Biotin-TEG | 5'-XYXYYYYYYFZ-3' (Y = Spacer C18) | 29.891220 | 35.8% | WBCs | 350 pmol/10e6 cells | |
| | | | 41.4% | WBCs | 350 pmol/10e6 cells | |
| | | | 55.9% | WBCs | 350 pmol/10e6 cells | |
| | | | 63.5% | WBCs | 350 pmol/10e6 cells | |
| Cholesteryl-TEG-Cholesteryl-TEG-(SpacerC18)7-Fluos-Biotin-TEG | 5'-XXXYYYYYYFZ-3' (Y = Spacer C18) | 29.891222 | 52.6% | WBCs | 350 pmol/10e6 cells | |
| | | | 76.3% | WBCs | 350 pmol/10e6 cells | |
| | | | 80.3% | WBCs | 350 pmol/10e6 cells | |
| | | | 70.4% | WBCs | 350 pmol/10e6 cells | |
| | | | 71.3% | WBCs | 350 pmol/10e6 cells | |
| | | | 80.3% | WBCs | 350 pmol/10e6 cells | |
| | | | 4.1% | WBCs | 350 pmol/10e6 cells | |
| | | | 38.8% | WBCs | 350 pmol/10e6 cells | |
| | | | 13.0% | WBCs | 350 pmol/10e6 cells | |
| | | | 11.0% | WBCs | 350 pmol/10e6 cells | |
| | | | 77.0% | WBCs | 350 pmol/10e6 cells | undiluted |
| | | | 79.0% | WBCs | 350 pmol/10e6 cells | 1:1 diluted |
| | | | 23.0% | WBCs | 350 pmol/10e6 cells | undiluted |
| | | | 17.0% | WBCs | 350 pmol/10e6 cells | 1:1 diluted |
| | | | 68.0% | WBCs | 350 pmol/10e6 cells | untreated |
| | | | 61.0% | WBCs | 350 pmol/10e6 cells | US + 10' 98° C. |
| | | | | | | untreated |
| | | | | | | US + 10' 98° C. |
| Cholesteryl-TEG-SpacerC12-Cholesteryl-TEG-(SpacerC18)7-Fluos-Biotin-TEG | 5'-XWXYYYYYYFZ-3' (W = Spacer C12, Y = Spacer C18) | 29.891224 | 119.4% | WBCs | 350 pmol/10e6 cells | |
| | | | 60.6% | WBCs | 350 pmol/10e6 cells | |
| | | | 64.4% | WBCs | 350 pmol/10e6 cells | |
| | | | 70.3% | WBCs | 350 pmol/10e6 cells | |
| | | | 78.1% | WBCs | 350 pmol/10e6 cells | |
| Cholesteryl-TEG-SpacerC18-Cholesteryl-TEG-(SpacerC18)7-Fluos-Biotin-TEG | 5'-XYXYYYYYYFZ-3' (Y = Spacer C18) | 29.891225 | 38.8% | WBCs | 350 pmol/10e6 cells | |
| | | | 46.5% | WBCs | 350 pmol/10e6 cells | |

-continued

| tested compound | modular structure | Internal Reference number | Recovery Rate | cellsconcentration | |
|---|---|---|---|---|---|
| Cholesteryl- Myristic acid-TEG-(SpacerC18)7-Fluos-Biotin-TEG | 5'-EXYYYYYYFZ-3' (Y = Spacer; X = Myr.; E = Chol.)) | 29.891228 | 76.1% | WBCs 350 pmol/10e6 cells | |
| | | | 64.0% | WBCs 350 pmol/10e6 cells | |
| | | | 17.4% | WBCs 350 pmol/10e6 cells | |
| | | | 52.1% | WBCs 350 pmol/10e6 cells | |
| Cholesteryl-TEG-Cholesteryl-TEG-(SpacerC18)7-Biotin-TEG | 5'-XXYYYYYYTZ-3' (Y = Spacer C18) | 29.891234 | 9.6% | WBCs 10 pmol/10e6 cells | |
| | | | 18.8% | WBCs 100 pmol/10e6 cells | |
| | | | 24.9% | WBCs 500 pmol/10e6 cells | |
| | | | 35.4% | WBCs 1000 pmol/10e6 cells | |
| | | | 12.0% | WBCs 350 pmol/10e6 cells | |
| | | | 22.0% | WBCs 350 pmol/10e6 cells | |
| | | | 17.0% | WBCs 350 pmol/10e6 cells | |
| | | | 27.0% | WBCs 350 pmol/10e6 cells | undiluted |
| | | | 10.0% | WBCs 350 pmol/10e6 cells | 1:1 diluted |
| | | | 12.0% | WBCs 350 pmol/10e6 cells | untreated |
| | | | 22.0% | WBCs 350 pmol/10e6 cells | US + 10' 98° C. |
| | | | 22.0% | WBCs 350 pmol/10e6 cells | 0.001% Tween20 |
| | | | 12.0% | WBCs 350 pmol/10e6 cells | 0.0003% Tween20 |
| | | | 14.0% | WBCs 350 pmol/10e6 cells | 0.0001% Tween21 |
| | | | 13.0% | WBCs 350 pmol/10e6 cells | 0.00003% Tween20 |
| | | | 11.0% | WBCs 350 pmol/10e6 cells | 0.00001% Tween21 |
| | | | 26.8% | WBCs 300 pmol/10e6 cells | 0.000003% Tween21 |
| | | | 41.7% | WBCs 1 nmol/10e6 cells | 0.0% Tween22 |
| | | | 99.7% | WBCs 10 nmol/10e6 cells | |
| | | | 36.0% | WBCs 350 pmol/10e6 cells | undiluted |
| | | | 25.0% | WBCs 350 pmol/10e6 cells | 1:1 diluted |
| | | | 13.0% | WBCs 350 pmol/10e6 cells | untreated |
| | | | 23.0% | WBCs 350 pmol/10e6 cells | US + 10' 98° C. |
| | | | 15.0% | WBCs 350 pmol/10e6 cells | 0.001% Tween20 |
| | | | 18.0% | WBCs 350 pmol/10e6 cells | 0.0003% Tween21 |
| | | | 28.0% | WBCs 350 pmol/10e6 cells | 0.0001% Tween22 |
| | | | 36.0% | WBCs 350 pmol/10e6 cells | 0.00003% Tween20 |
| | | | 20.0% | WBCs 350 pmol/10e6 cells | 0.00001% Tween21 |
| | | | 23.0% | WBCs 350 pmol/10e6 cells | 0.000003% Tween20 |
| | | | 25.0% | WBCs 350 pmol/10e6 cells | 0.0000003% Tween21 |
| | | | 35.0% | WBCs 350 pmol/10e6 cells | 0.0% Tween22 |
| Biotin-PEG-Lysin-C18 (stearic acid) | | 15.260271 | 21.0% | WBCs 350 pmol/10e6 cells | also not better at higher concentrations |
| Biotin-PEG-Lysin-C22 (Behenic acid) | | | 27.0% | WBCs 350 pmol/10e6 cells | also not better at higher concentrations |
| Biotin-PEG-Lysin-(C18)2 dissolved in | | | 4.8% | WBCs 10 pmol/10e6 cells | |
| | | | 6.8% | WBCs 100 pmol/10e6 cells | |
| | | | 21.8% | WBCs 1 nmol/10e6 cells | |
| | | | 60.6% | WBCs 10 nmol/10e6 cells | |
| | | | 43.0% | WBCs 10 nmol/10e6 cells | |

-continued

| tested compound | modular structure | Internal Reference number | Recovery Rate | cells | concentration | |
|---|---|---|---|---|---|---|
| | | | 69.0% | WBCs | 50 nmol/10e6 cells | |
| | | | 81.8% | WBCs | 100 nmol/10e6 cells | |
| | | | 29.6% | WBCs | 1 nmol/10e6 cells | |
| | | | 68.5% | WBCs | 10 nmol/10e6 cells | |
| | | | 83.9% | WBCs | 100 nmol/10e6 cells | |
| | | | 9.0% | WBCs | 350 pmol/10e6 cells | 0.001% Tween20 |
| | | | 10.0% | WBCs | 350 pmol/10e6 cells | 0.0003% Tween20 |
| | | | 10.0% | WBCs | 350 pmol/10e6 cells | 0.0001% Tween21 |
| | | | 15.0% | WBCs | 350 pmol/10e6 cells | 0.00003% Tween22 |
| | | | 75.0% | WBCs | 100 nmol/10e6 cells | |
| | | | 44.0% | WBCs | 5 nmol/10e6 cells | |
| | | | 25.0% | WBCs | 0.5 nmol/10e6 cells | |
| | | | 66.0% | WBCs | 100 nmol/10e6 cells | |
| | | | 34.0% | WBCs | 5 nmol/10e6 cells | |
| | | | 27.0% | WBCs | 0.5 nmol/10e6 cells | may be to due 1.5-2 h |
| | | | 33.0% | WBCs | 100 nmol/10e6 cells | exposure of plate |
| Cholesteryl-TEG-Cholesteryl-TEG-(SpacerC18)7-Biotin-TEG | 5'-XXYYYYYYTZ-3' (Y = Spacer C18) | 29.891234 | 16.0% 38.0% | WBCs WBCs | 5 nmol/10e6 cells 0.5 nmol/10e6 cells | |
| Cholesteryl-TEG-Cholesteryl-TEG-(SpacerC18)7-Biotin-TEG | 5'-XXYYYYYYYTZ-3' (Y = Spacer C18) | 29.891234 | 18.0% 42.0% | WBCs WBCs | 350 pmol/10e6 cells 1000 pmol/10e6 cells | not evaporated. VIVA Spin nicht not evaporated. VIVA |
| 5'-(Cholesteryl-TEG)2-(SpacerC18)7-dT-Biotin-TEG-3' | 5'-YY XXXXXXTZ-3' (X = SpacerC18) | 29.891234 | 19.0% 45.0% | WBCs WBCs | 350 pmol/10e6 cells 1000 pmol/10e6 cells | not evaporated. VIVA Spin not evaporated. VIVA Spin |
| 5'-(Cholesteryl-TEG)2-(SpacerC18)7-dT-Biotin-TEG-3' | 5'-YY XXXXXXTZ-3' (X = SpacerC18) | 29.891234 | 7.0% 13.0% | WBCs WBCs | 350 pmol/10e6 cells 1 nmol/10e6 cells | |
| 5'-(Cholesteryl-TEG)2-(SpacerC18)7-dT-Biotin-TEG-3' | 5'-YY XXXXXXTZ-3' (X = SpacerC18) | 29.891234 | 63.0% 71.0% | WBCs WBCs | 350 pmol/10e6 cells 1 nmol/10e6 cells | |
| 5'-(Cholesteryl-TEG)2-(SpacerC18)7-dT-Biotin-TEG-3' | 5'-YY XXXXXXTZ-3' (X = SpacerC18) | 29.891234 | 52.0% 78.0% | WBCs WBCs | 350 pmol/10e6 cells 1 nmol/10e6 cells | |
| 5'-(Cholesteryl-TEG)2-(SpacerC18)7-SpacerC3-dT-Biotin-TEG-3' | 5'-YY XXXXXXWTZ-3' (W = Spacer C3, X = SpacerC18) | 29.891234 | 33.0% 44.0% | WBCs WBCs | 350 pmol/10e6 cells 1 nmol/10e6 cells | |
| 5'-(Cholesteryl-TEG)2-SpacerC3-dT-Biotin-TEG-3' | 5'-YY XXXXXXWTZ-3' (W = Spacer C3, X = SpacerC18) | 29.891236 | 46.0% 64.0% | WBCs WBCs | 350 pmol/10e6 cells 1 nmol/10e6 cells | |
| 5'-(Cholesteryl-TEG)2-(SpacerC18)7- | 5'-YY XXXXXXWTZ-3' | 29.891236 | 37.0% 47.0% | WBCs WBCs | 350 pmol/10e6 cells 1 nmol/10e6 cells | |

| tested compound | modular structure | Internal Reference number | Recovery Rate | cells | concentration |
|---|---|---|---|---|---|
| SpacerC3-dT-Biotin-TEG-3' | (W = Spacer C3, X = SpacerC18) | | | | |
| 5'-(Cholesteryl-TEG)2-(SpacerC18)7-SpacerC3-dT-Biotin-TEG-3' | 5'-YY XXXXXXWTZ-3' (W = Spacer C3, X = SpacerC18) | 29.891237 | 8.1% 15.1% 41.3% 59.1% | WBCs WBCs WBCs WBCs | 10 pmol/10e6 cells 100 pmol/10e6 cells 1 nmol/10e6 cells 10 nmol/10e6 cells |
| 5'-(Cholesteryl-TEG)2-(SpacerC18)7-SpacerC3-dT-Biotin-TEG-3' | 5'-YY XXXXXXWTZ-3' (W = Spacer C3, X = SpacerC18) | 29.891237 | 10.5% 16.4% 35.4% 62.0% | WBCs WBCs WBCs WBCs | 10 pmol/10e6 cells 100 pmol/10e6 cells 1 nmol/10e6 cells 10 nmol/10e6 cells |
| 5'-(Cholesteryl-TEG)-(SpacerC18)7-dT-Biotin-TEG-3' | 5'-Y XXXXXXXTZ-3' (W = Spacer C3, X = SpacerC18) | 29.891244 | 14.00% 27.00% 51.00% 57.00% | WBCs WBCs WBCs WBCs | 10 pmol/10e6 cells 100 pmol/10e6 cells 1 nmol/10e6 cells 10 nmol/10e6 cells |
| 5'-(Cholesteryl-TEG)2-(SpacerC18)7-dT-Biotin-TEG-3' | 5'-YY XXXXXXXTZ-3' (W = Spacer C3, X = SpacerC18) | 29.891246 | 9.50% 20.50% 50.70% 68.90% | WBCs WBCs WBCs WBCs | 10 pmol/10e6 cells 100 pmol/10e6 cells 1 nmol/10e6 cells 10 nmol/10e6 cells |
| 5'-(SpacerC18)7-dT-Biotin-TEG-3' | 5'-Y XXXXXXXTZ-3' (W = Spacer C3, X = SpacerC18) | 29.891245 | 9.30% 6.20% 8.40% 27.50% | WBCs WBCs WBCs WBCs | 10 pmol/10e6 cells 100 pmol/10e6 cells 1 nmol/10e6 cells 10 nmol/10e6 cells |
| 5'-(Cholesteryl-TEG)2-(SpacerC18)7-dT-Biotin-TEG-3' | 5'-YY XXXXXXXTZ-3' (W = Spacer C3, X = SpacerC18) | 29.891246 | 74.50% | WBCs | 10 nmol/10e6 cells |
| 5'-(Cholesteryl-TEG)-(SpacerC18)7-dT-Biotin-TEG-3' | 5'-Y XXXXXXXTZ-3' (W = Spacer C3, X = SpacerC18) | 29.891244 | 51.70% | | 10 nmol/10e6 cells |
| 5'-(SpacerC18)7-dT-Biotin-TEG-3' Mixture of 44 + 45 + 46 | 5'-XXXXXXXTZ-3' (W = Spacer C3, X = SpacerC18) | 29.891245 | 24.70% 66.90% | | 10 nmol/10e6 cells 10 nmol/10e6 cells |
| 5'-(Cholesteryl-TEG)2-(SpacerC18)7-dT-Biotin-TEG-3' | 5'-YY XXXXXXXTZ-3' (W = Spacer C3, X = SpacerC18) | 29.891246 | 87.16% | | 10 nmol/10e6 cells |
| 5'-(Cholesteryl-TEG)-(SpacerC18)7-dT-Biotin-TEG-3' | 5'-Y XXXXXXXTZ-3' (W = Spacer C3, X = SpacerC18) | 29.891244 | 63.70% | | 10 nmol/10e6 cells |

-continued

| tested compound | modular structure | Internal Reference number | Recovery Rate | cellsconcentration |
|---|---|---|---|---|
| 5'-(SpacerC18)7-dT-Biotin-TEG-3' Mixture of 44 + 45 +46 | 5'-XXXXXXXTZ-3' (W = Spacer C3, X = SpacerC18) | 29.891245 | 26.50% | 10 nmol/10e6 cells |
| | | | 79.46% | 10 nmol/10e6 cells |
| 5'-(SpacerC18)-dT-Biotin-TEG-3' | 5'-XTZ-3' (W = Spacer C3, X = SpacerC18) | 29891240 | 12.80% | 1 nmol/10e6 cells |
| | | | 14.90% | 10 nmol/10e6 cells |
| 5'-(Cholesteryl-TEG)2- (SpacerC18)7-dT-Biotin-TEG-3' | 5'-YY XXXXXXXTZ-3' (W = Spacer C3, X = SpacerC18) | 29.891246 | 85.50% | 1 nmol 1C18 + 10 nmol CholChol |
| Mix | DSPE-PEG(2000) | | 83.22% | 10 nmol 1C18 + 10 nmol CholChol |
| 1.2 Distearoyl-sn-glycero-3-phosphoethanolamine-N-[biotinyl(PEG2000] | Biotin (Avantilipids) | | 70.80% | 10 nmol/10^6 Distearine without EDTA-K |
| | | | 71.60% | 10 nmol/10^6 EDTA-K |
| | | | 76.50% | 10 nmol/10^6 Distearine 1 mM EDTA-K |
| | | | 72.00% | 10 nmol/10^6 Distearine 3 mM EDTA-K |
| | | | 78.30% | 10 nmol/10^6 Distearine without EDTA-K |
| | | | 82.70% | 10 nmol/10^6 Distearine 0.3 mM EDTA-K |
| | | | 81.80% | 10 nmol/10^6 EDTA-K |
| | | | 68.90% | 10 nmol/10^6 Distearine 1 mM EDTA-K |
| | | | 69.60% | 10 nmol/10^6 EDTA-K |
| | | | 68.90% | 10 nmol/10^6 Distearine 3 mM EDTA-K |
| | | | 95.90% | 10 pmol/10e6 cells |
| | | | 84.40% | 100 pmol/10e6 cells |
| | | | 90.80% | 10 nmol/10e6 cells |
| 1.2- Dioleyl-sn-Glycero-3-Phosphoethanolamin-N-(Cap-Biotin)-Na | Avantilipids | | 66.30% | 10 pmol/10e6 cells |
| | | | 91.10% | 100 pmol/10e6 cells |
| | | | 95.80% | 1 nmol/10e6 cells |

-continued

| tested compound | modular structure | Internal Reference number | Recovery Rate | cellsconcentration |
|---|---|---|---|---|
| | | | 20.60% | without Linker |
| | | | 74.40% | 10 pmol/10e6 cells |
| | | | 107.10% | 100 pmol/10e6 cells |
| | | | 101.76% | 1 nmol/10e6 cells |
| | | | 26.85% | without Linker |
| | | | 81.00% | 100 pmol/10e6 cells |
| | | | 80.10% | 100 pmol/10e6 cells |
| | | | 64.90% | 100 pmol/10e6 cells |
| | | | 80.55% | 100 pmol/10e6 cells |
| | | | 70.85% | 100 pmol/10e6 cells |
| | | | 80.74% | 100 pmol/10e6 cells |
| | | | 53.97% | 100 pmol/10e6 cells |
| | | | 69.60% | 100 pmol/10e6 cells |
| | | | 80.16% | 500 pmol/10e6 cells |
| | | | 95.94% | 500 pmol/10e6 cells |
| | | | 89.19% | 10 nmol/10e6 cells |
| | | | 105.12% | 10 nmol/10e6 cells |
| Dipalmityl-sn-Glycero-3-Phosphoethanolamin-N-(Cap-Biotin)-Na | Avantilipids | | 54.30% | 10 pmol/10e6 cells |
| | | | 72.20% | 100 pmol/10e6 cells |
| | | | 84.90% | 1 nmol/10e6 cells |
| | | | 11.10% | without Linker |
| | | | 45.40% | 100 pmol/10e6 cells |
| | | | 86.10% | 100 pmol/10e6 cells |
| | | | 89.30% | 1 nmol/10e6 cells |
| | | | 14.10% | without Linker |
| | | | 51.80% | 300 pmol/10e6 cells |
| | | | 55.90% | 300 pmol/10e6 cells |
| | | | 52.60% | 300 pmol/10e6 cells |
| | | | 73.07% | 300 pmol/10e6 cells |
| | | | 61.27% | 300 pmol/10e6 cells |
| | | | 71.40% | 300 pmol/10e6 cells |
| 5'-(Cholesteryl-TEG)2-PEG2000-Fluos-Biotin_TEG-3' | purified | 29.891.247 | 13.38% | 10 pmol/10e6 cells |
| | | | 15.26% | 100 pmol/10e6 cells |
| | | | 13.27% | 1 nmol/10e6 cells |
| | | | 45.75% | 10 nmol/10e6 cells |
| 5'-(Cholesteryl-TEG)2-Spacer C18-Fluos-Biotin_TEG-3' | purified | 29.891.251 | 25.57% | 10 pmol/10e6 cells |
| | | | 57.82% | 100 pmol/10e6 cells |
| | | | 89.71% | 1 nmol/10e6 cells |
| | | | 92.63% | 10 nmol/10e6 cells |
| | | | 68.57% | 100 nmol/10e6 cells |
| | | | 82.61% | 1 nmol/10e6 cells |
| 5'-(Cholesteryl-TEG)2-PEG2000-Fluos-Biotin_TEG-3' INVERS | purified | 29.891248 | 32.80% | 10 pmol/10e6 cells |
| | | | 65.36% | 100 pmol/10e6 cells |
| | | | 83.99% | 1 nmol/10e6 cells |

-continued

| tested compound | modular structure | Internal Reference number | Recovery Rate | cellsconcentration |
|---|---|---|---|---|
| 5'-(Cholesteryl-TEG)2-Spacer C18-Fluos-Biotin_TEG-3' INVERS | purified | 29.891254 | 81.10%<br>70.75%<br>86.03%<br>40.30%<br>64.60%<br>92.50%<br>83.60%<br>57.63%<br>82.19%<br>65.69%<br>81.79%<br>70.07%<br>81.28%<br>74.68% | 10 nmol/10e6 cells<br>100 pmol/10e6 cells<br>1 nmol/10e6 cells<br>10 pmol/10e6 cells<br>100 pmol/10e6 cells<br>1 nmol/10e6 cells<br>10 pmol/10e6 cells<br>100 pmol/10e6 cells<br>1 nmol/10e6 cells<br>100 pmol/10e6 cells<br>1 nmol/10e6 cells<br>100 pmol/10e6 cells<br>100 pmol/10e6 cells<br>1 nmol/10e6 cells |
| 3'-(Myristic acid)2-PEG2000-dT-Biotin-TEG-5' INVERS | unpurified | 29.891255 | 24.70%<br>50.61%<br>87.55%<br>83.53% | 10 pmol/10e6 cells<br>100 pmol/10e6 cells<br>1 nmol/10e6 cells<br>10 nmol/10e6 cells |
| 3'-(Myristic acid)2-PEG2000-Fluos-Biotin-TEG-5' INVERS | unpurified | 29.891256 | 35.79%<br>73.42%<br>85.13% | 10 pmol/10e6 cells<br>100 pmol/10e6 cells<br>1 nmol/10e6 cells |
| 5'-(Cholesteryl-TEG)2-Spacer C18-dT-Biotin-PEG2000-dT-Biotin_TEG-3' | unpurified | 29.891249 | 11.38%<br>16.16%<br>37.73%<br>61.04% | 10 pmol/10e6 cells<br>100 pmol/10e6 cells<br>1 nmol/10e6 cells<br>10 nmol/10e6 cells |
| 5'-(Cholesteryl-TEG)2-Spacer C18-dT-Biotin_TEG-3' INVERS | unpurified | 29.891252 | 28.56%<br>55.41%<br>71.99%<br>88.05%<br>16.03%<br>52.46%<br>80.83%<br>85.47% | 10 pmol/10e6 cells<br>100 pmol/10e6 cells<br>1 nmol/10e6 cells<br>10 nmol/10e6 cells<br>10 pmol/10e6 cells<br>100 pmol/10e6 cells<br>1 nmol/10e6 cells<br>10 nmol/10e6 cells |
| 5'-(Cholesteryl-TEG)2-Spacer C12-dT-Biotin_TEG-3' INVERS | unpurified | 29.891253 | 47.42%<br>73.46%<br>96.84%<br>102.36% | 10 pmol/10e6 cells<br>100 pmol/10e6 cells<br>1 nmol/10e6 cells<br>10 nmol/10e6 cells |

-continued

| tested compound | modular structure | Internal Reference number | Recovery Rate | cellsconcentration | |
|---|---|---|---|---|---|
| 5'-(Chol-TEG)1-Doubler-dT-Biotin-3' | | | 41.44% | 100 pmol/10e6 cells | |
| | | | 72.13% | 1 nmol/10e6 cells | |
| | | | 62.59% | 100 pmol/10e6 cells | |
| | | | 79.02% | 1 nmol/10e6 cells | Vesicle formation |
| | | 29.891272 | 65.03% | 10 pmol/10e6 cells | |
| | | | 83.08% | 100 pmol/10e6 cells | |
| | | | 87.93% | 1 nmol/10e6 cells | |
| | | | Cells lysed | 10 nmol/10e6 cells | |
| | | | 56.49% | 100 pmol/10e6 cells | |
| | | | 72.13% | 1 nmol/10e6 cells | |
| | | | 62.11% | 100 pmol/10e6 cells | |
| | | | 82.47% | 1 nmol/10e6 cells | |
| | | | 82.01% | 100 pmol/10e6 cells | |
| 5'-(Cholesteryl-TEG)2-PEG2000-dT-Biotin_TEG-3' | purified | 29.891249 | 50.49% | 100 pmol/10e6 cells | |
| | | | 87.24% | 1 nmol/10e6 cells | |
| 5'-(Cholesteryl-TEG)2-PEG2000-Fluos-Biotin_TEG-3' INVERS | purified | 29.891250 | 48.66% | 100 pmol/10e6 cells | |
| | | | 81.29% | 1 nmol/10e6 cells | |
| 5'-(Cholesteryl-TEG)2-Spacer C18-dT-Biotin_TEG-3' INVERS | purified | 29.891252 | 28.18% | 100 pmol/10e6 cells | |
| | | | 61.88% | 1 nmol/10e6 cells | |
| 5'-(Cholesteryl-TEG)2-Spacer C12-dT-Biotin_TEG-3' INVERS | purified | 29.891253 | 71.41% | 100 pmol/10e6 cells | |
| | | | 86.21% | 1 nmol/10e6 cells | |

B)

| Molecule/combination thereof tested | Internal number | Recovery rate treated cells (SA-plate) | Recovery rate untreated cells (SA plate) | Recovery rate treated cells (untreated-plate) | Recovery rate untreated cells (ntreated plate) | Remarks |
|---|---|---|---|---|---|---|
| Cholesterol- Compound (5'-XXYFZ-3') | 29.891180 | 73.2% | 16.3% | 56.7% | 68.7% | strong staining |
| Boronic acid- Compound (single) | 15.260267 | 16.3% | 13.0% | 32.5% | 41.3% | |
| Cholesterol- Compound (5'-XXYFZ-3') | 29.891180 | 71.7% | 24.4% | | | |
| Distearoyl- Compound (Avanti) | | 53.8% | | | | |
| Chol-Compound + Distearoyl-Compound | 29.891180 | 74.7% | | | | |
| Cholesterol- Compound (5'-XXYFZ-3') | 29.891180 | 83.2% | 30.6% | | | |
| Distearoyl- compound (Avanti) | | 66.7% | | | | |
| Chol-Compound + Distearoyl-Compound | 29.891180 | 80.2% | | | | |
| Cholesterol- Compound 200 µl Zellsus. | 29.891180 | 67.6%/71.9% | | | | |
| Cholesterol- Compound 400 µl Zellsus. | 29.891180 | 78.4%/84.1% | | | | |
| Cholesterol- Compound 800 µl Zellsus. | 29.891180 | 81.1%/86.4% | | | | |
| Cholesterol- Compound (5'-XXYFZ-3') | 29.891180 | 80.9% | 30.8% | | | |
| Distearoyl- Compound (Avanti) | | 50.6% | | | | |
| Chol-Compound + Distearoyl-Compound | 29.891180 | 77.8% | | | | |
| Myristic acid-Compound (5'-XXYFZ-3')C1 | 29.891194 | 20.7% | 21.6% | | | weak Staining |
| Myristic acid-Compound (5'-XXYFZ-3')C2 | 29.891194 | 22.1% | | | | |
| Myristic acid-Compound (5'-XXYFZ-3')C1 | 29.891194 | 33.1% | 19.5% | | | stronger Staining |
| Myristic acid-Compound (C14-Lys-PEG) | 15.260268 | 47.7% | 19.5% | | | |
| Cholesterol- Compound (5'-XXYFZ-3') | 29.891194 | 63.4% | 10.7% | | | |
| Myristic acid-Compound (C14-Lys-PEG) | 15.260268 | 53.9% | | | | |
| Chol-Compound + Myr.-Compound | 29.891194/15.260268 | 43.6% | | | | |
| Chol-Compound + Myr.-Compound | 29.891194/15.260268 | 43.6% | | | | |
| Chol-Compound 2.16 µg/2 × 10e6 WBCs | 29.891180 | 78.6% | | | | |
| Chol-Compound 21.6 µg/2 × 10e6 WBCs | 29.891180 | 68.6% | | | | |
| Chol-Compound 216 µg/2 × 10e6 WBCs | 29.891180 | 50.1% | | | | |
| Myr-Compound 2.16 µg/2 × 10e6 WBCs | 15.260268 | 39.6% | | | | higher conc. will be tested again |
| Myr-Compound 21.6 µg/2 × 10e6 WBCs | 15.260268 | 46.7% | | | | |
| Myr-Compound 216 µg/2 × 10e6 WBCs | 15.260268 | 51.8% | | | | |
| Cholesterol- Compound (5'-XXYFZ-3') | 29.891194 | 89.6% | | | | |
| Distearoyl- Compound (Avanti) | | 82.6% | | | | |
| Myristic acid.-Compound (C14-Lys-PEG) | 15.260268 | 85.7% | | | | |
| Chol-Compound + Distearoyl-Compound | 29.891194 | 84.3% | | | | |
| Chol-Compound + Myr.-Compound | 29.891194/15.260268 | 91.3% | | | | |
| Chol + Distearoyl + Myr | 29.891194/15.260268 | 87.0% | | | | |
| Cholesterol- Compound (5'-XXYFZ-3') | 29.891194 | 74.0% | | | | |
| Distearoyl- Compound (Avanti) | | 53.5% | | | | |
| Myristic acid.-Compound (C14-Lys-PEG) | 15.260268 | 45.6% | | | | |
| Chol-Compound + Distearoyl-Compound | 29.891194 | 71.7% | | | | |
| Chol-Compound + Myr.-Compound | 29.891194/15.260268 | 68.4% | | | | |
| Chol + Distearoyl + Myr | 29.891194/15.260268 | 64.9% | | | | |
| Chol- Compound 10 min 4° C. | 29.891194 | 81.6% | | | | |
| Chol- Compound 60 min 4° C. | 29.891194 | 81.7% | | | | |
| Chol- Compound 10 min RT | 29.891194 | 88.3% | | | | |

-continued

| Molecule/combination thereof tested | Internal number | Recovery rate treated cells (SA-plate) | Recovery rate untreated cells (SA plate) | Recovery rate treated cells (untreated-plate) | Recovery rate untreated cells (ntreated plate) | Remarks |
|---|---|---|---|---|---|---|
| Chol- Compound 60 min RT | 29.891194 | 85.5% | | | | |
| Chol- Compound 10e4 MDAs in WBCs | 29.891194 | 99.0% | | | | |
| Chol- Compound 5 × 10e5 WBCs | 29.891194 | 70.0% | | | | |
| Chol- Compound 20e3 MDAs in WBCs | 29.891194 | 102.0% | | | | |
| Chol- Compound 5 × 10e5 WBCs | 29.891194 | 70.8% | | | | |
| Chol- Compound 40e3 MDAs in WBCs | 29.891194 | 102.0% | | | | |
| Chol- Compound 10e6 WBCs | 29.891194 | 69.4% | | | | |
| Myr-Myr-C18-Fluos | 29.891213 | 67.4% | | | | strong staining |
| Myr-Myr-PEG-Fluos | 29.891194 | 24.4% | | | | weak staining |
| Myr-Myr-7xC18-Fluos | 29.891214 | 78.9% | | | | strong staining |
| Myr-C9-Myr-PEG-Fluos | 29.891197 | not enough material | | | | weak staining |

C) Comparison of Results Obtained Upon Pretreatment of Either the Wells of the Plate or the Cells with Molecules Useful in Methods of the Invention The experiments were performed for different incubation times, as shown below:

| 30 min Well | target: 300.000 WBC | | MW | Standard deviation | Mean % | Standard deviation % |
|---|---|---|---|---|---|---|
| a1 | Well treated | 61470 | 64909 | 8131.2 | 21.64 | 2.71 |
| a2 | Well treated | 67259 | | | | |
| a3 | Well treated | 74951 | | | | |
| a4 | Well treated | 55956 | | | | |
| b1 | untreated | 55575 | 29059.75 | 19683.1 | 9.69 | 6.56 |
| b2 | untreated | 32017 | | | | |
| b3 | untreated | 17166 | | | | |
| b4 | untreated | 11481 | | | | |
| c1 | WBC treated | 213072 | 231829.75 | 13176.7 | 77.28 | 4.39 |
| c2 | WBC treated | 237475 | | | | |
| c3 | WBC treated | 243445 | | | | |
| c4 | WBC treated | 233327 | | | | |

| 90 min Well | target: 300.000 WBC | | MW | Standard deviation | Mean % | Mean % |
|---|---|---|---|---|---|---|
| a1 | Well treated | 124492 | 142865 | 13000.28 | 47.62 | 4.33 |
| a2 | Well treated | 143548 | | | | |
| a3 | Well treated | 154212 | | | | |
| a4 | Well treated | 149208 | | | | |
| b1 | untreated | 46601 | 27972 | 13732.98 | 9.32 | 4.58 |
| b2 | untreated | 29206 | | | | |
| b3 | untreated | 21199 | | | | |
| b4 | untreated | 14882 | | | | |
| c1 | WBC treated | 237185 | 249346.25 | 8160.72 | 83.12 | 2.72 |
| c2 | WBC treated | 252944 | | | | |
| c3 | WBC treated | 254697 | | | | |
| c4 | WBC treated | 252559 | | | | |

| 120 min Well | target: 300.000 WBC | | MW | Standard deviation | Mean % | Mean % |
|---|---|---|---|---|---|---|
| a1 | Well treated | 167671 | 171062.75 | 19104.5 | 57.02 | 6.37 |
| a2 | Well treated | 177678 | | | | |
| a3 | Well treated | 192194 | | | | |
| a4 | Well treated | 146708 | | | | |
| b1 | untreated | 46402 | 29214.5 | 14633.3 | 9.74 | 4.88 |
| b2 | untreated | 35669 | | | | |
| b3 | untreated | 20989 | | | | |
| b4 | untreated | 13798 | | | | |
| c1 | WBC treated | 256949 | 258692.75 | 7300.9 | 86.23 | 2.43 |
| c2 | WBC treated | 268552 | | | | |
| c3 | WBC treated | 258291 | | | | |
| c4 | WBC treated | 250979 | | | | |

The results on immobilization are summarized as follows:

| | 30 min | | 90 min | | 120 min | |
|---|---|---|---|---|---|---|
| | WBC recovery rate [%] | Standard deviation | WBC recovery rate [%] | Standard deviation | WBC recovery rate [%] | Standard deviation |
| molecule useful in methods invention bound to surface | 21.64 | 2.71 | 47.6 | 4.33 | 57.02 | 6.37 |
| molecule useful in methods of invention + cells | 77.28 | 4.39 | 83.1 | 2.72 | 86.23 | 2.43 |
| untreated | 9.69 | 6.56 | 9.3 | 4.58 | 9.74 | 4.88 |

|  | 30 min | 90 min | 120 min |
|---|---|---|---|
| molecule useful in methods of invention bound to surface | 21.64 | 47.6 | 57.02 |
| molecule useful in methods of invention + cells | 77.28 | 83.1 | 86.23 |
| untreated | 9.69 | 9.3 | 9.74 |

D) Determination of Recovery Rate for Exemplary Compound Biotin-PEG-Lys-(C14)2:

The following recovery rate was determined for compound Biotin-PEG-lys-(C14)2:

M=2708.90 g/mol 5.4 mg/10 ml EtOH c=n/V=m/M*V c=5.4 g/(2708.9 g/mol*10 l)=1.99 10e-4 mol/l 1.99*10e-4 mol/l=7.96 nmol/4 µl 4 µl=4.5*10e6 Cells →1.77 nmol/10e6 Cells Recovery rate in this experiment: 85.72%

Example 4

Comparison of Compounds Useful in Methods of the Invention Containing One Vs. Two Hydrophobic Moieties Aim of this experiment: Testing of the white blood cell immobilization on a streptavidin-coated surface using different molecules useful in methods of the invention. In particular, the performance of a single cholesterol-molecule and different dual-linker molecules (i.e. containing two hydrophobic moieties) was tested. In detail, immobilization of white blood cells (WBCs) on a Streptavidin-coated surface using different linker molecules was tested on a 12-well plate: 300,000 WBCs/well. This was followed by the measurement of the cell recovery rate after immobilization and washing of the cells using the Cellavista instrument (10× Nuclei Operator s9s5).

The results are as follows:

Sample 1

| compound internal reference No. |  | Mean standard deviation | Recovery rate | standard deviation |
|---|---|---|---|---|
| A1 | 29.891253 | 105061 | 17632.25 | 41.44% | 5.88% |
| B1 | 29.891253 | 128195 |  |  |  |
| C1 | 29.891253 | 139678 |  |  |  |
| A2 | 29.891254 | 157660 | 16339.42 | 57.63% | 5.45% |
| B2 | 29.891254 | 190148 |  |  |  |
| C2 | 29.891254 | 170850 |  |  |  |
| A3 | 29.891272 | 147132 | 19366.19 | 56.49% | 6.46% |
| B3 | 29.891272 | 179643 |  |  |  |
| C3 | 29.891272 | 181620 |  |  |  | compound concentration: 1 nmol/10e6 WBCs

| compound internal reference No. |  | Mean standard deviation | Recovery rate | standard deviation |
|---|---|---|---|---|
| A1 | 29.891253 | 218861 | 6689.53 | 72.13% | 2.23% |
| B1 | 29.891253 | 221471 |  |  |  |
| C1 | 29.891253 | 208802 |  |  |  |
| A2 | 29.891254 | 244649 | 13351.64 | 82.19% | 4.45% |
| B2 | 29.891254 | 234262 |  |  |  |
| C2 | 29.891254 | 260760 |  |  |  |
| A3 | 29.891272 | 199973 | 14735.92 | 72.13% | 4.91% |
| B3 | 29.891272 | 220701 |  |  |  |
| C3 | 29.891272 | 228481 |  |  |  |

Sample 2

A) Compound Concentration: 100 pmol/10e6 WBCs

| compound internal reference No. | Mean | Mean standard deviation | Recovery rate | standard deviation |
|---|---|---|---|---|
| A1 | 29.891253 | 178919 | 187757.67 | 9117.22 | 62.59% | 3.04% |
| B1 | 29.891253 | 197130 |  |  |  |  |
| C1 | 29.891253 | 187224 |  |  |  |  |
| A2 | 29.891254 | 185100 | 197067.00 | 10752.84 | 65.69% | 3.58% |
| B2 | 29.891254 | 200184 |  |  |  |  |

| Molecule tested | Characteristics | Internal No | Structure |
|---|---|---|---|
| 5'-(Cholesterol-TEG)1-Doubler-dT-Biotin-3' | Mono-linker | 29.891272 | 5'—Y<br>　　＼<br>　　　XZ—3'<br>5'—／<br><br>Y = Cholesteryl-TEG<br>X = Doubler<br>Z = dTBiotin |
| 5'-(Cholesteryl-TEG)2-Spacer C12-dT-Biotin_TEG-3' INVERS | Dual linker | 29.891253 | 3'-YYXTZ-5'<br>Y = Cholesteryl-TEG<br>X = Spacer C12<br>Z = Biotin-TEG |
| 5'-(Cholesteryl-TEG)2-Spacer C18-Fluos-Biotin_TEG-3' INVERS | Dual linker | 29.891254 | 3'-YYXWZ-5'<br>Y = Cholesteryl-TEG<br>X = Spacer C18<br>W = Fluorescein<br>Z = Biotin-TEG |

-continued

| compound internal reference No. | Mean | Mean standard deviation | Recovery rate | standard deviation |
|---|---|---|---|---|
| C2 29.891254 | 205917 | | | |
| A3 29.891272 | 161504 | 186316.33 | 21657.26 62.11% | 7.22% |
| B3 29.891272 | 201424 | | | |
| C3 29.891272 | 196021 | | | |

B) Compound Concentration: 1 nmol/10e6 WBCs

| compound internal reference No. | Mean | Mean standard deviation | Recovery rate | standard deviation |
|---|---|---|---|---|
| A1 29.891253 | 239105 | 237052.33 | 4937.14 | 79.02% | 1.65% |
| B1 29.891253 | 240632 | | | | |
| C1 29.891253 | 231420 | | | | |
| A2 29.891254 | 244396 | 245376.00 | 1777.68 | 81.79% | 0.59% |
| B2 29.891254 | 244304 | | | | |
| C2 29.891254 | 247428 | | | | |
| A3 29.891272 | 241232 | 247418.33 | 6921.66 | 82.47% | 2.31% |
| B3 29.891272 | 254894 | | | | |
| C3 29.891272 | 246129 | | | | |

Conclusion: The Cholesterol-mono linker molecule (i.e. a compound containing a single hydrophobic moiety cholesterol) shows similar cell immobilization characteristics compared dual linker molecules (i.e. compounds containing two hydrophobic moieties).

Example 5

Stabilization of Cells Using Compounds Useful in Methods of the Invention

The effect of compounds useful in methods of the invention on stabilizing cells and on immobilization was determined.

Figure 14:
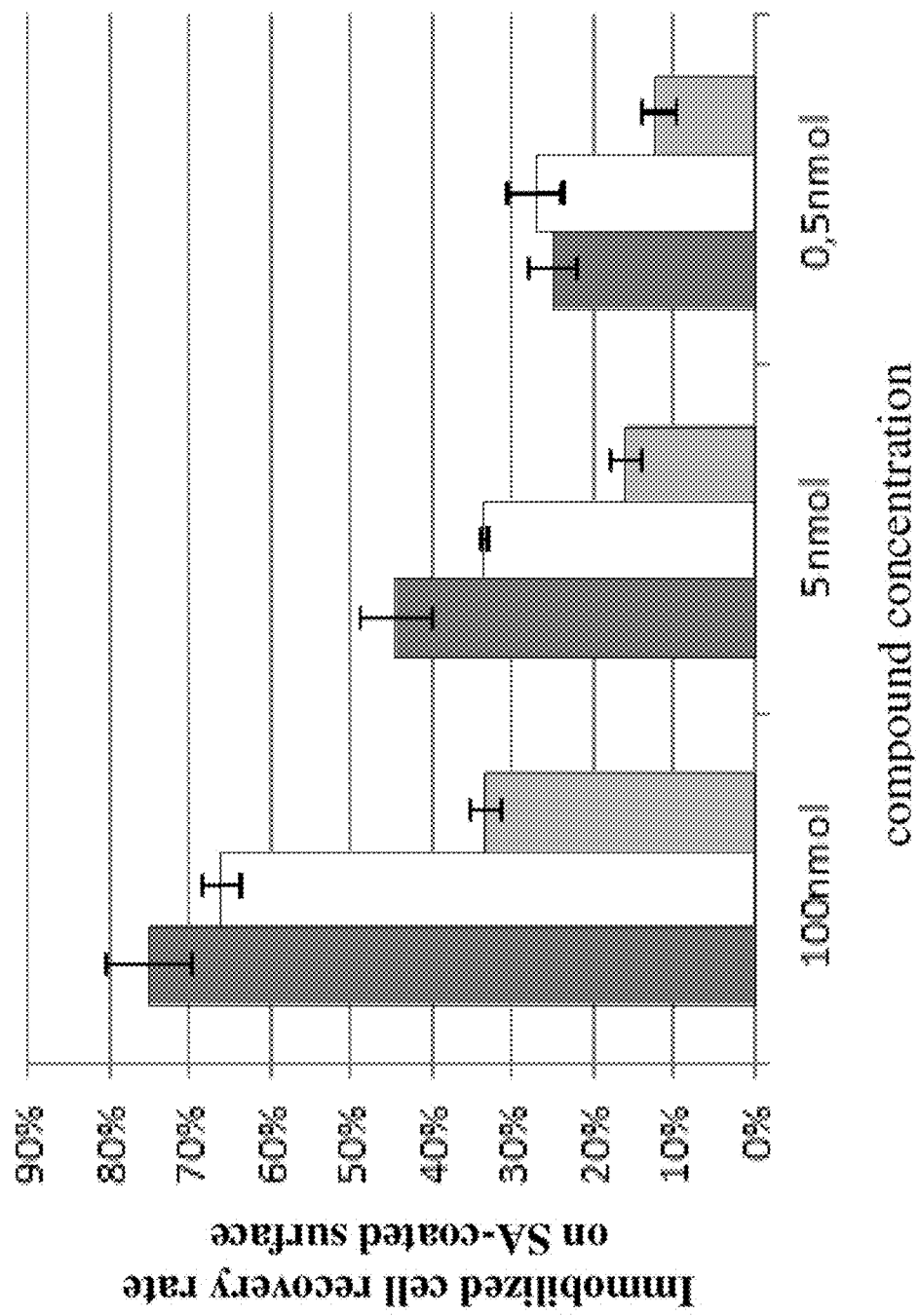
FIG. 14: shows WBC recovery rate after centrifugation and cell immobilization using different molecules. Molecule probes HH1749*, HH1750* and HH1755* show different performance concerning cell immobilization rate at different concentrations. The higher the compound concentration, the higher the cell immobilisation rate.
Figure 15:
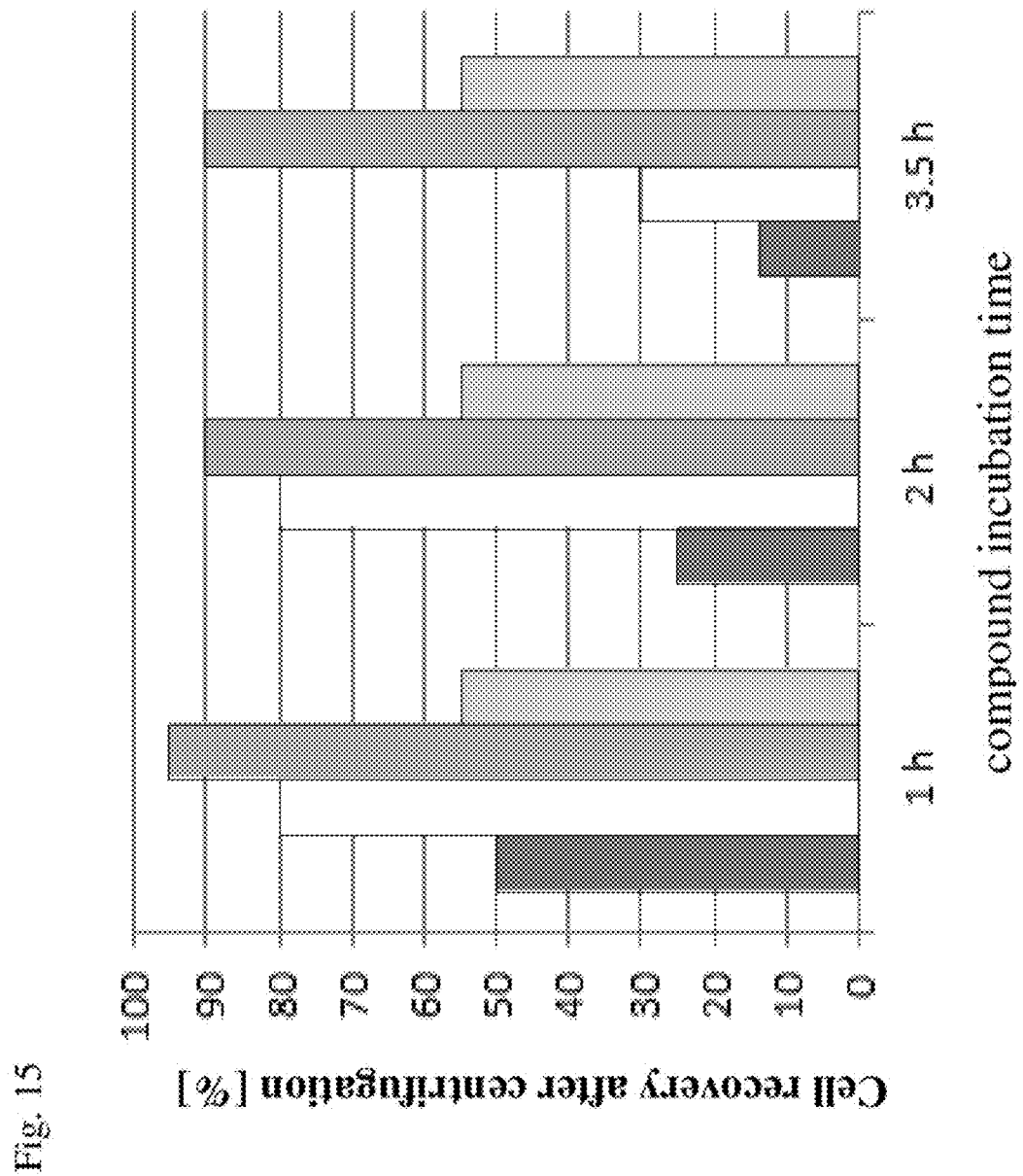
FIG. 15: shows WBC recovery rate after centrifugation using different compounds at different points of time. Molecules A and B (A: Cholesteryl-TEG-Cholesteryl-TEG-(SpacerC18)7-Fluos-Biotin-TEG; B: Biotin-PEG-Lysin-(C18)2) show different performance concerning recovery rate after centrifugation. Respective left column: w/o compound of invention; respective second column from left: 0.35 nmol molecule A; respective third column from left: 100 nmol molecule B; respective right column: 0.5 nmol molecule B. The higher the molecule concentration, the higher the cell recovery rate after centrifugation. Molecule B enables cell immobilization within 3.5 hours. Centrifugation characteristics: 10 min, 300×g.

A) WBC Recovery Rate After Centrifugation and Cell Immobilization Using Different Molecules As shown in FIG. 14, molecule probes HH1749*, HH1750* and HH1755* (* Biotin-PEG-Lysin-(C18)2) show different performance concerning recovery rate after centrifugation: The higher the concentration of the molecule, the higher the cell recovery rate after centrifugation. Centrifugation characteristics: 10 min, 300×g. As can be seen from FIG. 15, molecule probes HH1749*, HH1750* and HH1755* show different performance concerning cell immobilization rate at different concentrations. The higher the linker concentration, the higher the cell immobilisation rate.

Figure 16:
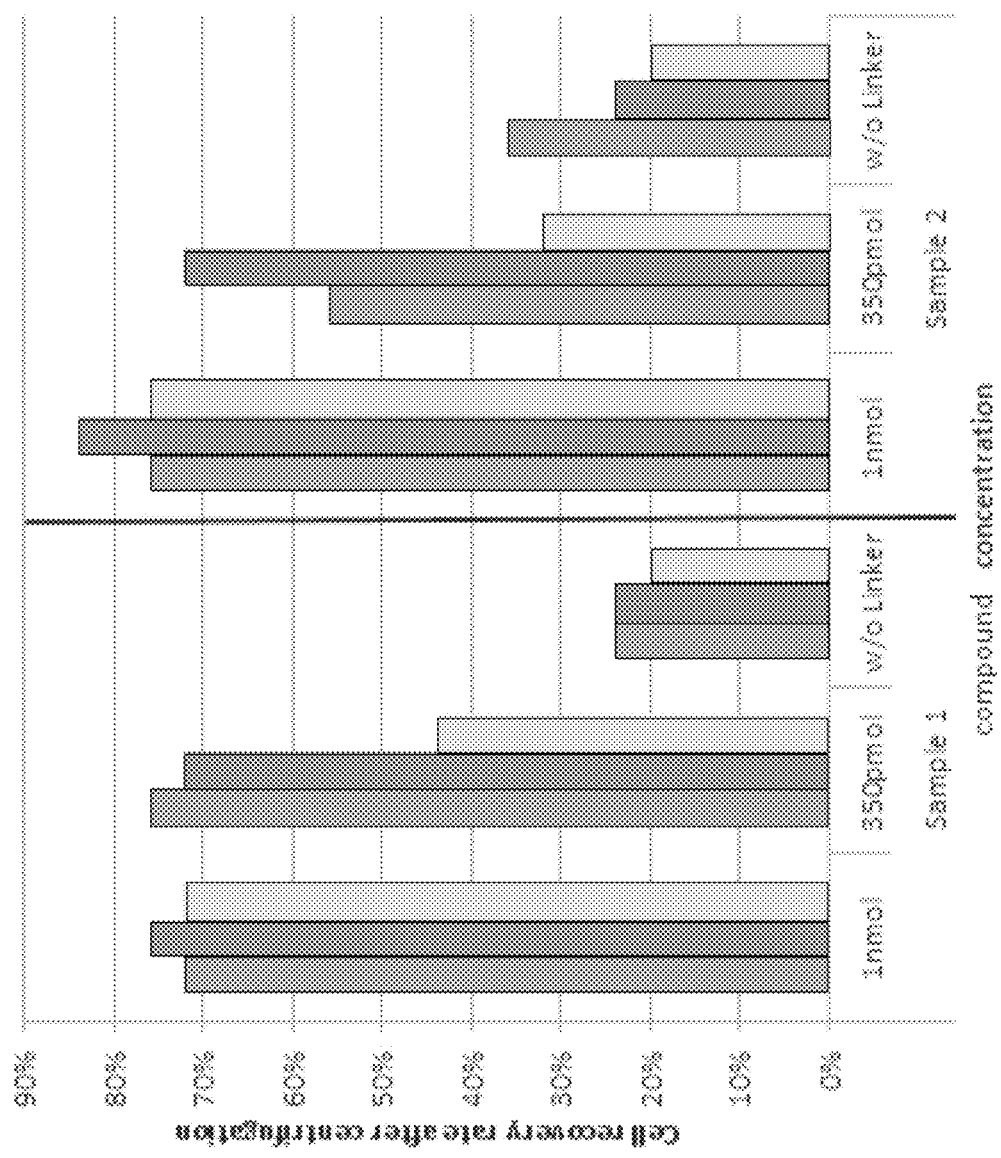
FIG. 16: shows WBC recovery rate after centrifugation with different experimenters. The respective left, middle and right columns per assay represent different Experimenters 1, 2 and 3. The higher the molecule concentration, the higher the cell recovery rate after centrifugation. Moreover, cell stabilization is independent on the experimenter. Centrifugation characteristics: 10 min, 300×g. Molecule: Cholesteryl-TEG-Cholesteryl-TEG-(SpacerC18)7-Fluos-Biotin-TEG.

B) WBC Recovery Rate After Centrifugation Using Different Compounds—Different Points of Time As can be seen from FIG. 16, molecules A and B (A: Cholesteryl-TEG-Cholesteryl-TEG-(SpacerC18)7-Fluos-Biotin-TEG; B: Biotin-PEG-Lysin-(C18)2) show different performance concerning recovery rate after centrifugation. The higher the molecule concentration, the higher the cell recovery rate after centrifugation. Molecule B enables cell immobilization within 3.5 hours. Centrifugation characteristics: 10 min, 300×g. A: Cholesteryl-TEG-Cholesteryl-TEG-(SpacerC18)7-Fluos-Biotin-TEG. B: Biotin-PEG-Lysin-(C18)2

C) WBC Recovery Rate After Centrifugation—Different Experimenters

Figure 17:
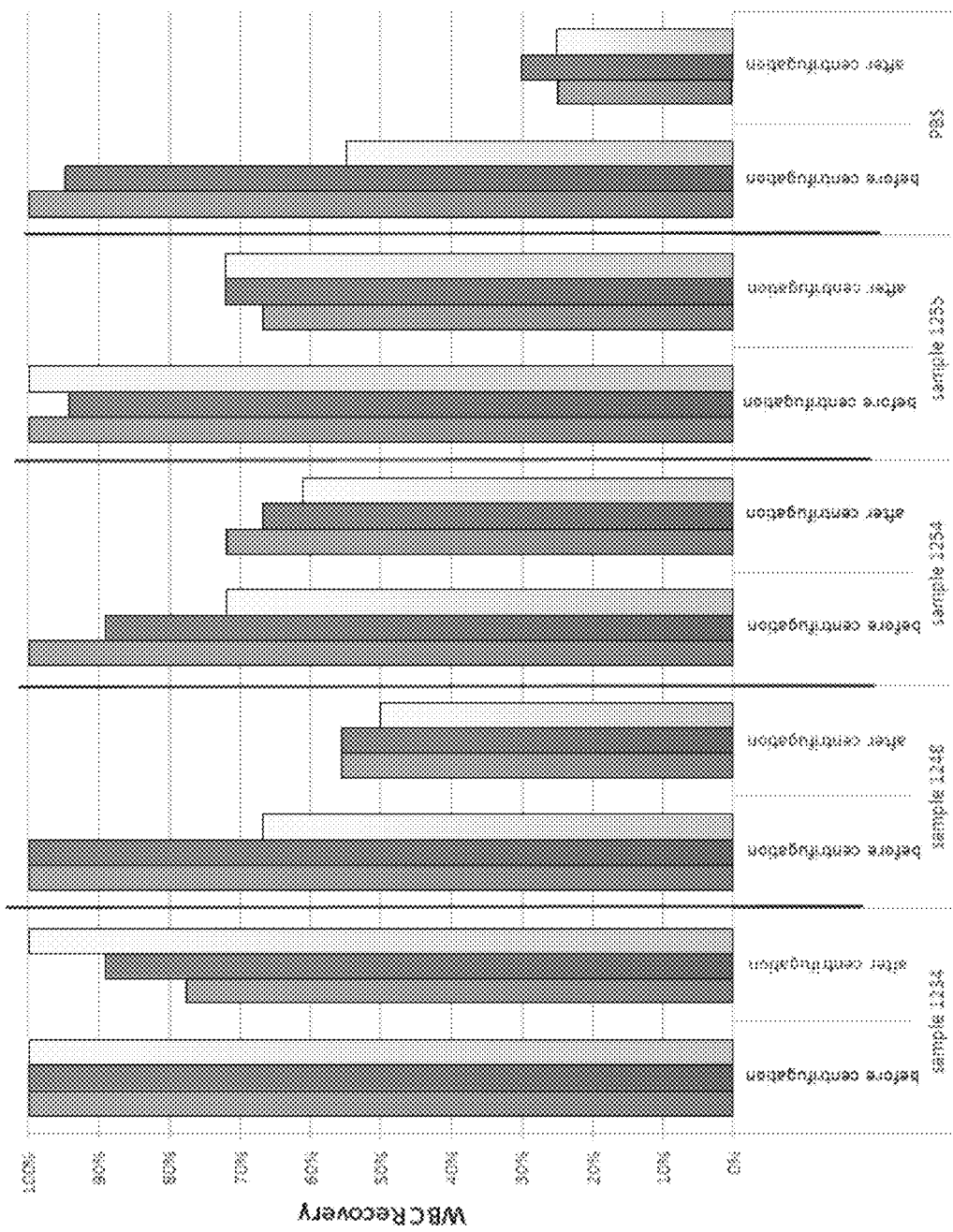
FIG. 17: shows WBC recovery rate after centrifugation at different points of time and centrifugation settings. Following molecules were tested: 1234: 5'-(Cholesteryl-TEG)2-Spacer C18-dT-Biotin-TEG-3'; 1248: 3'-(Cholesteryl-TEG)2-PEG2000-Fluos-Biotin-TEG-5' INVERS; 1254: 3'-(Cholesteryl-TEG)2-SpacerC18-Fluos-Biotin-TEG-5' INVERS; 1255: 3'-(Myristic acid)2-PEG2000-dT-Biotin-TEG-5' INVERS. All molecules enable cell immobilization within 2 hours. WBCs in PBS are damaged during centrifugation at 300×g for 20 min. Molecule 1234 shows the best performance followed by compound 1255 and 1254. Centrifugation characteristics: 20 min, 300×g. Respective left column: 10 min incubation with molecule. Respective middle column: 1 h min incubation with molecule. Respective right column: 2 h incubation with molecule.

As can be seen from FIG. 17, the higher the molecule concentration, the higher the cell recovery rate after centrifugation. Moreover, cell stabilization is independent on the experimenter. Centrifugation characteristics: 10 min, 300×g. Molecule: Cholesteryl-TEG-Cholesteryl-TEG-(SpacerC18)7-Fluos-Biotin-TEG.

Figure 18:
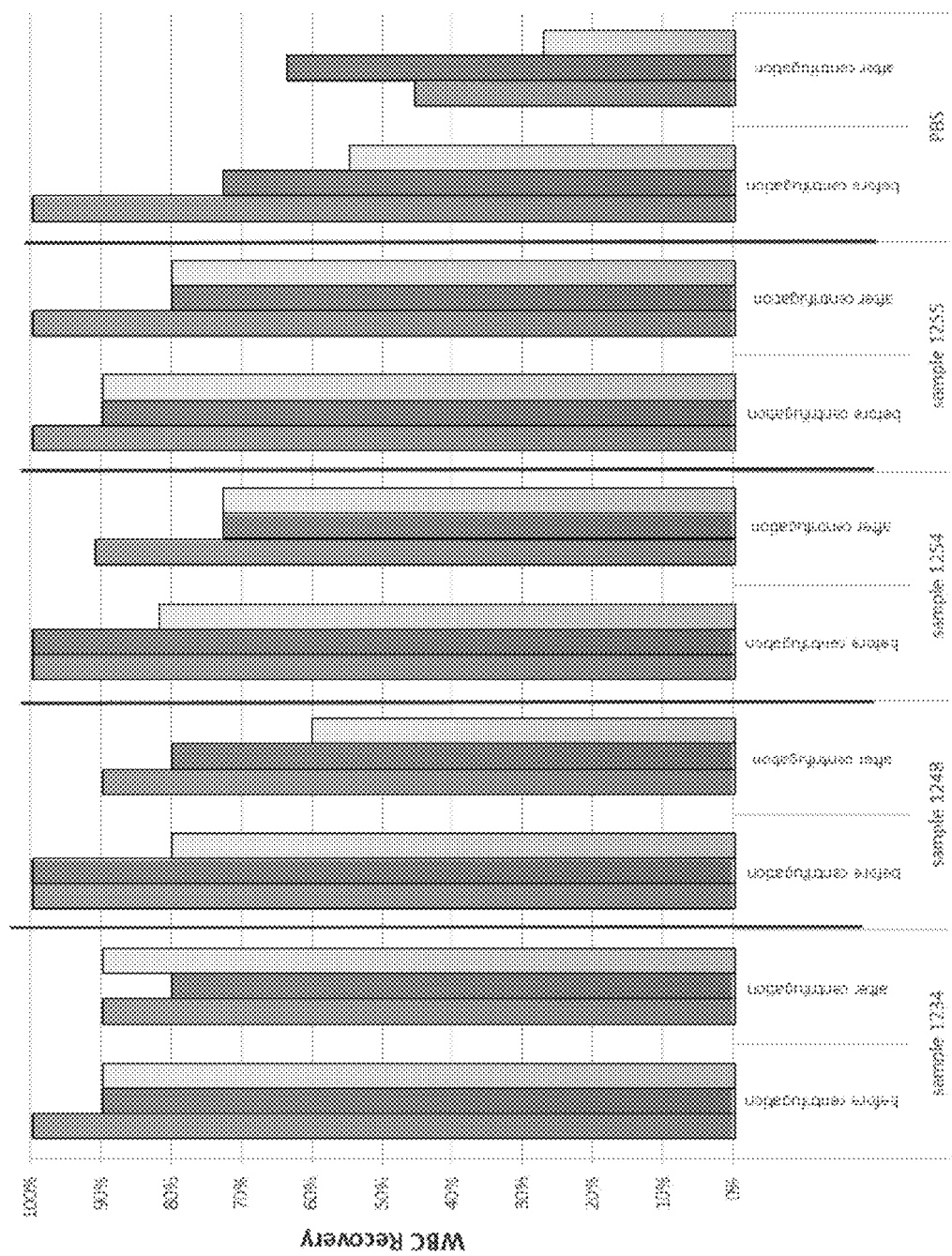
FIG. 18: shows WBC recovery rate after centrifugation at different points of time and centrifugation settings. Following molecules were tested: 1255: 3'-(Myristic acid)2-PEG2000-dT-Biotin-TEG-5' INVERS; 1234: 5'-(Cholesteryl-TEG)2-Spacer C18-dT-Biotin-TEG-3'; 1248: 3'-(Cholesteryl-TEG)2-PEG2000-Fluos-Biotin-TEG-5' INVERS; 1254: 3'-(Cholesteryl-TEG)2-SpacerC18-Fluos-Biotin-TEG-5' INVERS. All molecules enable cell immobilization within 2 hours. WBCs in PBS are damaged during centrifugation at 500×g for 20 min. Molecule 1234 shows the best performance followed by molecule 1255 and 1254. Centrifugation characteristics: 20 min, 500×g. Respective left column: 10 min incubation with molecule. Respective middle column: 1 h min incubation with molecule. Respective right column: 3 h incubation with molecule.

D) WBC Recovery Rate After Centrifugation—Different Points of Time and Centrifugation Settings The results of the first experiment are shown in FIG. 18. Following molecules were tested:
1234: 5'-(Cholesteryl-TEG)2-Spacer C18-dT-Biotin-TEG-3'
1248: 3'-(Cholesteryl-TEG)2-PEG2000-Fluos-Biotin-TEG-5' INVERS 1254: 3'-(Cholesteryl-TEG)2-SpacerC18-Fluos-Biotin-TEG-5' INVERS
1255: 3'-(Myristic acid)2-PEG2000-dT-Biotin-TEG-5' INVERS All molecules enable cell immobilization within 2 hours
WBCs in PBS are damaged during centrifugation at 300×g for 20 min
Molecule 1234 shows the best performance followed by compound 1255 and 1254
Centrifugation characteristics: 20 min, 300×g.

Figure 19:
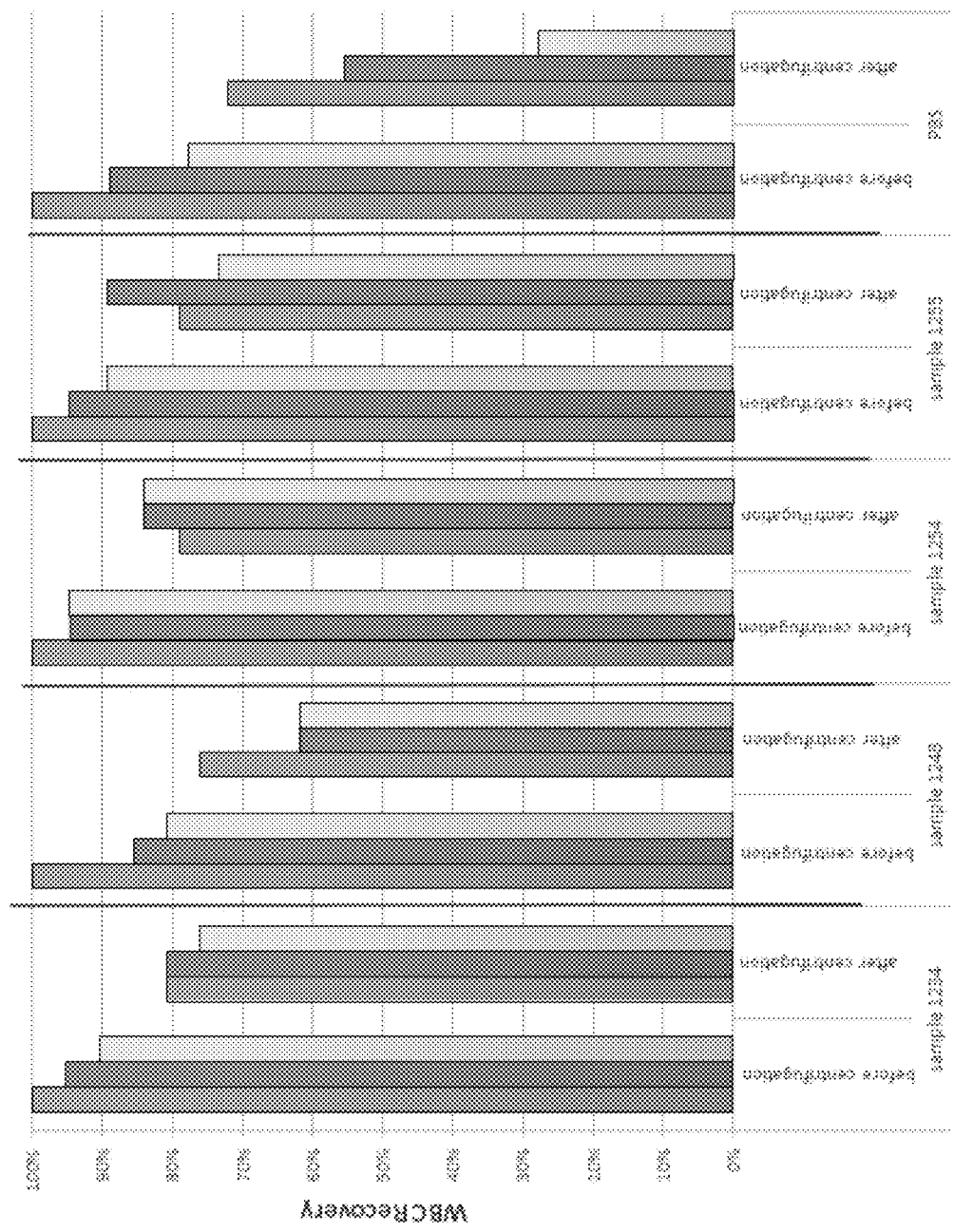
FIG. 19: shows WBC recovery rate after centrifugation at different points of time and centrifugation settings. Following molecules were tested: 1255: 3'-(Myristic acid)2-PEG2000-dT-Biotin-TEG-5' INVERS; 1234: 5'-(Cholesteryl-TEG)2-Spacer C18-dT-Biotin-TEG-3'; 1248: 3'-(Cholesteryl-TEG)2-PEG2000-Fluos-Biotin-TEG-5' INVERS; 1254: 3'-(Cholesteryl-TEG)2-SpacerC18-Fluos-Biotin-TEG-5' INVERS. All molecules enable cell immobilization within 2 hours. WBCs in PBS are damaged during centrifugation at 1000×g for 20 min. Centrifugation characteristics: 20 min, 1000×g. Respective left column: 10 min incubation with molecule. Respective middle column: 1 h min incubation with molecule. Respective right column: 2 h incubation with molecule.
Figure 20:
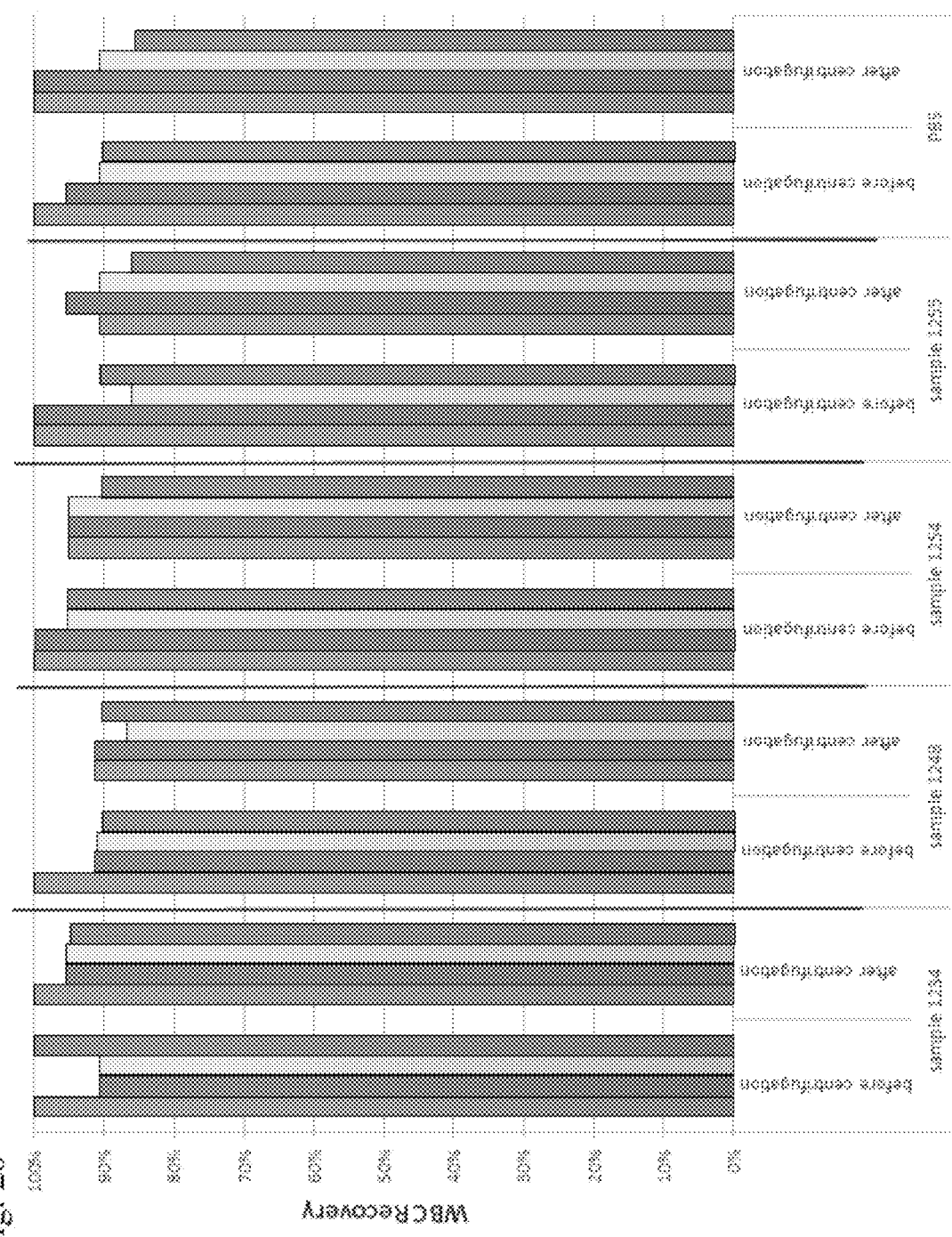
FIG. 20: shows Jurkat cell recovery rate after centrifugation at different points of time. Respective columns from left: 1: 10 min incubation with molecule. 2: 1 h incubation with molecule. 3: 3.5 h incubation with molecule. 4: 5.5 h min incubation with molecule. Following molecules were tested: 1255: 3'-(Myristic acid)2-PEG2000-dT-Biotin-TEG-5' INVERS. 1234: 5'-(Cholesteryl-TEG)2-Spacer C18-dT-Biotin-TEG-3'; 1248: 3'-(Cholesteryl-TEG)2-PEG2000-Fluos-Biotin-TEG-5' INVERS; 1254: 3'-(Cholesteryl-TEG)2-SpacerC18-Fluos-Biotin-TEG-5' INVERS. Jurkat culture cells are stable during centrifugation processes in PBS as well as using different molecules within 5.5 h. Centrifugation characteristics: 20 min, 500×g.

The results of the second experiment in this context are shown in FIG. 19. Following molecules were tested:
1255: 3'-(Myristic acid)2-PEG2000-dT-Biotin-TEG-5' INVERS 1234: 5'-(Cholesteryl-TEG)2-Spacer C18-dT-Biotin-TEG-3'
1248: 3'-(Cholesteryl-TEG)2-PEG2000-Fluos-Biotin-TEG-5' INVERS
1254: 3'-(Cholesteryl-TEG)2-SpacerC18-Fluos-Biotin-TEG-5' INVERS The results are as follows:
All molecules enable cell immobilization within 2 hours
WBCs in PBS are damaged during centrifugation at 500×g for 20 min
Molecule 1234 shows the best performance followed by molecule 1255 and 1254
Centrifugation characteristics: 20 min, 500×g. The results of the third experiment in this context are shown in FIG. 20. Following molecules were tested:
1255: 3'-(Myristic acid)2-PEG2000-dT-Biotin-TEG-5' INVERS
1234: 5'-(Cholesteryl-TEG)2-Spacer C18-dT-Biotin-TEG-3'
1248: 3'-(Cholesteryl-TEG)2-PEG2000-Fluos-Biotin-TEG-5' INVERS
1254: 3'-(Cholesteryl-TEG)2-SpacerC18-Fluos-Biotin-TEG-5' INVERS The results are as follows:
All molecules enable cell immobilization within 2 hours
WBCs in PBS are damaged during centrifugation at 1000×g for 20 min
Centrifugation characteristics: 20 min, 500×g.

E) Jurkat Recovery Rate After Centrifugation—Different Points of Time

Figure 21A:
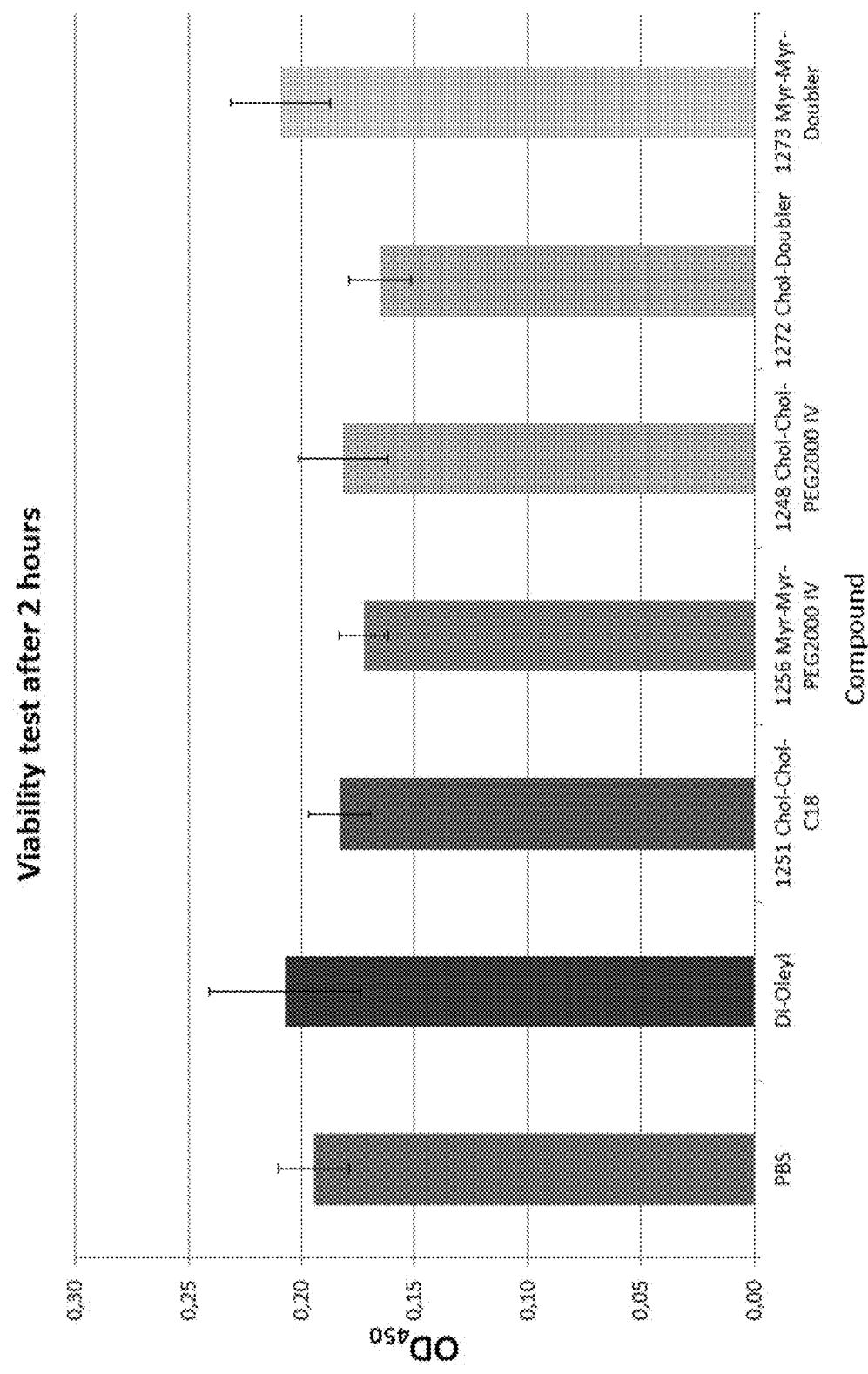
FIG. 21A: shows that tri-functional linker moieties do not influence cell viability. Cell viability test using WST-1 proliferation kit (RAS) was performed, employing different compounds for use according to the invention differing in the trifunctional linker moieties. The different linkers appear not to influence the cell viability during linker incubation time of 4 hours. Viability test after 2 hours.
Figure 21B:
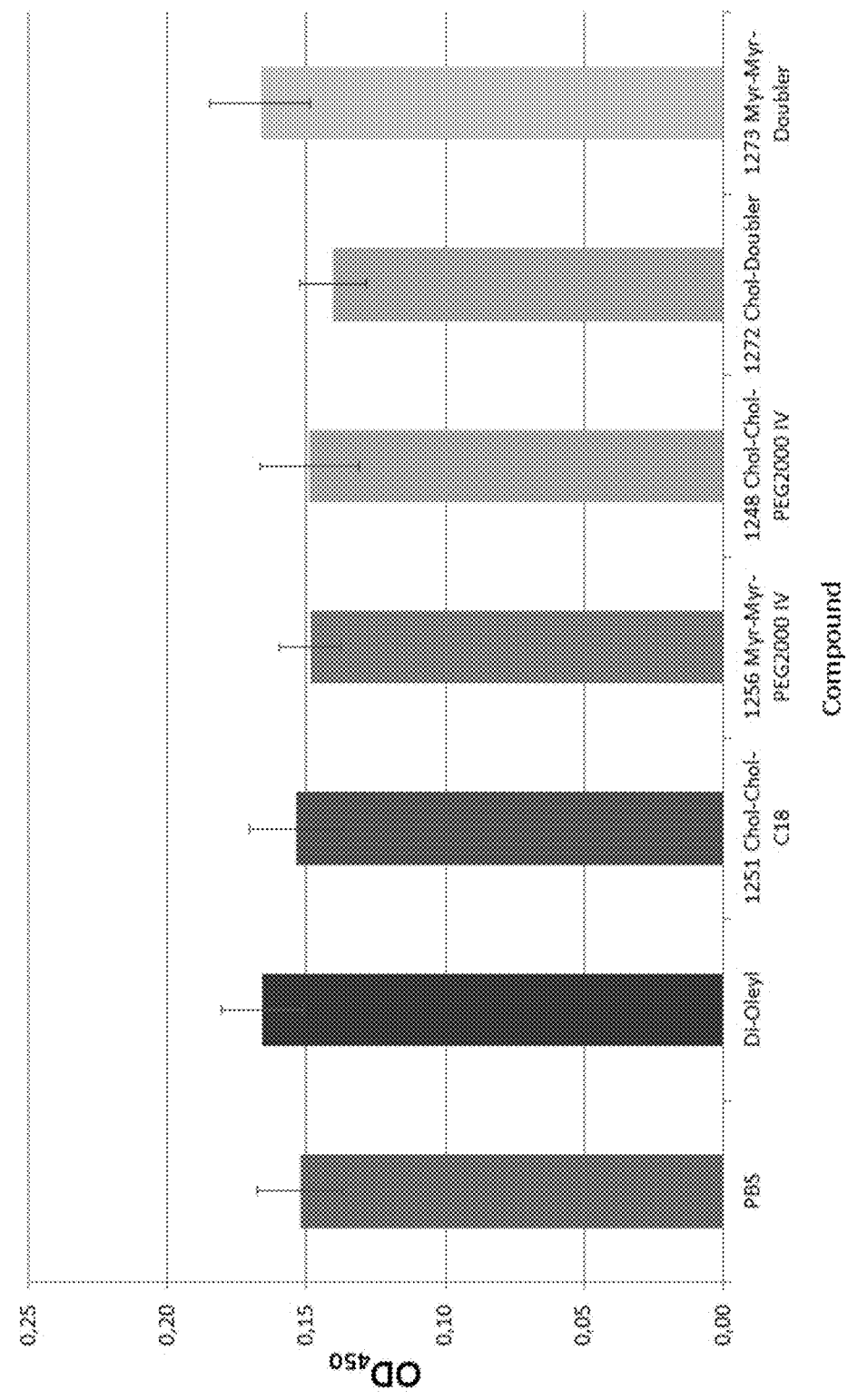
FIG. 21B: shows that tri-functional linker moieties do not influence cell viability. Cell viability test using WST-1 proliferation kit (RAS) was performed, employing different compounds for use according to the invention differing in the trifunctional linker moieties. The different linkers appear not to influence the cell viability during linker incubation time of 4 hours. Viability test after 4 hours.

The results of this experiment are shown in FIG. 21. Following molecules were tested:
1255: 3'-(Myristic acid)2-PEG2000-dT-Biotin-TEG-5' INVERS
1234: 5'-(Cholesteryl-TEG)2-Spacer C18-dT-Biotin-TEG-3'
1248: 3'-(Cholesteryl-TEG)2-PEG2000-Fluos-Biotin-TEG-5' INVERS 1254: 3'-(Cholesteryl-TEG)2-SpacerC18-Fluos-Biotin-TEG-5' INVERS The results are as follows:

Jurkat culture cells are stable during centrifugation processes in PBS as well as using different molecules within 5.5 h.

Centrifugation characteristics: 20 min, 500×g.

F) Tri-Functional Linker Moieties do not Influence Cell Viability

Figure 22A:
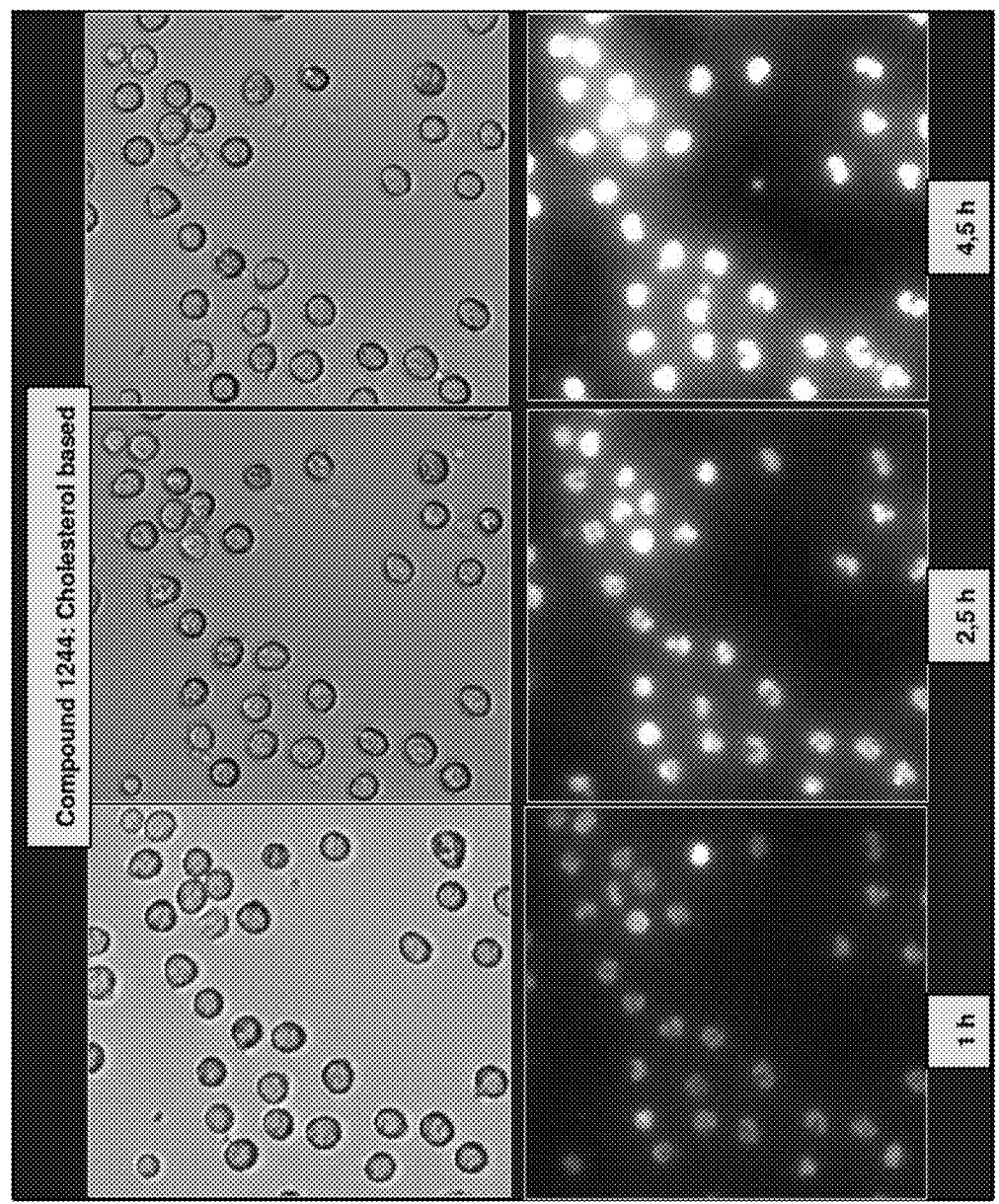
FIG. 22A: shows that tri-functional linker moieties do not influence cell viability. It was found that the tested compounds for use according to the invention, namely No. 1244 as compound with cholesterol-moiety, do not influence cell morphology during linker incubation time of 4.5 hours. Left pictures: 1 h incubation. Middle pictures: 2.5 h incubation. Right pictures: 4.5 h incubation. Upper pictures: Brightfield. Lower pictures: DAPI.

The results of a first experiment in this context are shown in FIGS. 22A and B.

Figure 22B:
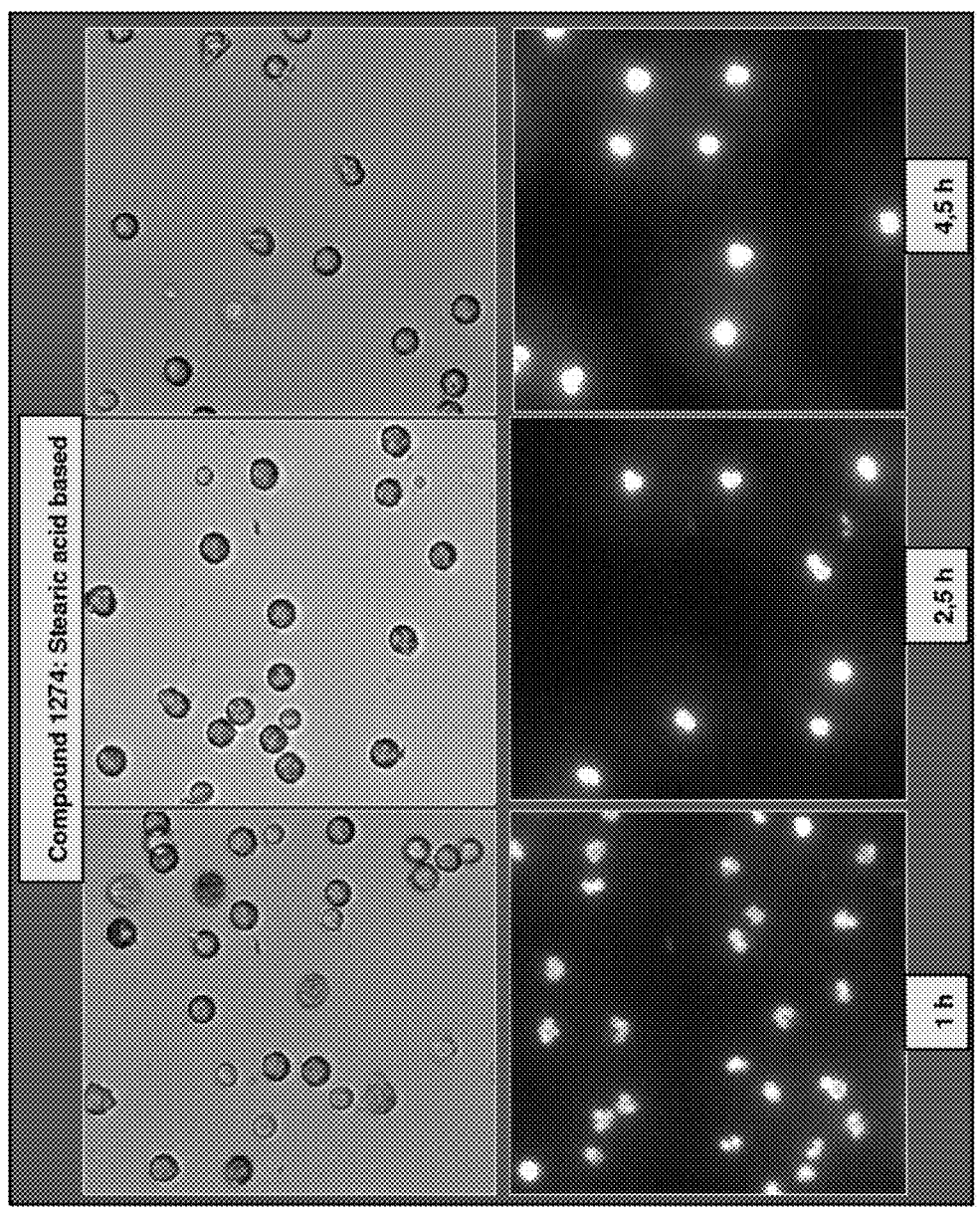
FIG. 22B: shows that tri-functional linker moieties do not influence cell viability. It was found that the tested compounds for use according to the invention, namely No. 1274 as compound with stearic acid-moiety, do not influence cell morphology during linker incubation time of 4.5 hours. Left pictures: 1 h incubation. Middle pictures: 2.5 h incubation. Right pictures: 4.5 h incubation. Upper pictures: Brightfield. Lower pictures: DAPI.

Cell viability test using WST-1 proliferation kit (RAS) was performed, employing different molecules useful in methods of the invention differing in the trifunctional linker moieties. ⇒ The different linkers do not influence the cell viability during linker incubation time of 4 hours, as can be seen from FIG. 22.

Figure 23:
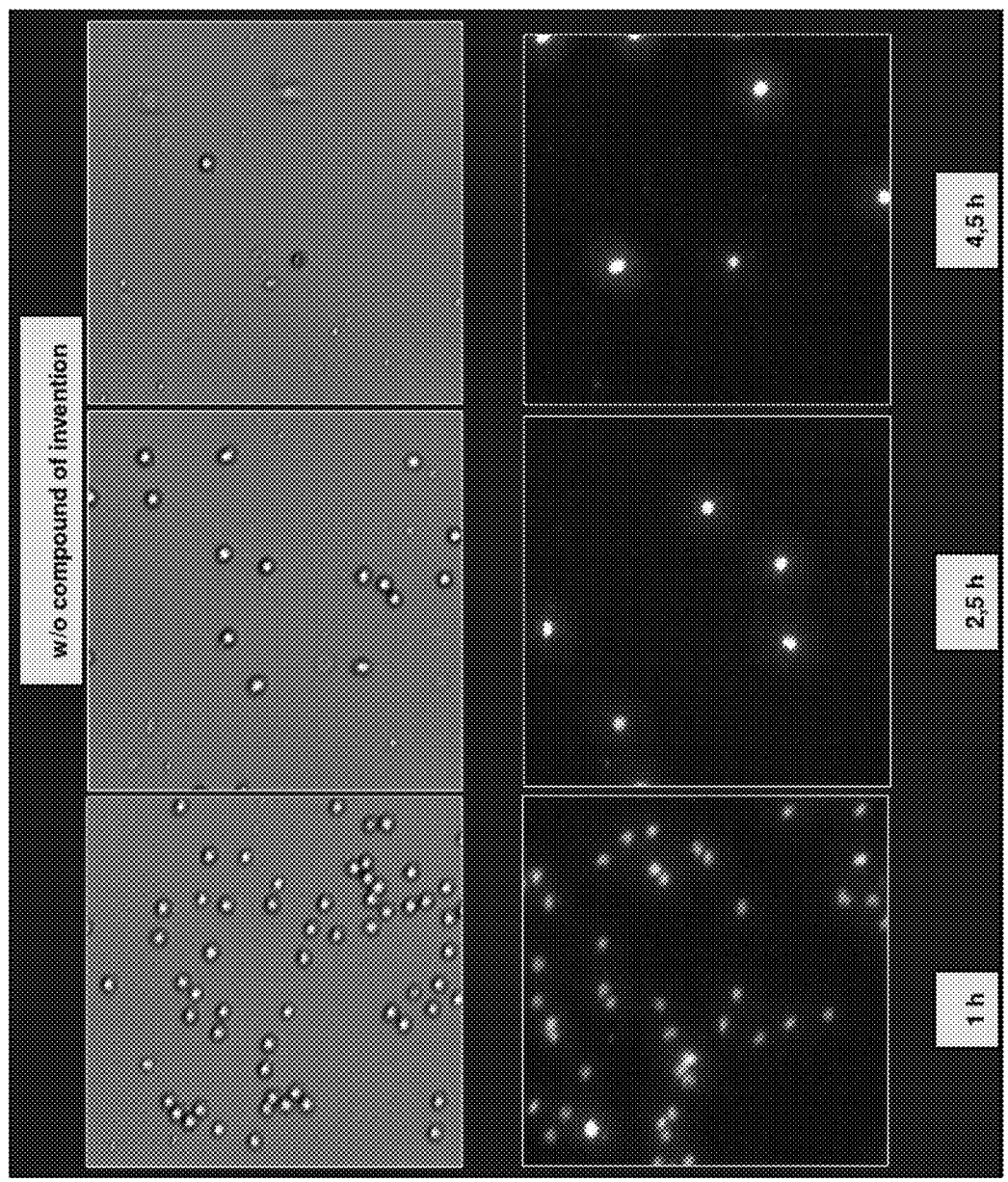
FIG. 23: shows cell morphology without linker incubation at different points of time. Without compound for use according to the invention addition, cells diffuse away during an incubation time of 4.5 hours. Cell morphology is not influenced in left cells during the incubation time. Left pictures: 1 h incubation. Middle pictures: 2.5 h incubation. Right pictures: 4.5 h incubation. Upper pictures: Brightfield. Lower pictures: DAPI.

The results of a second experiment in this context are shown in FIGS. 23A and B. It was found that the tested molecules useful in methods of the invention (No. 1244 and 1274) do not influence cell morphology during linker incubation time of 4.5 hours.

Figure 24:
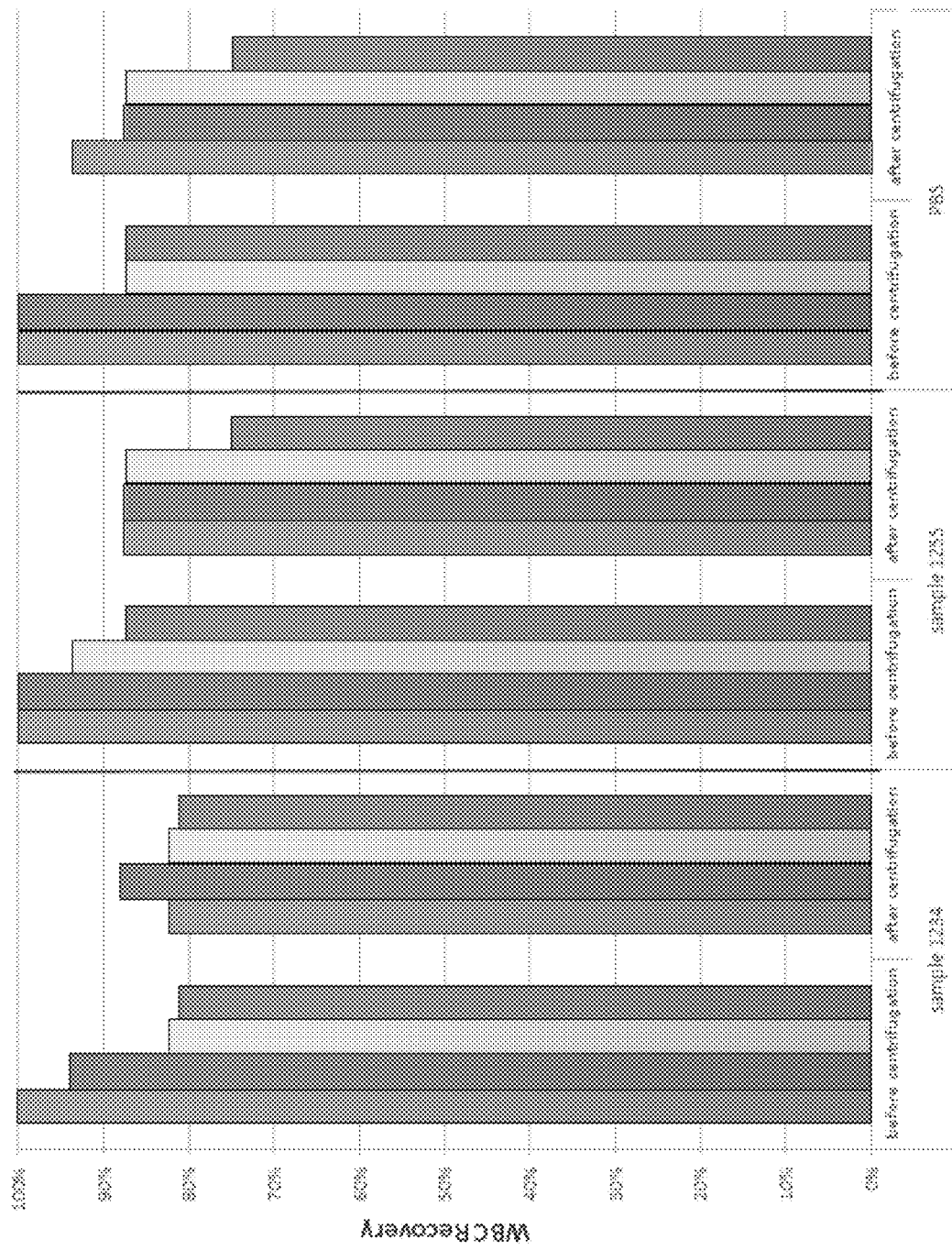
FIG. 24: shows MDA-MB468 cell recovery rate after centrifugation at different points of time. Respective columns from left: 1: 10 min incubation with molecule. 2: 1 h incubation with molecule. 3: 3 h incubation with molecule. 4: 5 h min incubation with molecule. Following compounds for use according to the invention were tested: 1234: 5'-(Cholesteryl-TEG)2-Spacer C18-dT-Biotin-TEG-3'; 1255: 3'-(Myristic acid)2-PEG2000-dT-Biotin-TEG-5' INVERS. MDA-MB468 culture cells are stable during centrifugation processes in PBS as well as using different compounds for use according to the invention within 5 h. Centrifugation characteristics: 20 min, 500×g.

G) Cell Morphology without Incubation with Molecule Useful in Methods of Invention—Different Points of Time The result of this experiment is shown in FIG. 24. Following was found:

Without molecule useful in methods of the invention addition, cells diffuse away during an incubation time of 4.5 hours Cell morphology is not influenced in left cells during the incubation time.

H) MDA-MB468 Recovery Rate After Centrifugation—Different Points of Time

The result of this experiment is shown in FIG. 25. Following compounds useful in methods of the invention were tested:

1234: 5'-(Cholesteryl-TEG)2-Spacer C18-dT-Biotin-TEG-3'

1255: 3'-(Myristic acid)2-PEG2000-dT-Biotin-TEG-5' INVERS

Following was found:

MDA-MB468 culture cells are stable during centrifugation processes in PBS as well as using different molecules useful in methods of the invention within 5 h.

Centrifugation characteristics: 20 min, 500×g.

Example 6

Comparison of SA-Plate (Streptavidin-Plate) Incubated with Compound Useful in Methods of the Invention vs WBC (White Blood Cells) Incubated with Compound Useful in Methods of the Invention As starting material 5'-(Cholesteryl-TEG)2-PEG2000-Fluos-Biotin_TEG-3' INVERS (14530 pmol/μl) (Internal Reference No.: 29.891250), and a streptavidin treated MTP (Microcoat), 12 Well plate were used.

Erythrocyte lysis was performed as follows:

EDTA-whole blood 59.423 6.400 WBC/μl (Ambulanz Roche)

lysis buffer: 100 mM NH4Cl+5 mM Hepes+0.5 mM KHCO3+0.1 mM EDTA-K

Figure 2:
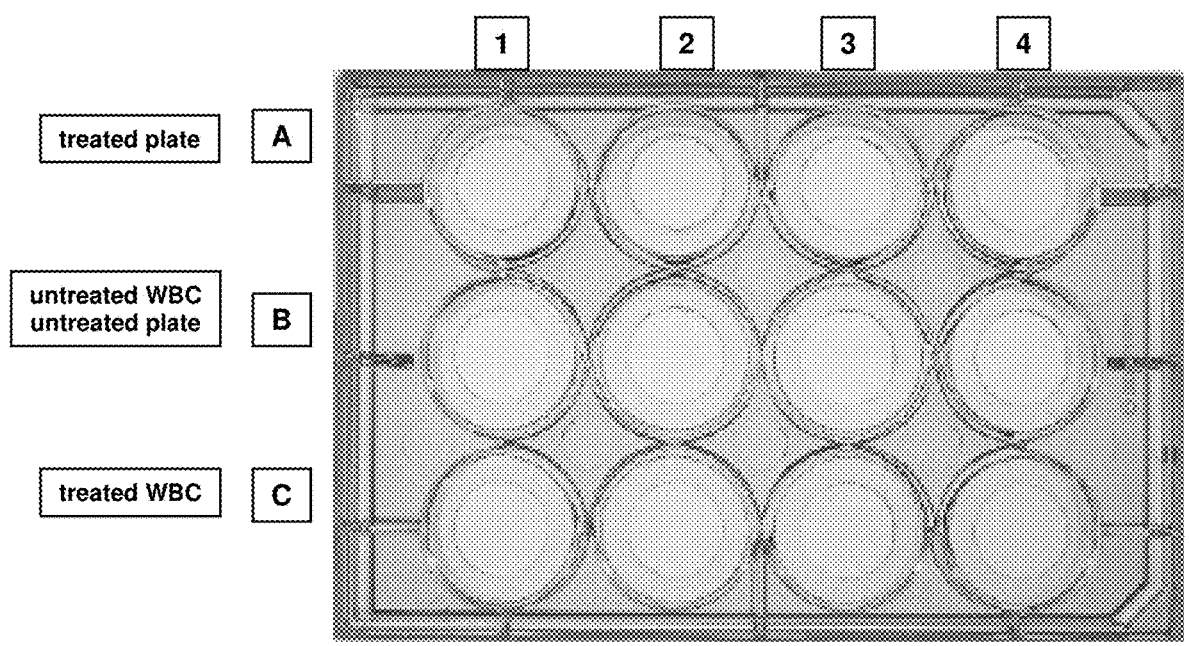
FIG. 2: shows the design of the Experiment of Example 6. 4× determination. Row A: 200 µl PBS introduced, 1 nmol of compound added thereto respectively, mixed, incubated about 30 min, washed 2×PBS, 800 µl PBS introduced, 300.000 WBC (untreated) added. Row B: 800 µl PBS introduced, 300.000 WBC (untreated) added. Row C: 10×10^6 WBC in 1 ml with 10 nmol compound of invention 10 min incubated, 800 µl PBS/Well introduced, 300.000 treated WBC respectively. The first MTP plate washed after 30 min 2× with PBS, overlayed with Höchst and incubated for 15 min.>Cellavista (Operator s9s5) measured. The second plate was measured after 90 min. The third plate was measured after 150 min.

Ca 1×8 ml whole blood filled in 50 ml Falcon tube with lysis buffer, incubate at room temperature for 10 min 15 min at 250 g centrifugated, pellet resuspended by pipetting in and out in lysis buffer; filled to 50 ml with lysis buffer 15 min 250 g centrifugated, pellet resuspended with PBS, filled to 50 ml with PBS, 15 min 250 g centrifugated, filled to 50 ml with PBS WBC measured at Sysmex 1: 37.100 WBC/μl The design of the experiment on the plate is explained below (see FIG. 2):

3×12 Well MTP: Treatment of the WBC with compounds useful in methods of the invention:

4× determination:

Row A: 200 μl PBS introduced, 1 nmol of compound added thereto respectively, mixed, incubated about 30 min, washed 2× PBS, 800 μl PBS introduced, 300.000 WBC (untreated) added.

Row B: 800 μl PBS introduced, 300.000 WBC (untreated) added.

Row C: 10×10^6 WBC in 1 ml with 10 nmol compound useful in methods of invention 10 min incubated, 800 μl PBS/Well introduced, 300.000 treated WBC respectively.

The first MTP plate washed after 30 min 2× with PBS, overlaid with Höchst and incubated for 15 min.>Cellavista (Operator s9s5) measured.

The second plate was measured after 90 min.

The third plate was measured after 150 min.

Figure 4:
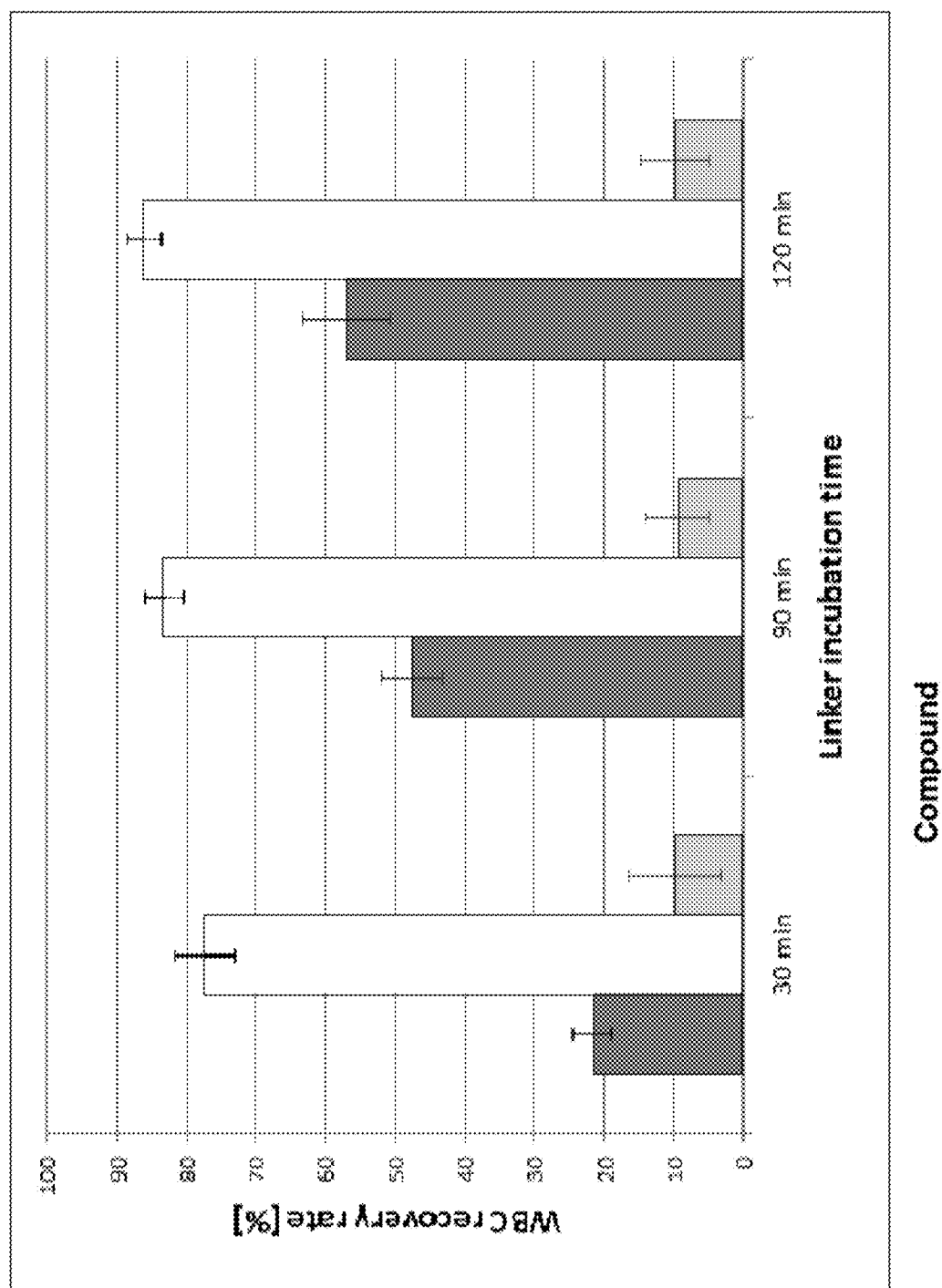
FIG. 4: shows the results of Example 6 after 30, 90 or 120 minutes incubation as a graph.
Figure 5:
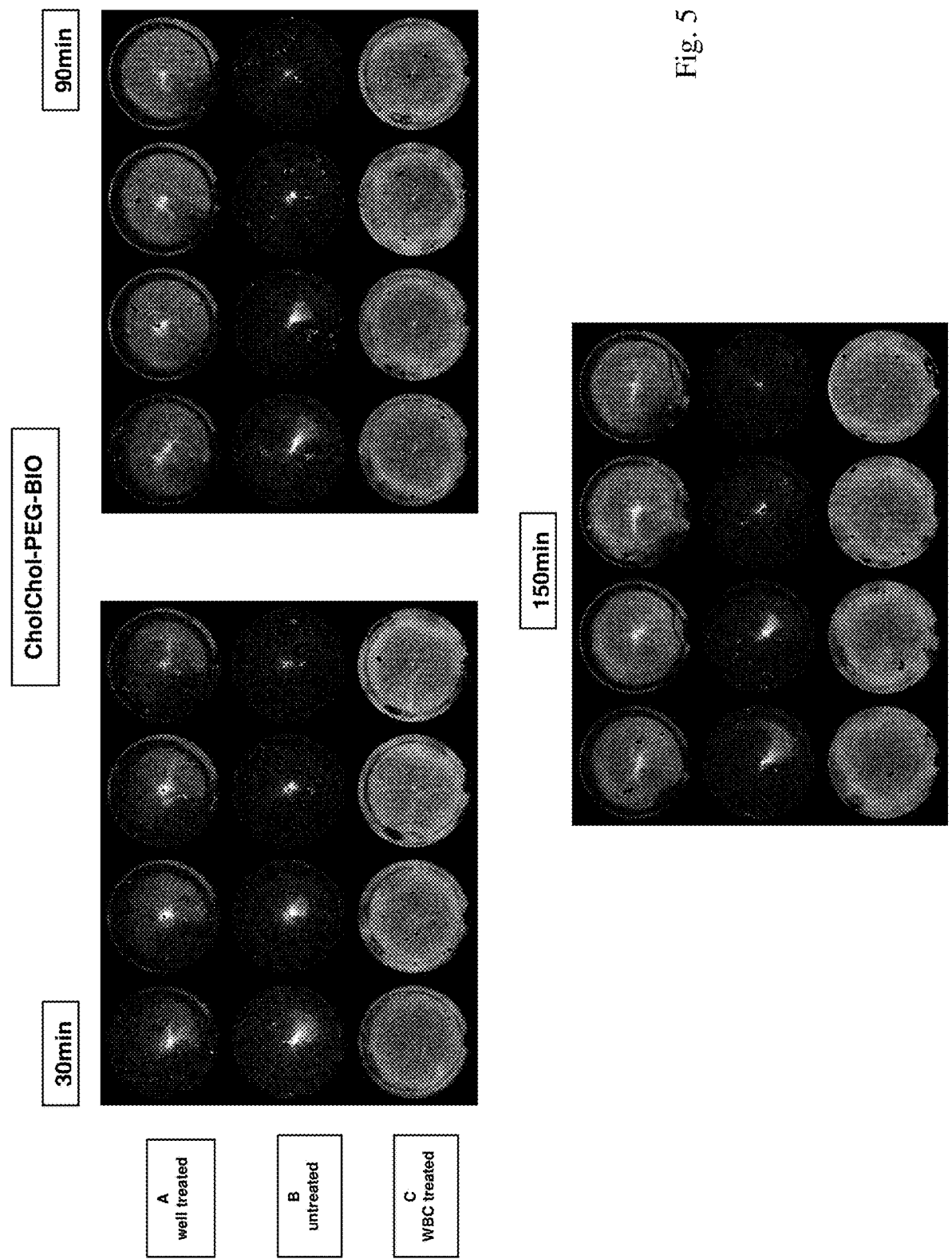
FIG. 5: shows the plates of Example 6 after 30, 90 or 150 minutes incubation.

The calculated results are shown in FIG. 3. A graph representing these results is depicted in FIG. 4. The plates of the experiments are shown in FIG. 5.

It was found that the method of the invention is clearly and surprisingly advantageous.

The invention claimed is:

1. A method comprising:
providing a compound comprising two or more hydrophobic domains attached to a hydrophilic domain,
wherein the two or more hydrophobic domains are covalently bound to said hydrophilic domain, and wherein the two or more hydrophobic domains each comprise a linear lipid, cholesterol or a hydrophobic vitamin, and wherein the hydrophilic domain comprises a polyethylene glycol (PEG) moiety, and
contacting said compound to a cell under in vitro conditions allowing the compound to incorporate into the membrane of the cell, wherein said contacting results in stabilization of the cell, wherein said compound comprises a compound of Formula (I):

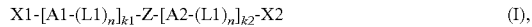

$$X1\text{-}[A1\text{-}(L1)_n]_{k1}\text{-}Z\text{-}[A2\text{-}(L1)_n]_{k2}\text{-}X2 \qquad (I),$$

wherein Z is a linear polyethylene glycol (PEG) moiety containing 2 to 100 linear PEG moieties, wherein the linear PEG moiety optionally comprises 1 or more spacer moieties SP connecting two —O—CH$_2$—CH$_2$— moieties, and wherein the linear PEG moiety optionally comprises a linker moiety L3 at one or both ends, each L1 is a linker moiety selected independently from each other, each n is either 0 or 1, selected independently from each other, A1 and A2 are bifunctional or trifunctional moieties selected independently from each other, and at least one A1 or A2 is trifunctional, k1 and k2 are integers between 0 and 10, selected independently from each other, and at least one of k1 and k2 is not 0, X1 and X2 are independently selected from hydrogen, a protecting group, and a hydrophobic group, L3 is independently selected from a linear alkyl or alkenyl chain with 1 to 10 C atoms, which is optionally (i) interrupted by 1 to 3 N, O or S atoms, and/or (ii) substituted by 1 to 4 hydroxyl, carbonyl, amino or thiol groups, and wherein the two or more hydrophobic domains are covalently bound to said hydrophilic domain via the trifunctional moieties, or a salt thereof.

2. The method of claim 1, wherein Z in Formula (I) has the following structure:

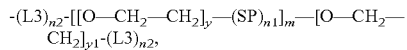
-(L3)$_{n2}$-[[O—CH$_2$—CH$_2$]$_y$—(SP)$_{n1}$]$_m$—[O—CH$_2$—CH$_2$]$_{y1}$-(L3)$_{n2}$, wherein SP is a spacer moiety, n1 is either 0 or 1, each n2 is either 0 or 1, selected independently of each other, m is an integer from 1 to 100, y is an integer from 1 to 100, y1 is an integer from 0 to 30, with the proviso that y*m+y1≤100, L3 is independently selected from a linear alkyl chain with 1 to 10 C atoms and a linear alkenyl chain with 2 to 10 C atoms, wherein said linear alkyl chain or linear alkenyl chain is optionally (i) interrupted by 1 to 3 N, O or S atoms, and/or (ii) substituted by 1 to 4 hydroxyl, carbonyl, or thiol groups.

3. The method of claim 2, wherein (a) n1 is identical for the m moieties —[[O—CH$_2$—CH$_2$]$_y$—(SP)$_{n1}$]—, and/or (b) y1 is 0, and/or (c) y is 4, 5, or 6, and n1 is 1, and/or (d) the spacer moieties SP are independently from each other selected from the group consisting of a phosphate, and a bifunctional moiety, and/or (e) n2 is both 0, or (f) one or both n2=1, and L3 is an alkyl group with 1 to 10 C atoms which optionally contains an amide group, carbonyl group, carbamate, and/or NH group.

4. The method of claim 1, wherein X1 or X2 is a hydrophobic domain.

5. The method of claim 4, wherein the linear lipid is (a) a saturated or unsaturated fatty acid, and/or (b) a fatty acid having from 8 to 26 C atoms, or the linear lipid is selected from the group consisting of oleic acid, myristic acid, stearic acid and behenic acid.

6. The method of claim 1, wherein the hydrophobic vitamin is α-tocopherol.

7. The method of claim 1, wherein (a) the linkers L1 are independently selected from the group consisting of a phosphate, amide, carbamate, and ester group, and/or (b) moieties A1 and A2 are independently selected from a bifunctional group selected from the group consisting of a phosphate group, carbamate group, amide group, a moiety comprising a nucleobase, and a linear alkyl group having 1 to 10 C atoms and which alkyl chain contains functional groups at the terminal C-atoms independently selected from amine, carbonyl, hydroxyl, thiol, and carbonic acid groups, and a trifunctional moiety having 1 to 10 C atoms and comprising at least one —OH, —SH and/or at least one —NH$_2$ group, and/or (c) the linkers L2 are independently selected from the group consisting of a phosphate, amide, carbamate, an ester group and a moiety —[[O—CH$_2$—CH$_2$]$_{y2}$—(SP)$_n$]$_{m1}$—, wherein SP and n are as in claim 3, y2 is an integer from 1 to 30, and m1 is an integer from 1 to 10.

8. A method of stabilizing a cell during exposure to shear forces, the method comprising (a) providing a compound as defined in claim 1; and (b) contacting a cell with the compound under conditions allowing the interaction of the compound with the membrane of the cell wherein the compound incorporates into the membrane of the cell, thereby stabilizing the cell, and (c) applying shear forces to the cell.

9. The method of claim 8, wherein the applying shear forces to the cell is by centrifugation, large scale cell cultivation, flow cytometry, fluorescence-activated cell sorting and/or bead-based cell separation.

* * * * *